United States Patent
Elinav et al.

(10) Patent No.: US 12,161,679 B2
(45) Date of Patent: Dec. 10, 2024

(54) MICROBIOME-BASED DIAGNOSIS, PREDICTION AND TREATMENT OF RELAPSING OBESITY

(71) Applicant: Yeda Research and Development Co. Ltd., Rehovot (IL)

(72) Inventors: Eran Elinav, Mazkeret Batya (IL); Eran Segal, Ramat-HaSharon (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 851 days.

(21) Appl. No.: 17/318,009

(22) Filed: May 12, 2021

(65) Prior Publication Data

US 2021/0260139 A1 Aug. 26, 2021

Related U.S. Application Data

(62) Division of application No. 16/077,751, filed as application No. PCT/IL2017/050187 on Feb. 14, 2017, now abandoned.

(60) Provisional application No. 62/423,299, filed on Nov. 17, 2016, provisional application No. 62/295,094, filed on Feb. 14, 2016.

(51) Int. Cl.
| | | |
|---|---|---|
| A61K 35/741 | (2015.01) | |
| A23L 33/00 | (2016.01) | |
| A23L 33/105 | (2016.01) | |
| A23L 33/135 | (2016.01) | |
| A61K 31/352 | (2006.01) | |
| A61K 35/74 | (2015.01) | |
| A61P 3/04 | (2006.01) | |
| C12Q 1/02 | (2006.01) | |
| C12Q 1/689 | (2018.01) | |

(52) U.S. Cl.
CPC .......... *A61K 35/741* (2013.01); *A23L 33/105* (2016.08); *A23L 33/135* (2016.08); *A23L 33/30* (2016.08); *A61K 31/352* (2013.01); *A61K 35/74* (2013.01); *A61P 3/04* (2018.01); *C12Q 1/02* (2013.01); *C12Q 1/689* (2013.01); *A23V 2002/00* (2013.01); *A23V 2200/332* (2013.01); *A23V 2250/2116* (2013.01)

(58) Field of Classification Search
CPC .......... A61P 3/04; A61K 35/74; A61K 35/741
See application file for complete search history.

(56) References Cited

U.S. PATENT DOCUMENTS

2019/0142875 A1   5/2019   Elinav et al.

FOREIGN PATENT DOCUMENTS

| KR | 10-2010-0128041 | 12/2010 |
|---|---|---|
| WO | WO 2008/076696 | 6/2008 |
| WO | WO 2014/060542 | 4/2014 |
| WO | WO 2014/177667 | 11/2014 |
| WO | WO 2017/138007 | 8/2017 |
| WO | WO 2017/138007 A8 | 8/2017 |

OTHER PUBLICATIONS

European Search Report and the European Search Opinion Dated Jul. 22, 2020 From the European Patent Office Re. Application No. 19203149.0. (9 Pages).
Final Official Action Dated Nov. 13, 2020 from the US Patent and Trademark Office Re. U.S. Appl. No. 16/077,751. (15 pages).
International Preliminary Report on Patentability Dated Mar. 5, 2018 From the International Preliminary Examining Authority Re. Application No. PCT/IL2017/050187. (14 Pages).
International Search Report and the Written Opinion Dated May 15, 2017 From the International Searching Authority Re. Application No. PCT/IL2017/050187. (17 Pages).
Official Action Dated Jul. 23, 2020 from the US Patent and Trademark Office Re. U.S. Appl. No. 16/077,751. (12 pages).
Thaiss et al. "Persistent Microbiome Alterations Modulate the Rate of Post-Dieting Weight Regain", Nature, XP055368743, 540(7634): 544-551, Published Online Nov. 24, 2016. Abstract.
Communication Pursuant to Article 94(3) EPC Dated Feb. 14, 2023 From the European Patent Office Re. Application No. 19203149.0. (8 Pages).

*Primary Examiner* — Ruth A Davis

(57) ABSTRACT

A method of analyzing the likelihood of weight regain in a subject who has reached a target weight by practicing a weight loss program is disclosed. The method comprises determining an amount or presence of at least one microbe and/or product thereof in the gut microbiome of the subject, wherein the amount of the at least one microbe is altered during a prior weight gain period of the subject to reach a level representative of an obese subject and further wherein the amount of the at least one microbe is retained at the level following the weight loss program, wherein the amount or presence of the at least one microbe or product thereof is predictive of weight regain.

7 Claims, 45 Drawing Sheets
(45 of 45 Drawing Sheet(s) Filed in Color)
Specification includes a Sequence Listing.

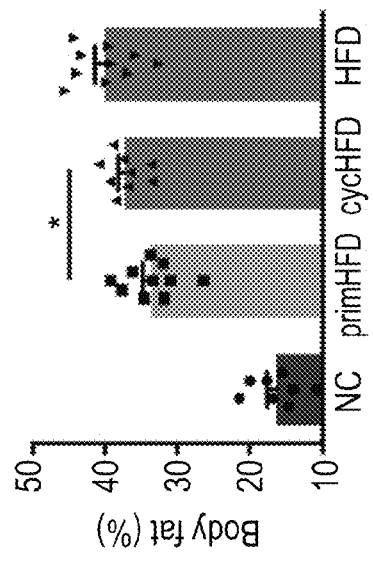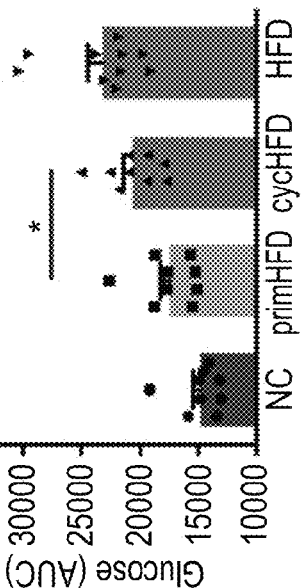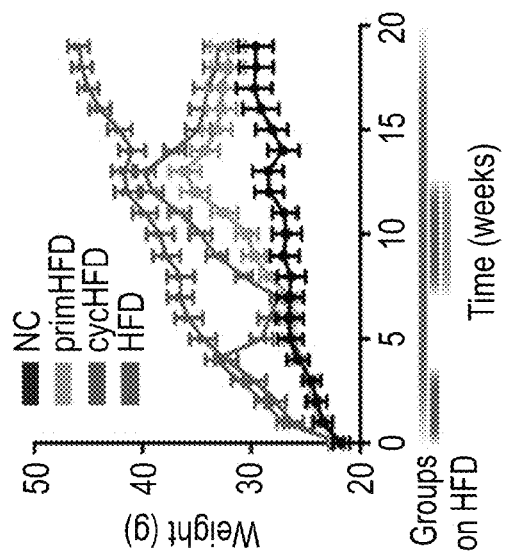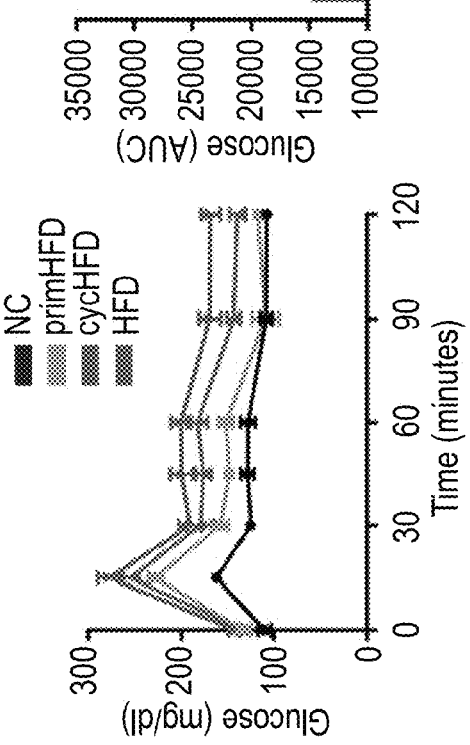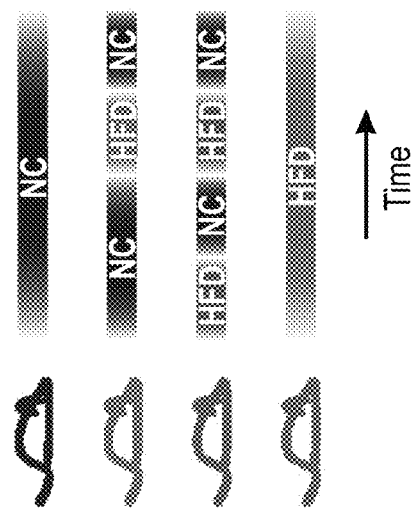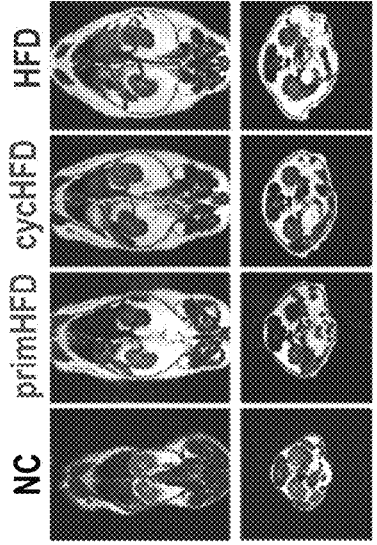

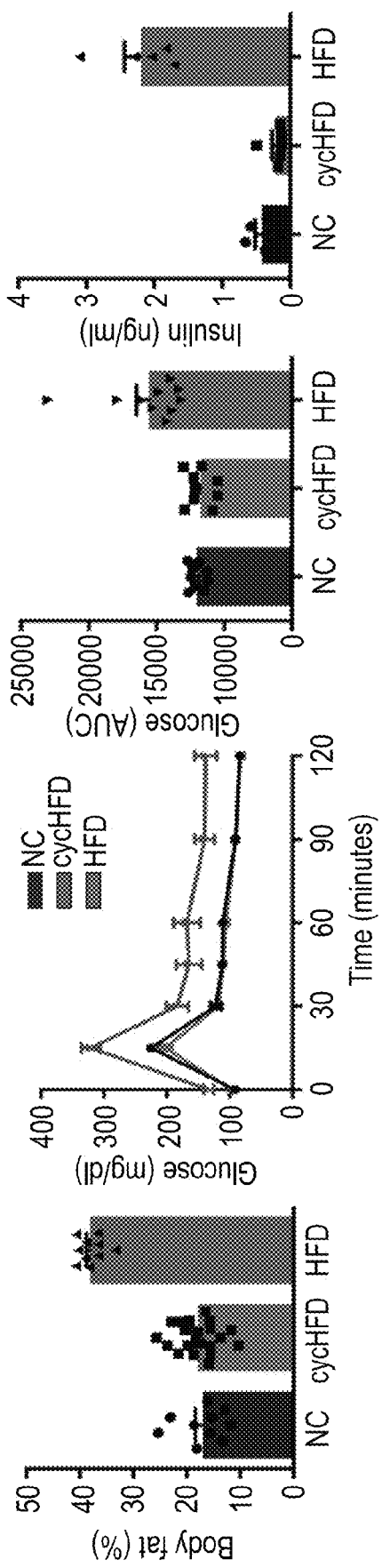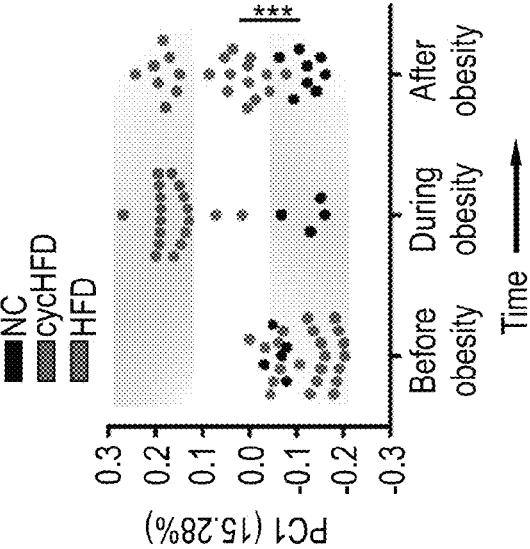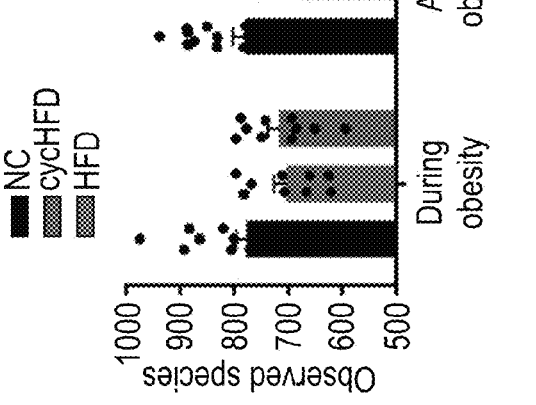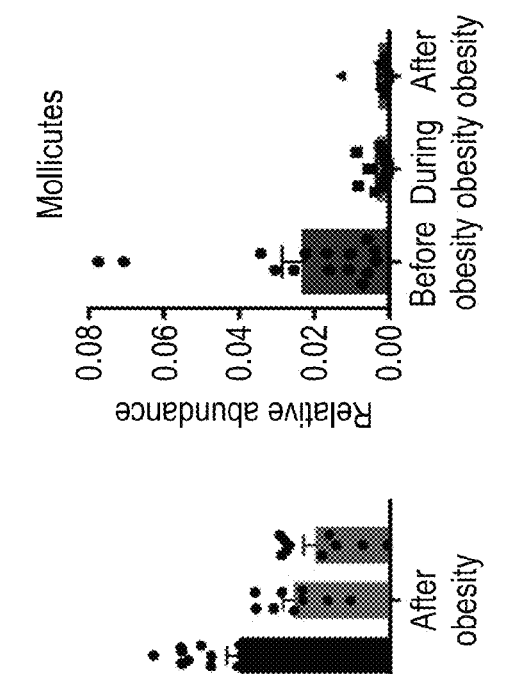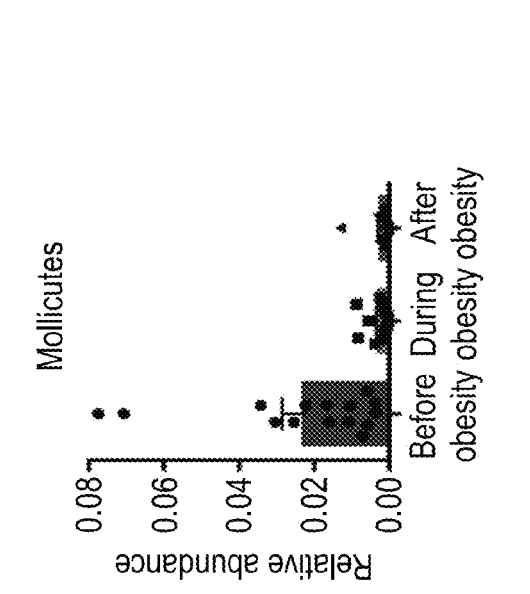

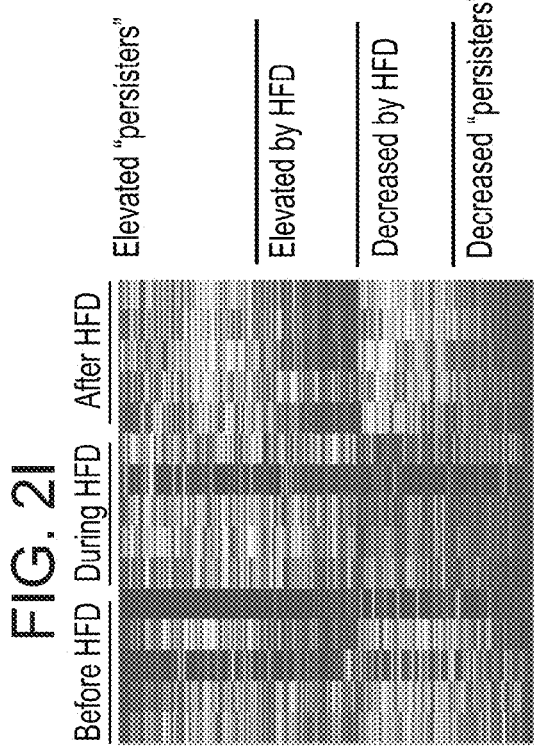
FIG. 2H
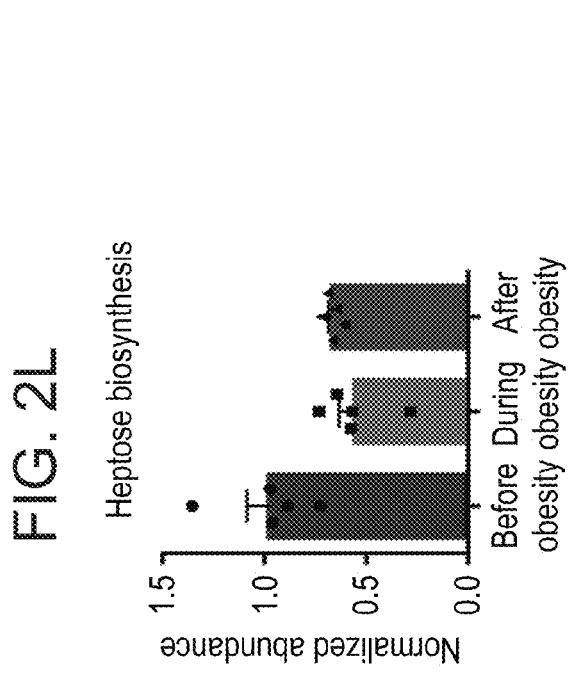
FIG. 2I
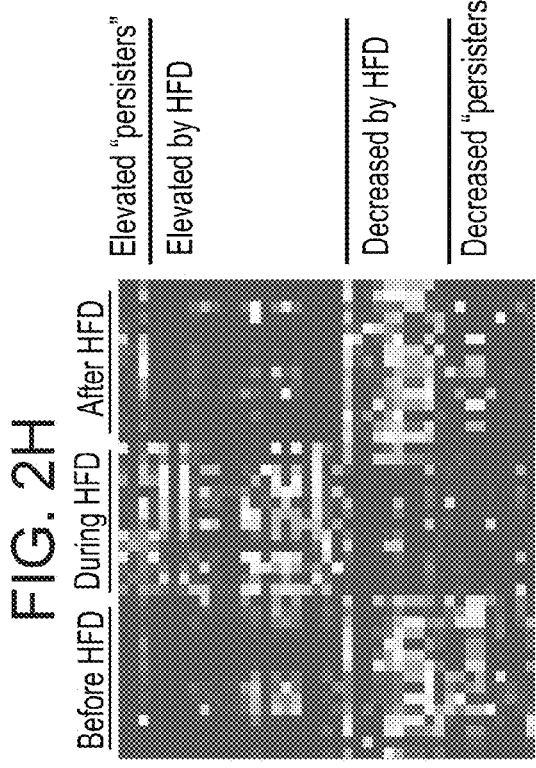
FIG. 2J
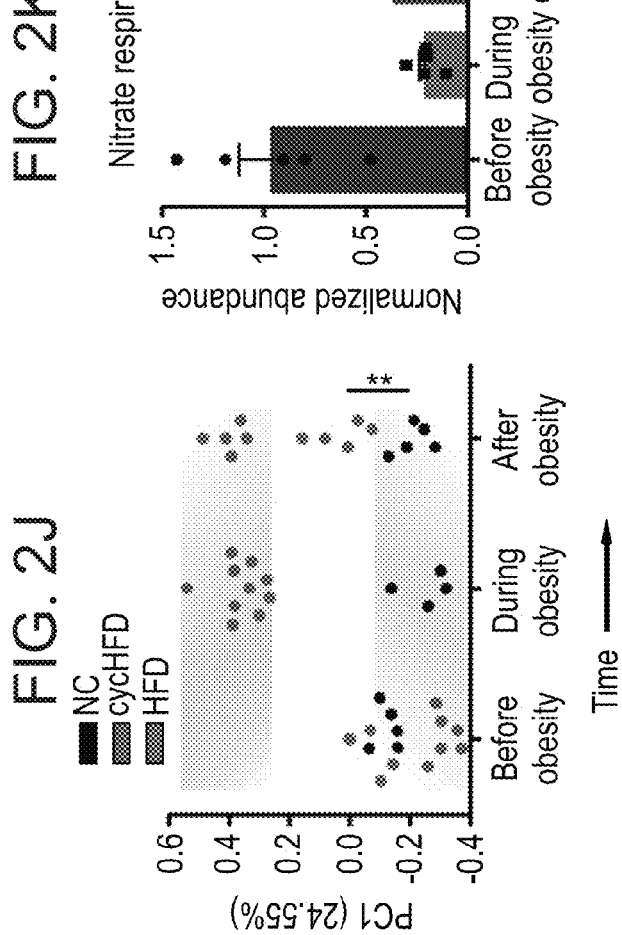
FIG. 2K
FIG. 2L

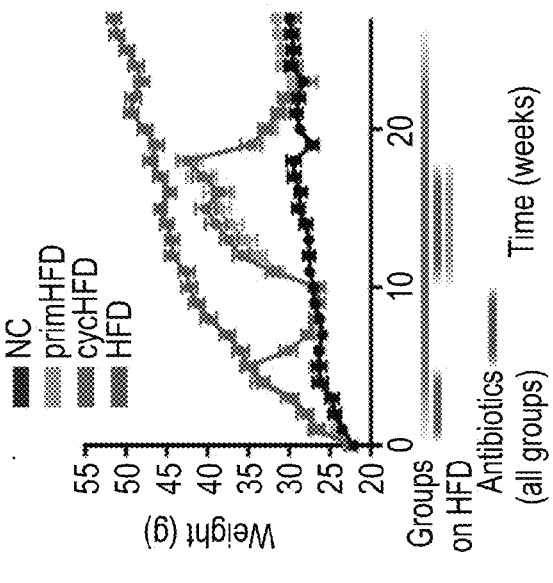
FIG. 3A
FIG. 3B
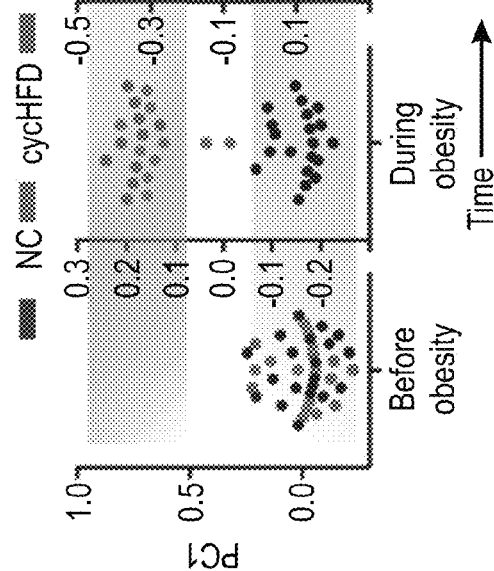
FIG. 3C
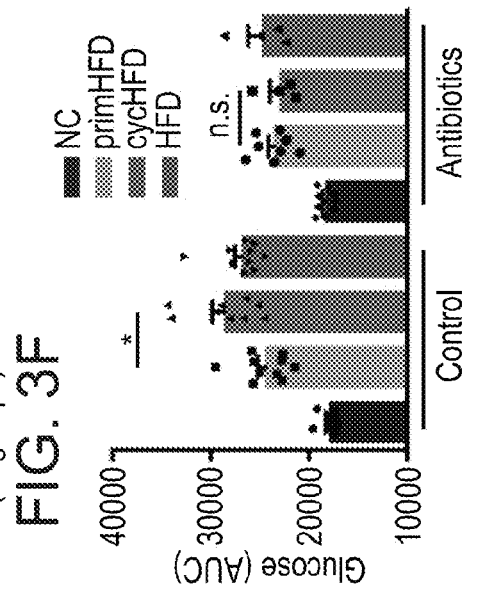
FIG. 3D
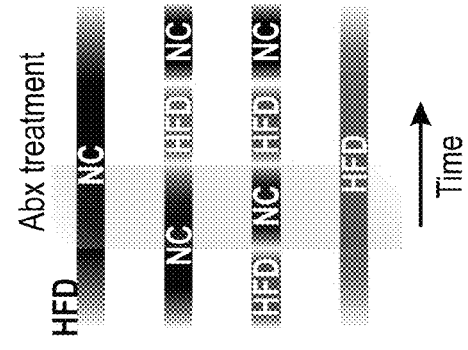
FIG. 3E
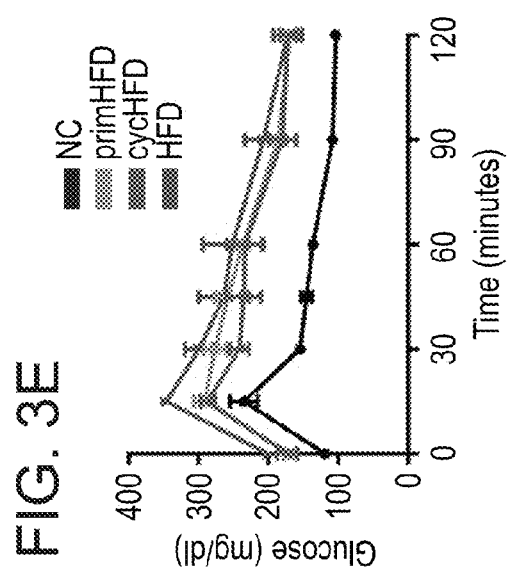
FIG. 3F
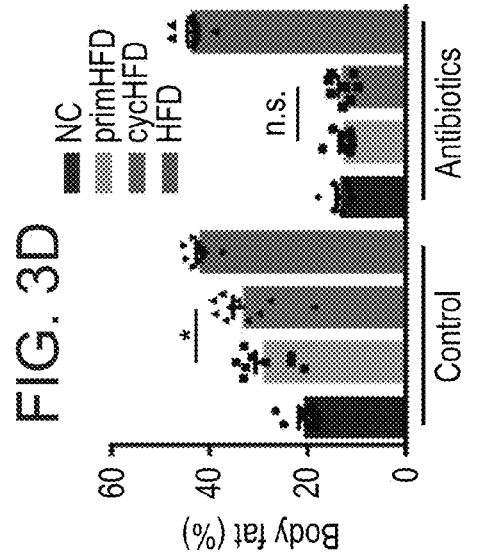

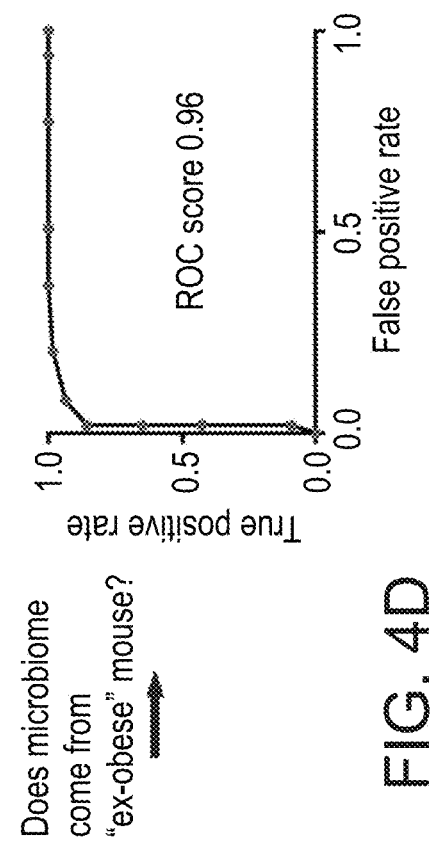
FIG. 4A
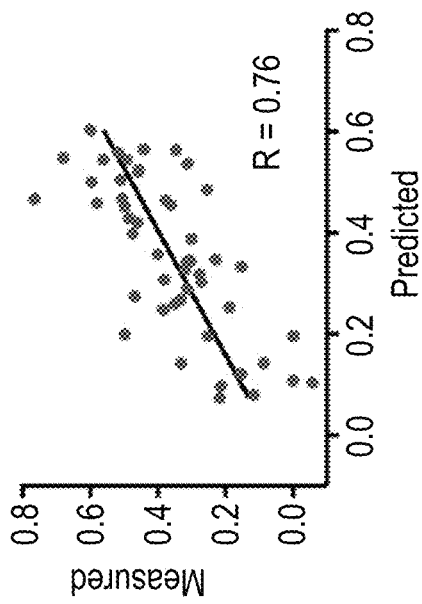
FIG. 4B Prediction of obesity history
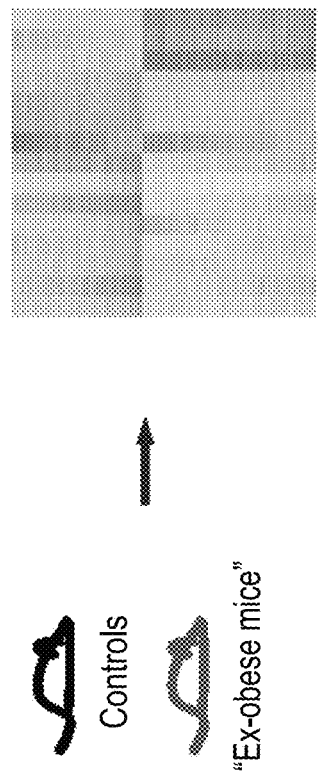
FIG. 4C 16S-based prediction of weight gain
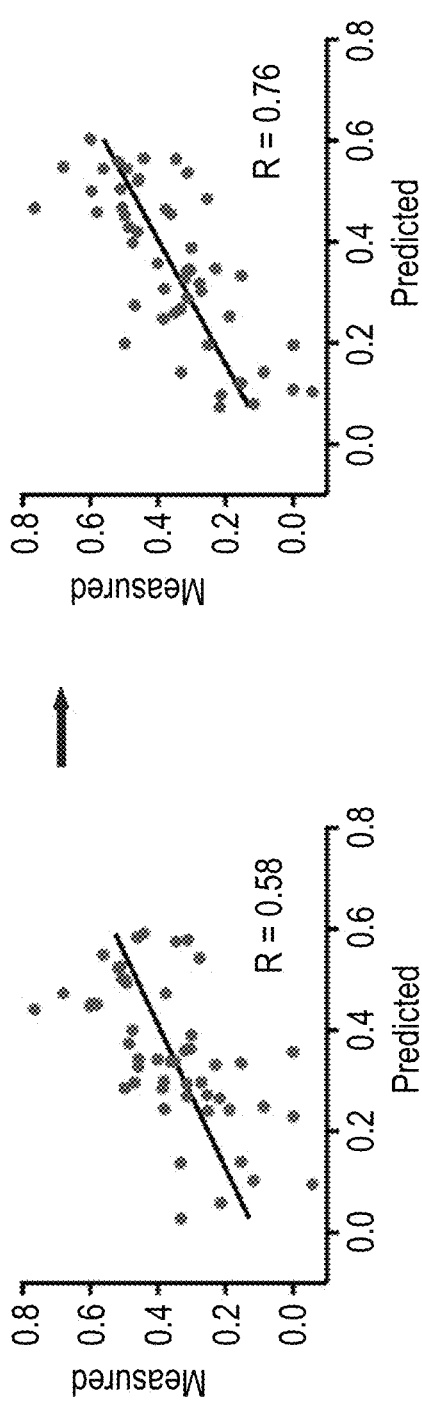
FIG. 4D Two-step prediction of weight gain

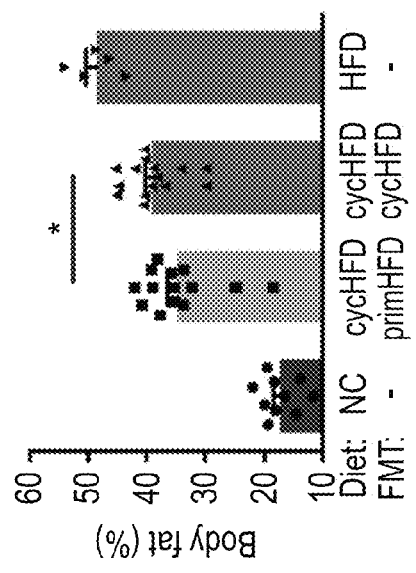
FIG. 5A
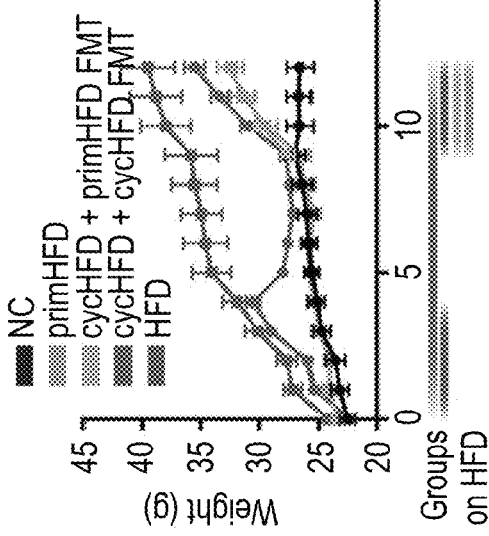
FIG. 5B
FIG. 5C
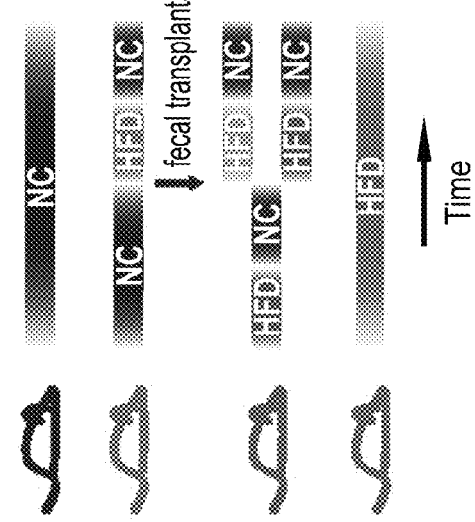
FIG. 5D
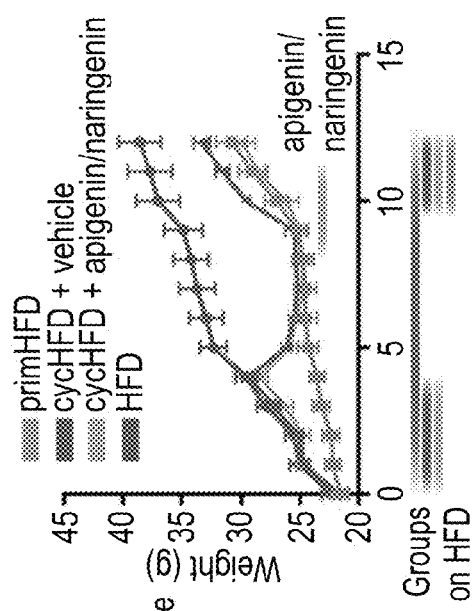
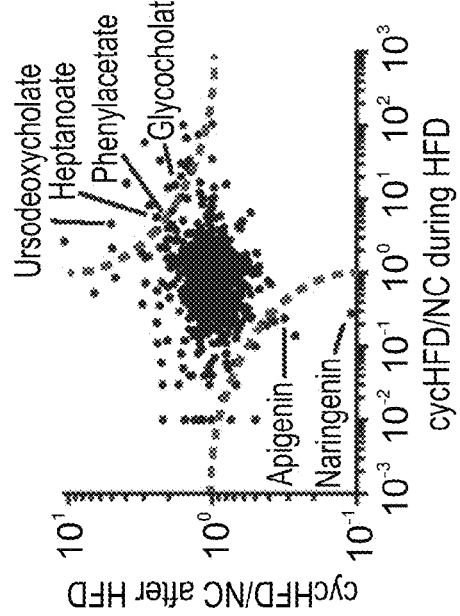
FIG. 5E
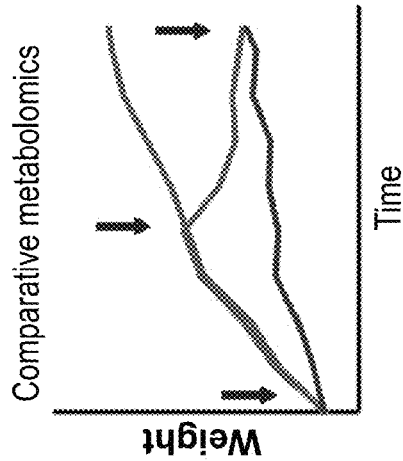
FIG. 5F

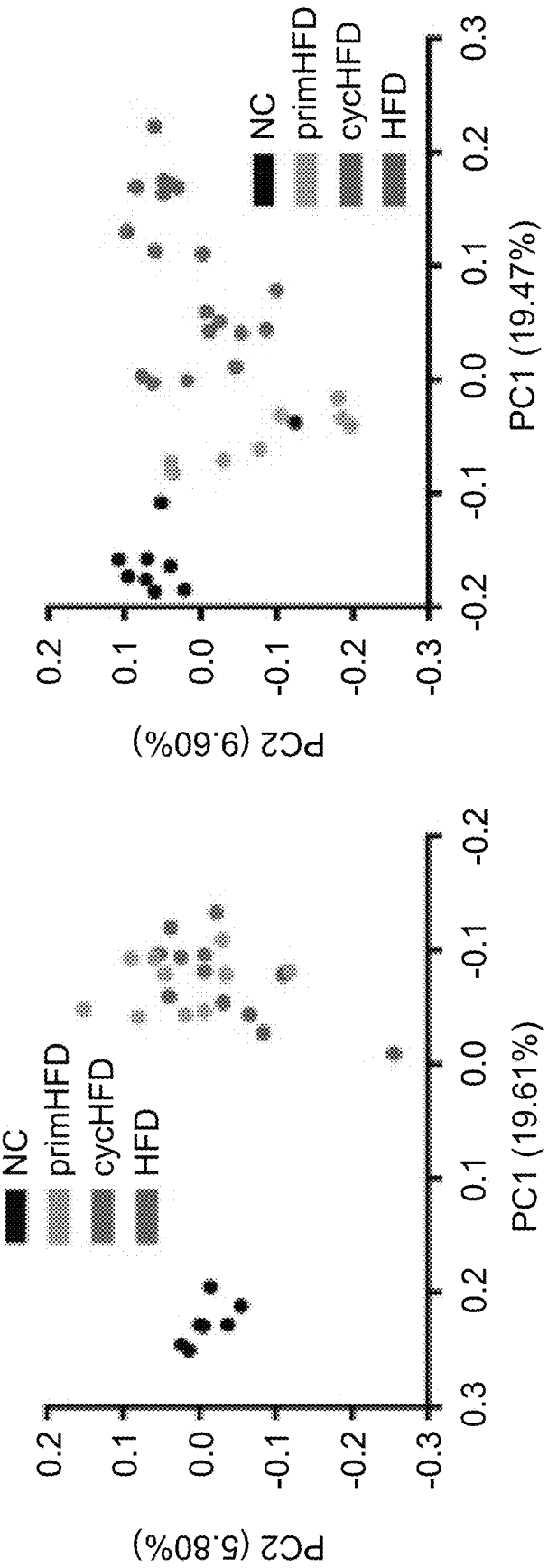

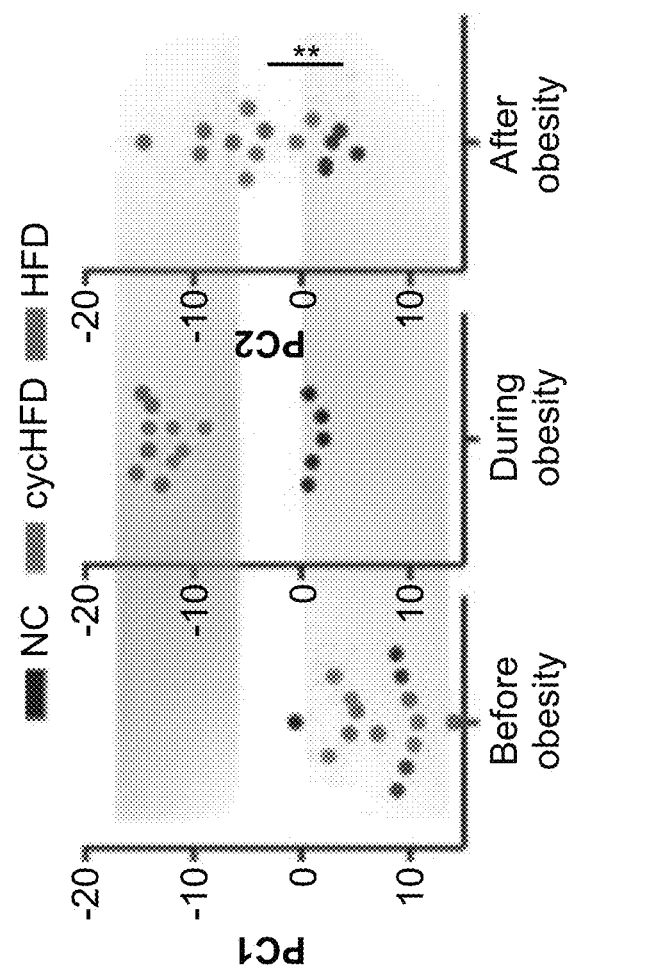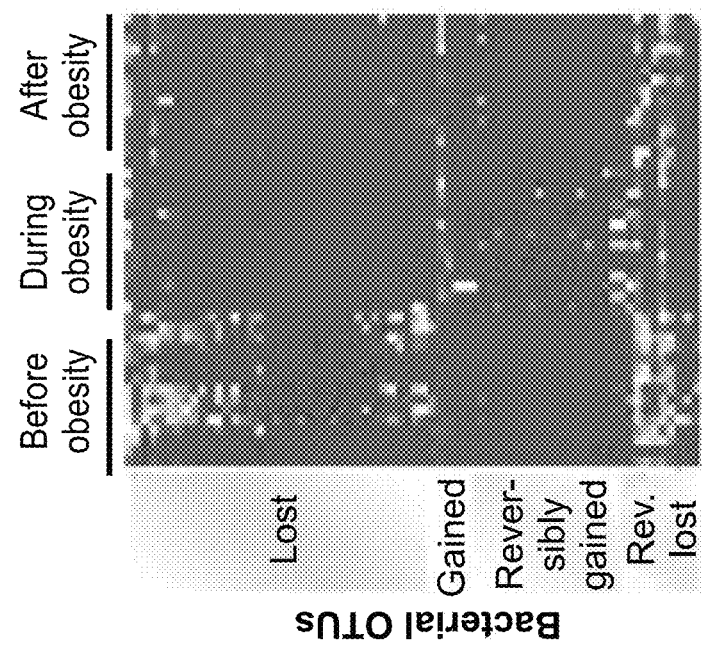

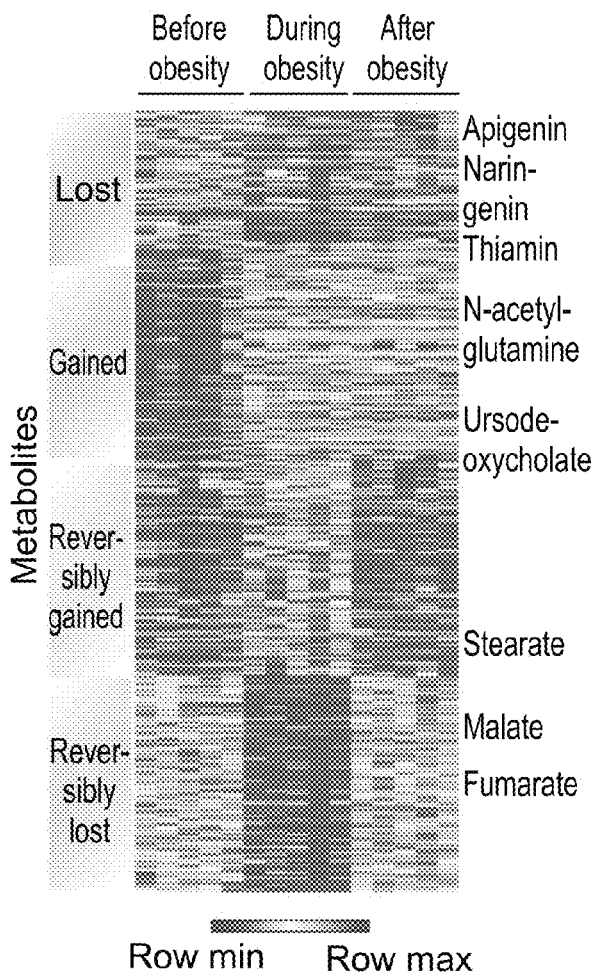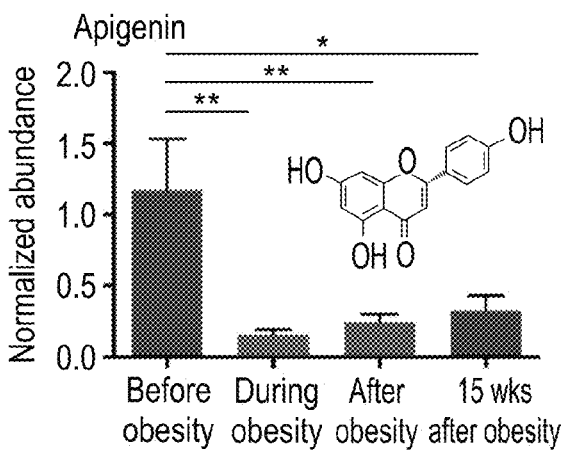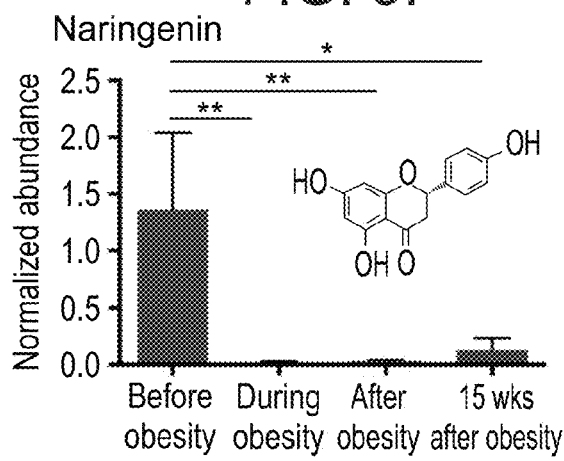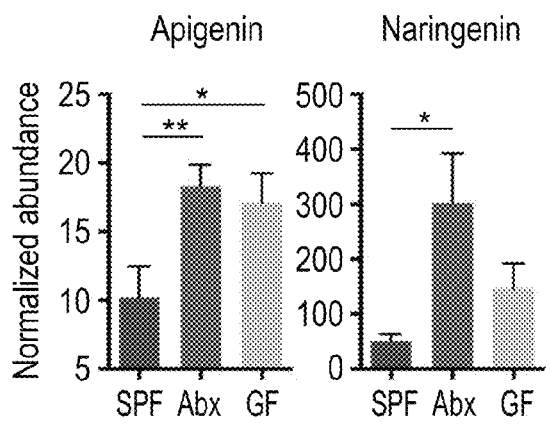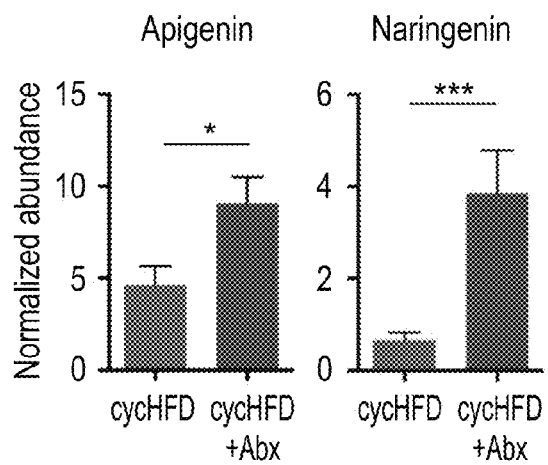

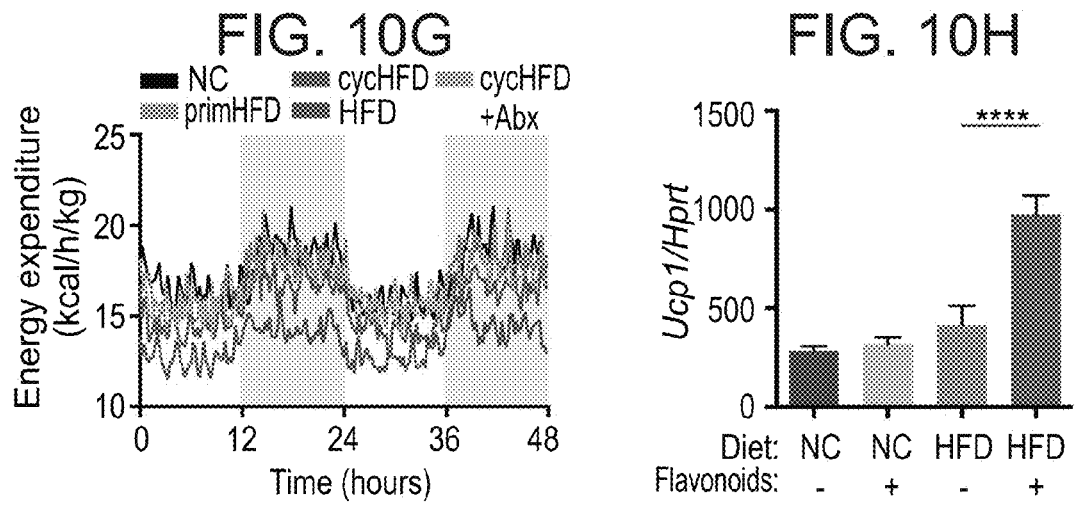
FIG. 10G
FIG. 10H
FIG. 10I
FIG. 10J
FIG. 10K
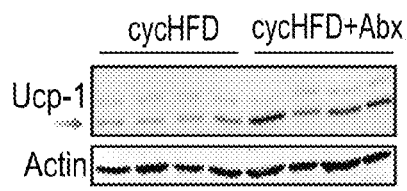
FIG. 10L
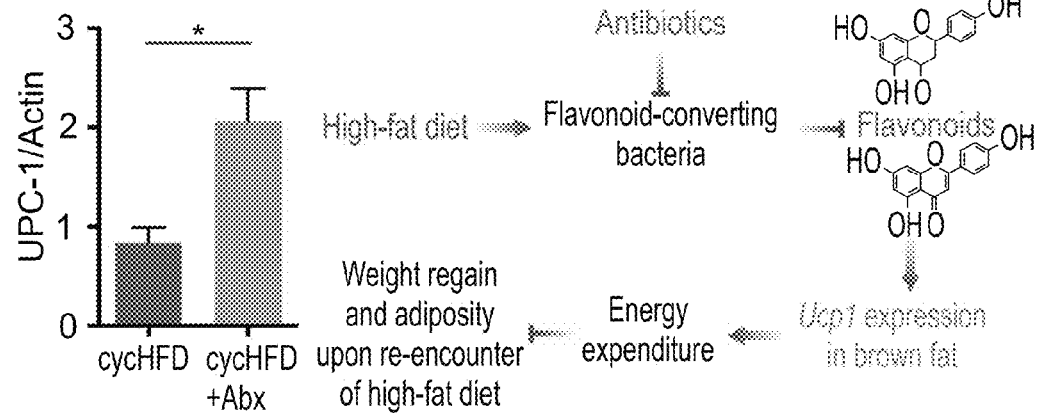
FIG. 10M
FIG. 10N

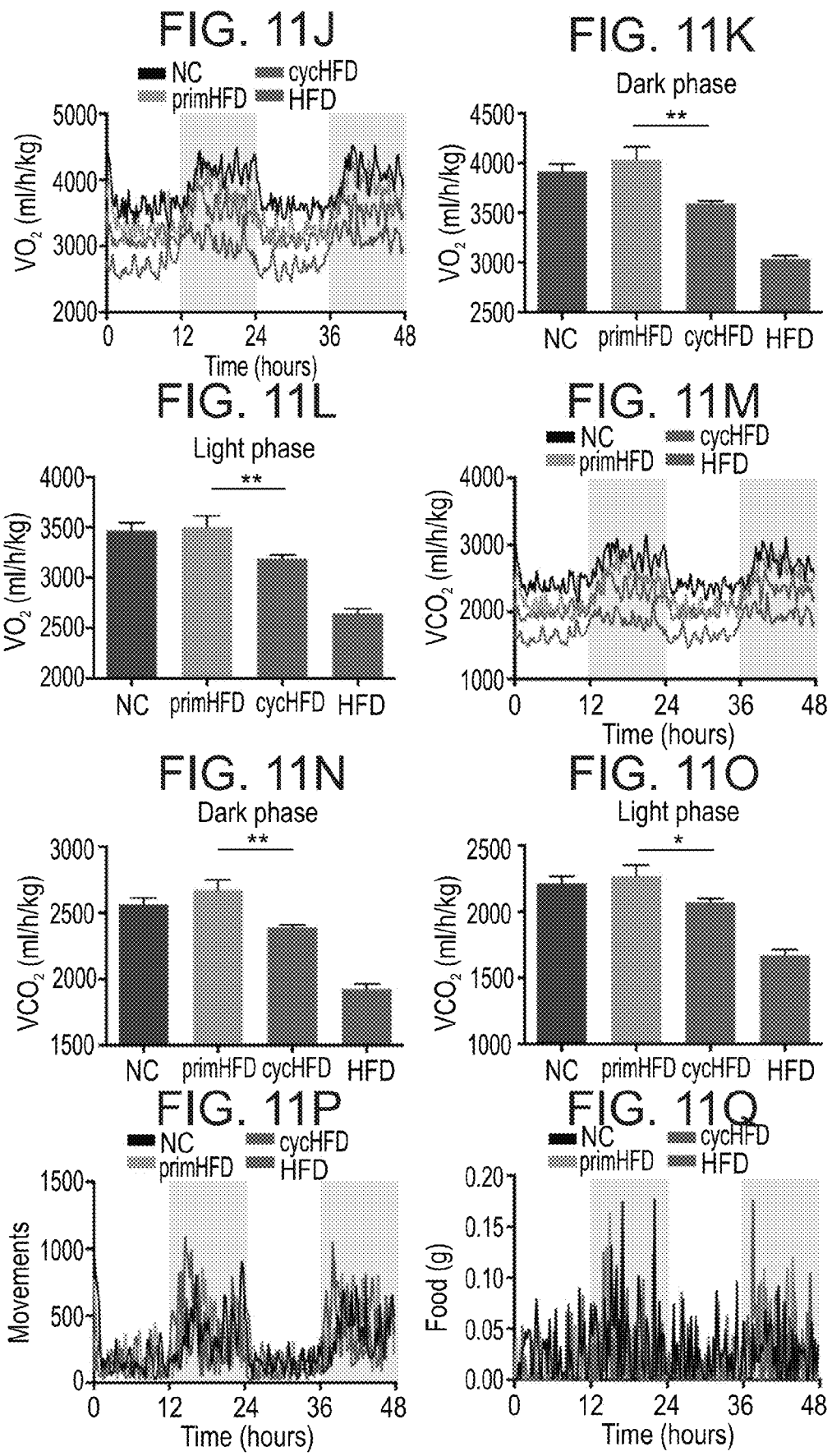

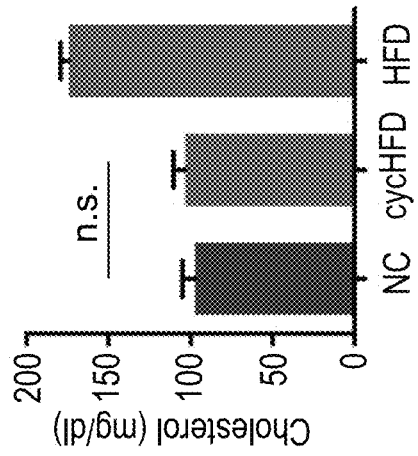
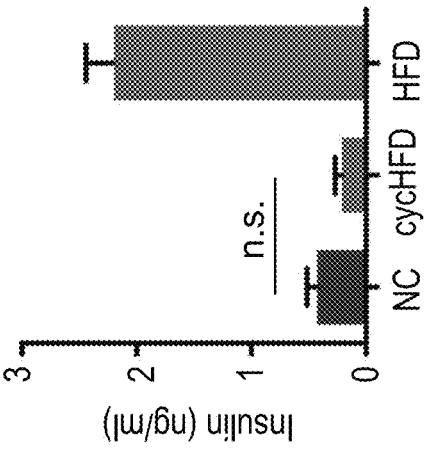
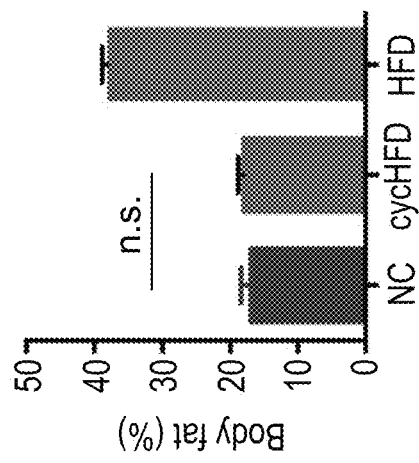
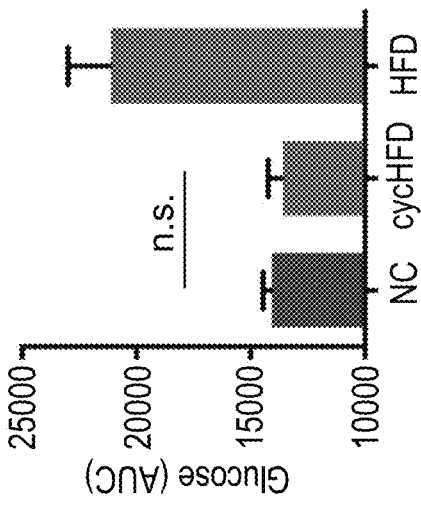
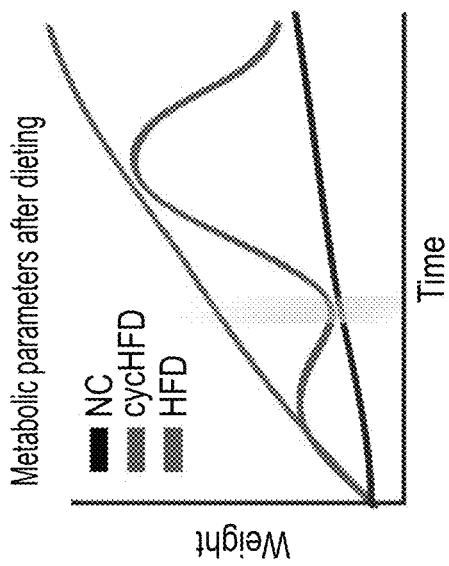
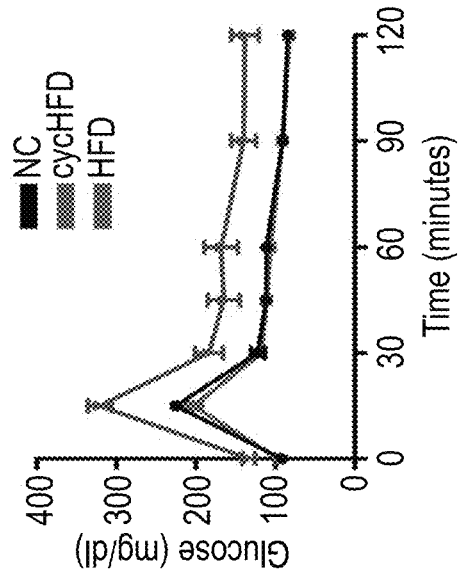

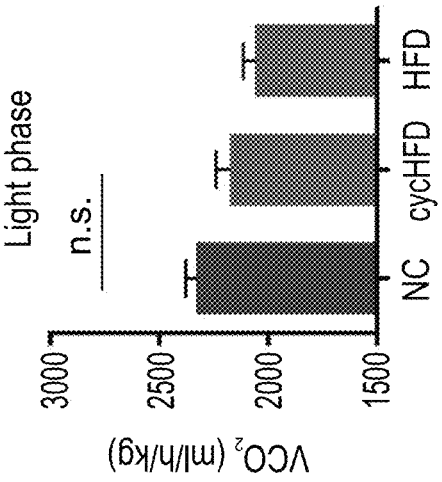
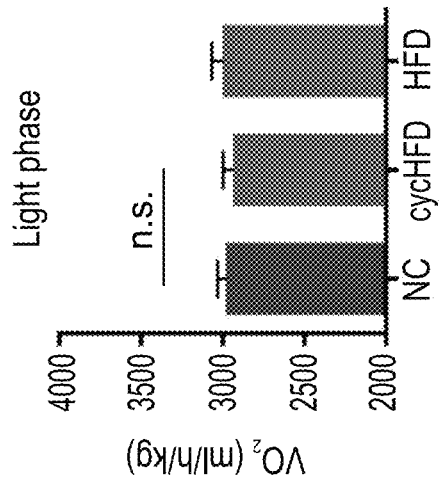
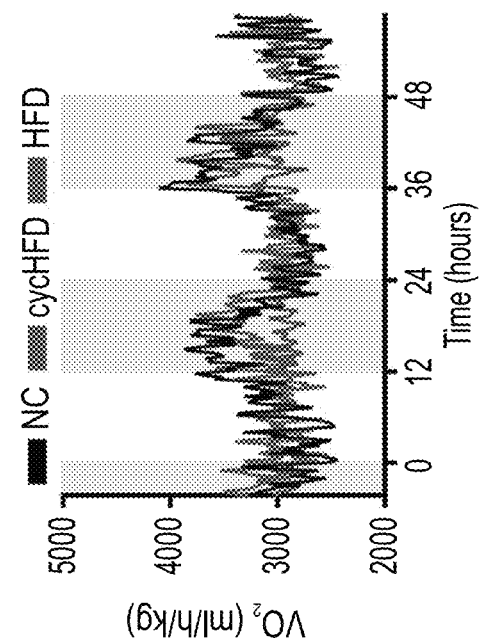
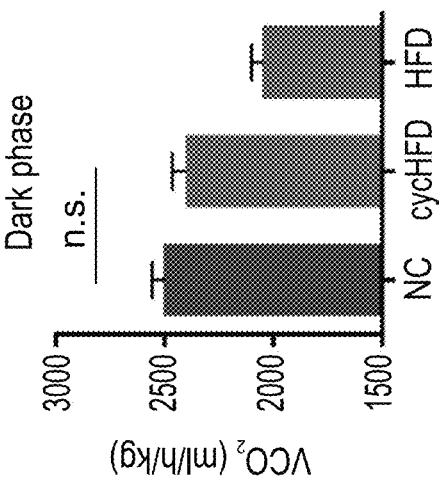
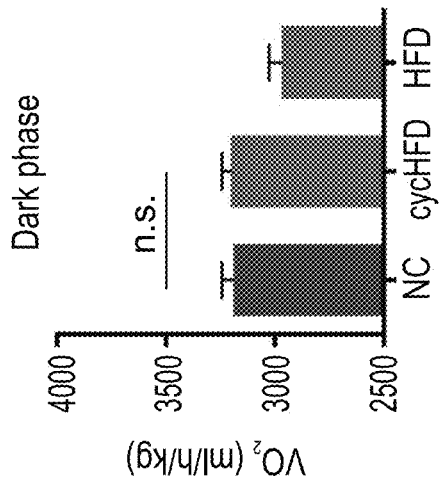
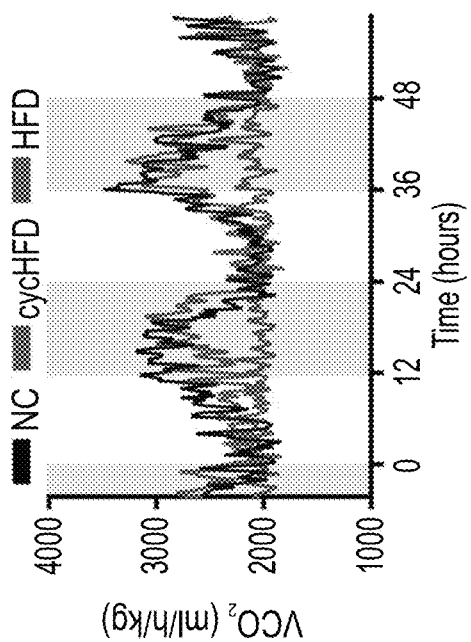

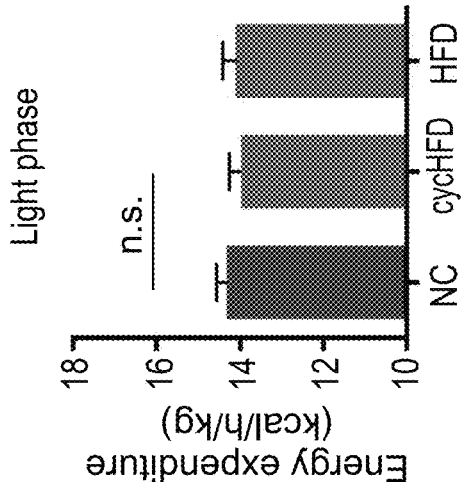
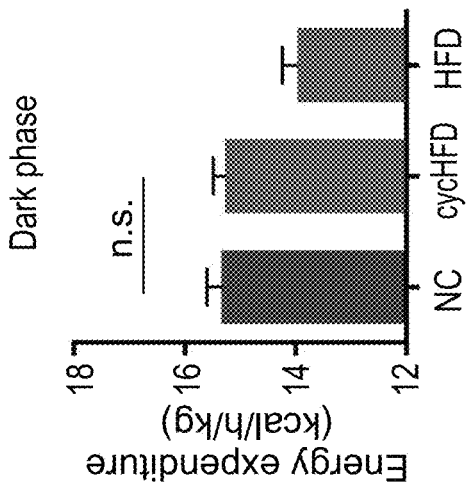
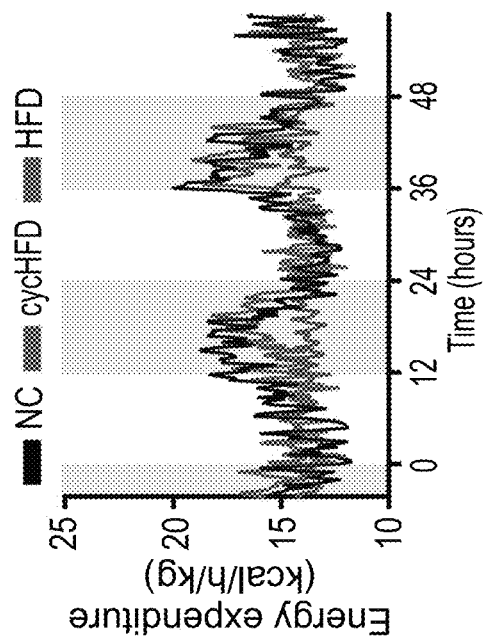
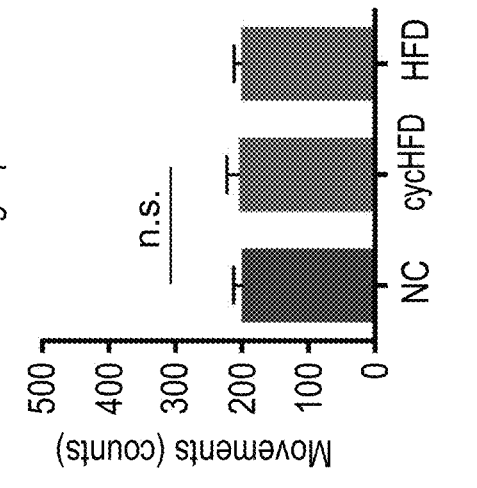
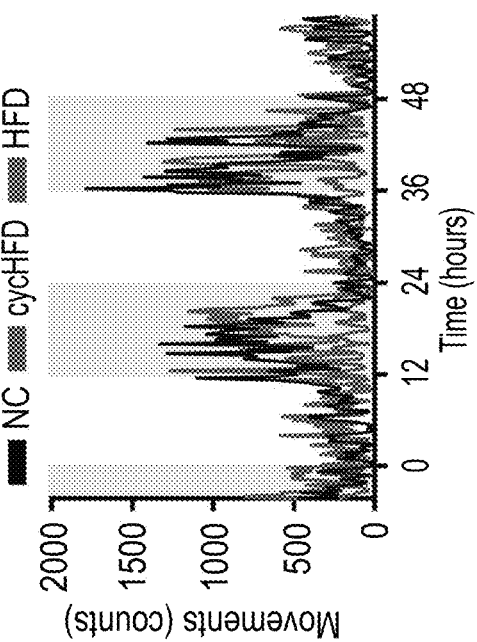

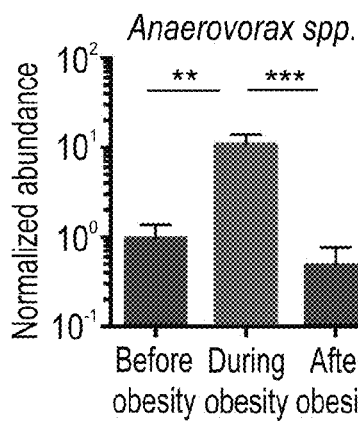
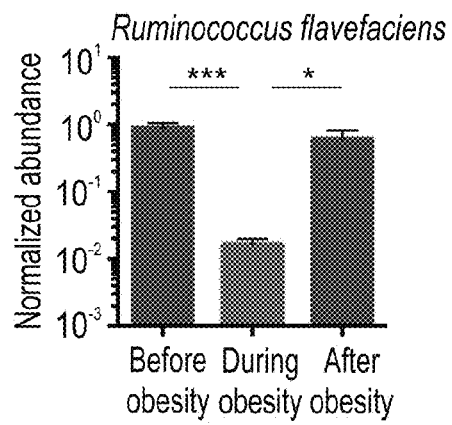
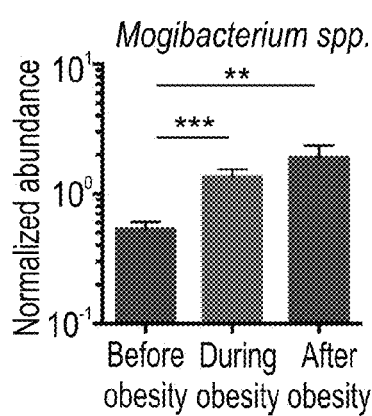
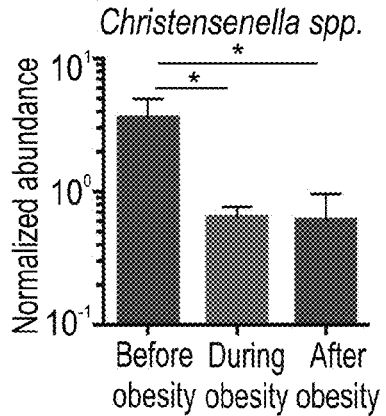
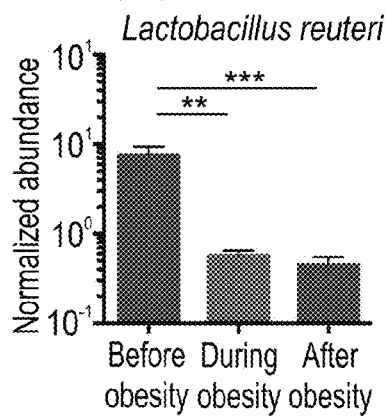
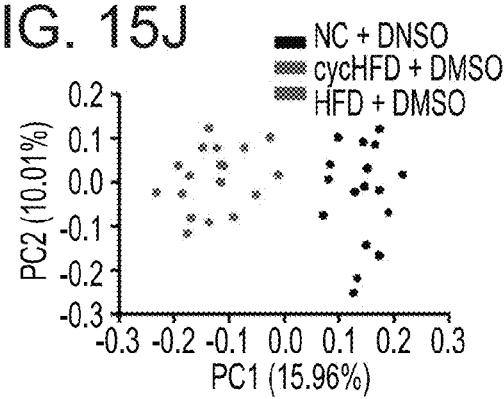
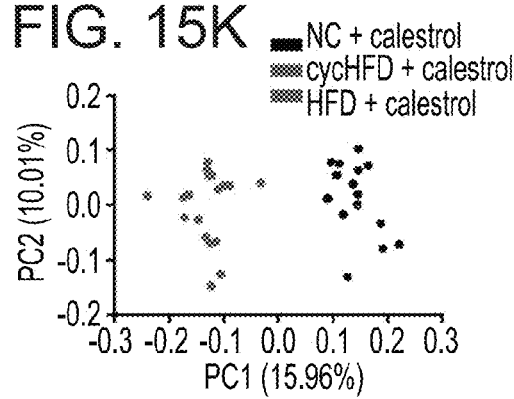
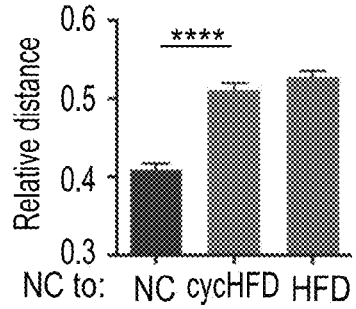
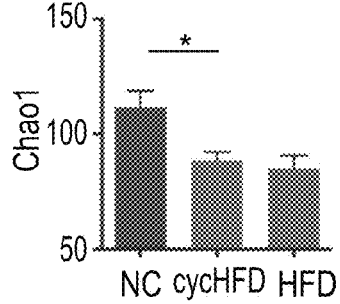

Flagellar assembly
Reversibly lost

DTT degradation

Fatty acid biosynthesis
Reversibly gained

N-Glycan biosynthesis

Isoflavonoid biosyntesis
Lost

Steroid biosynthesis

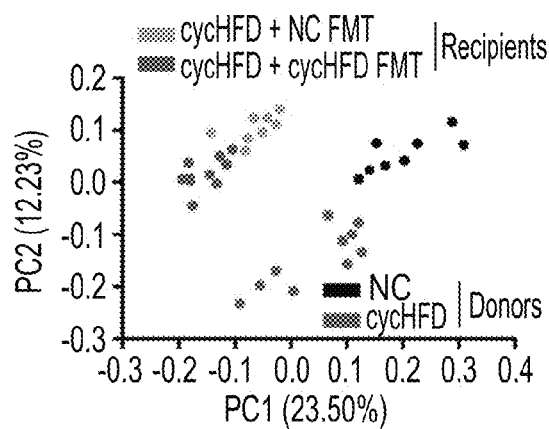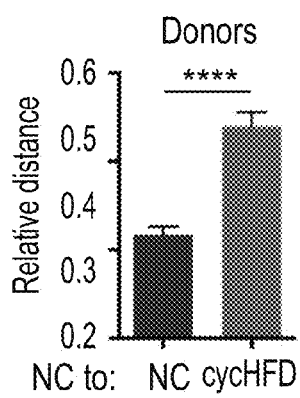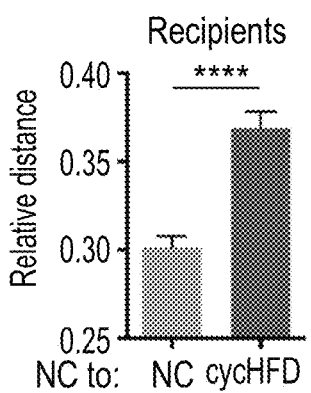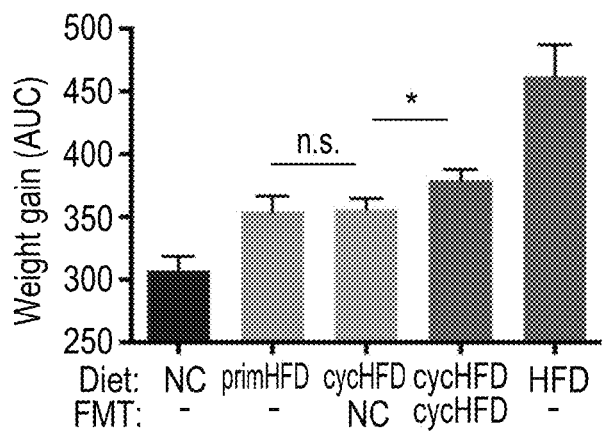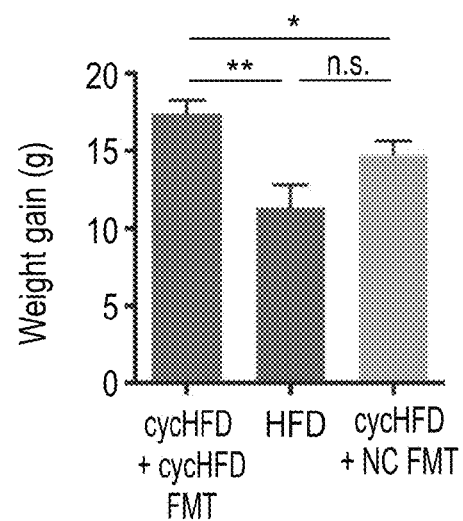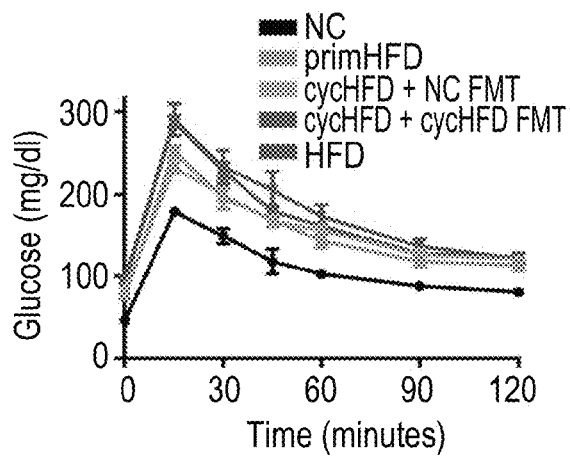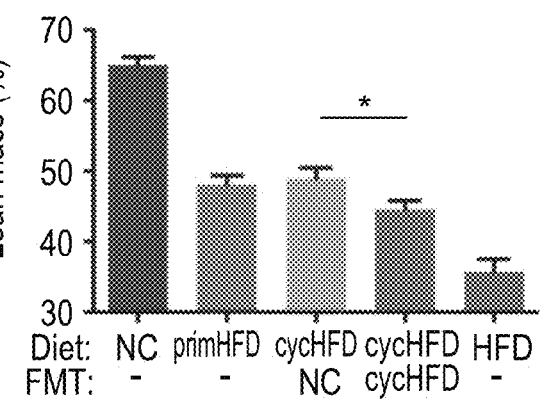

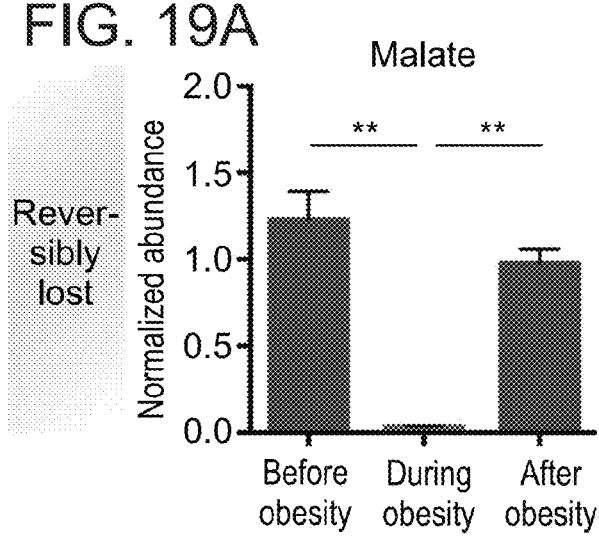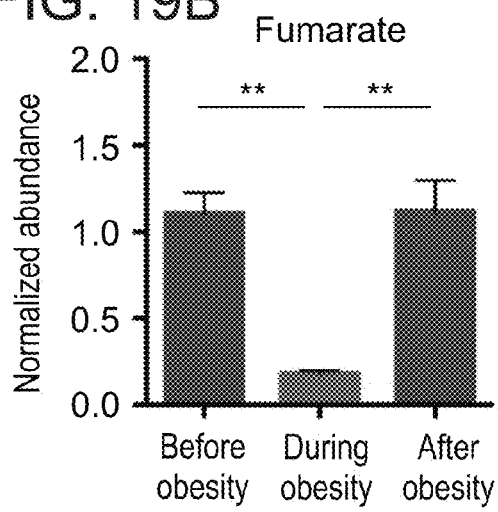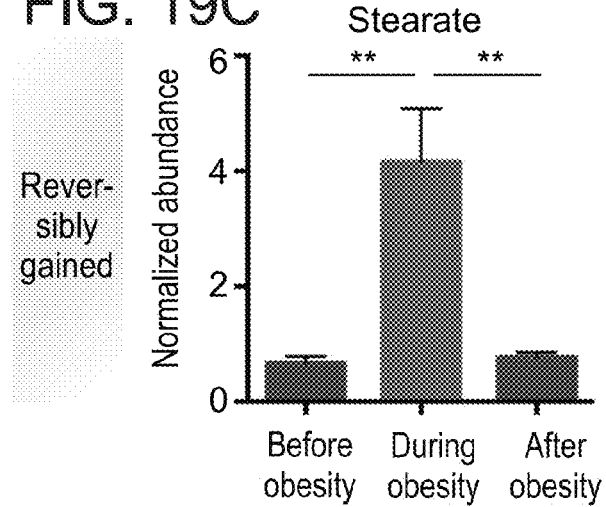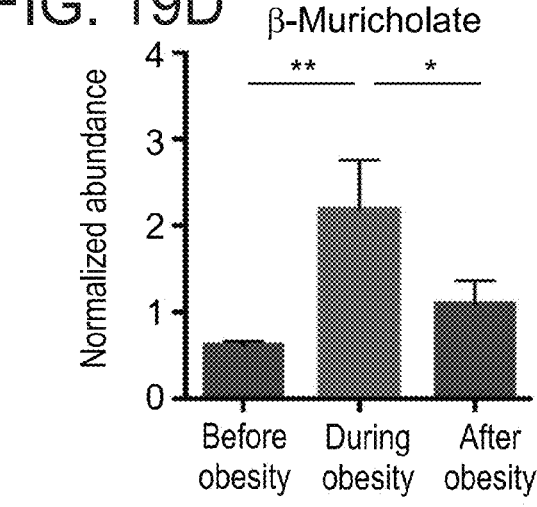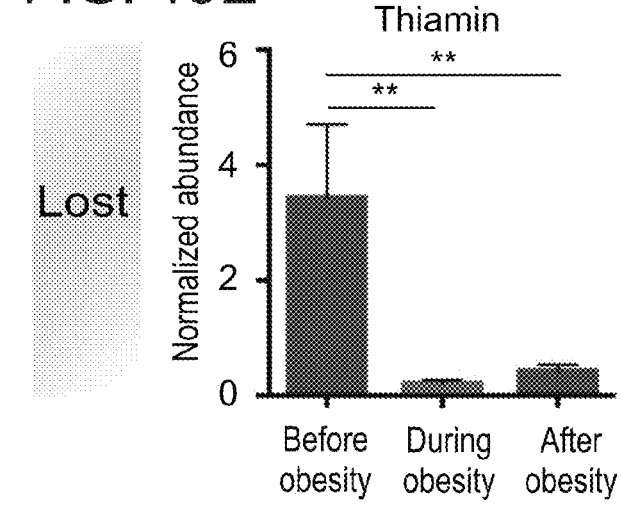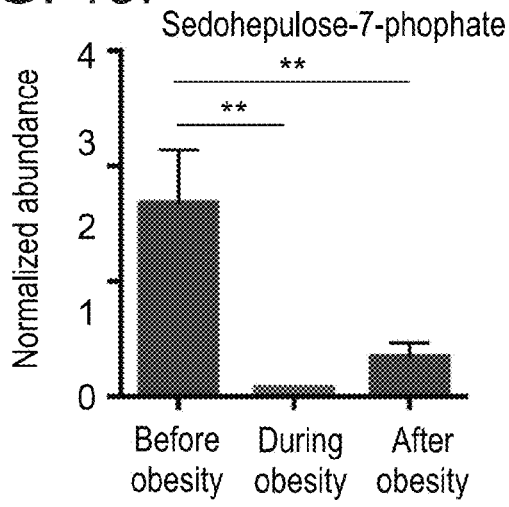

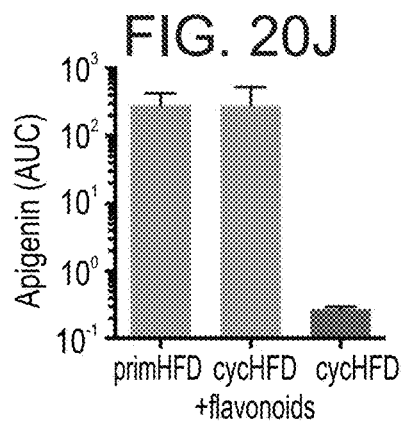
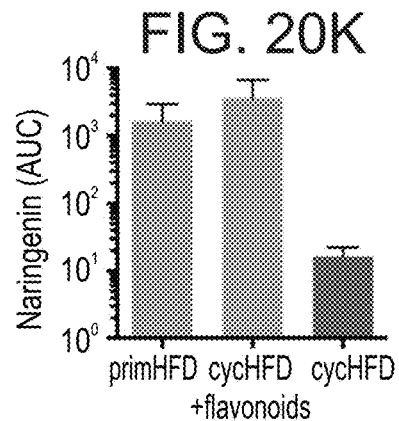
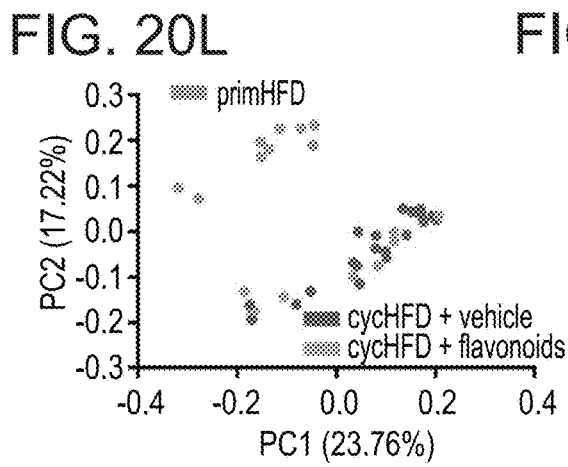
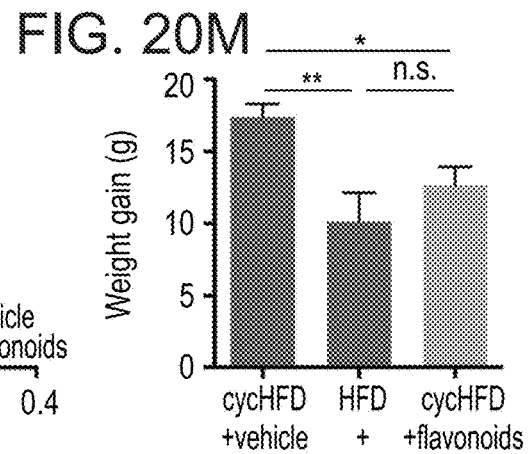
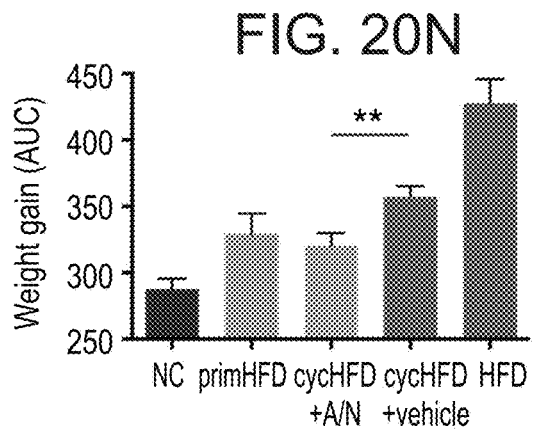
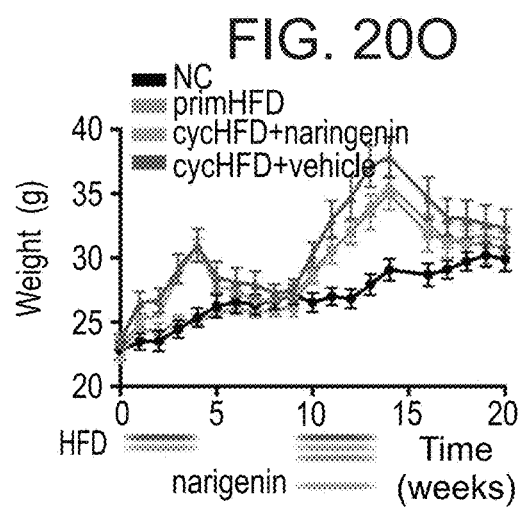
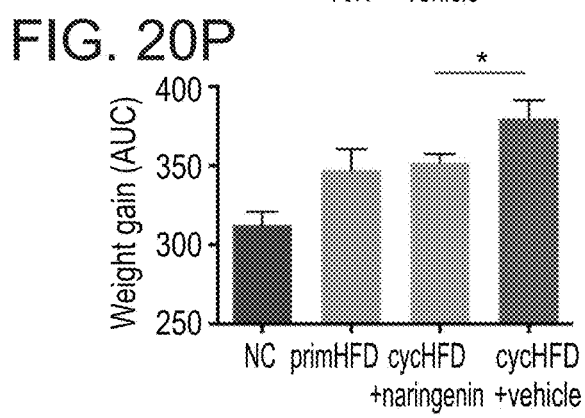

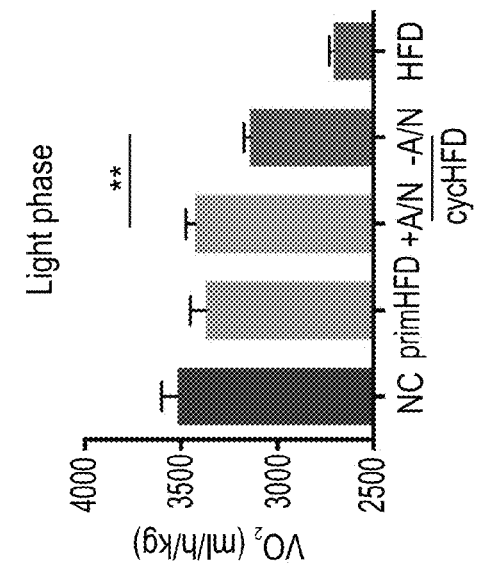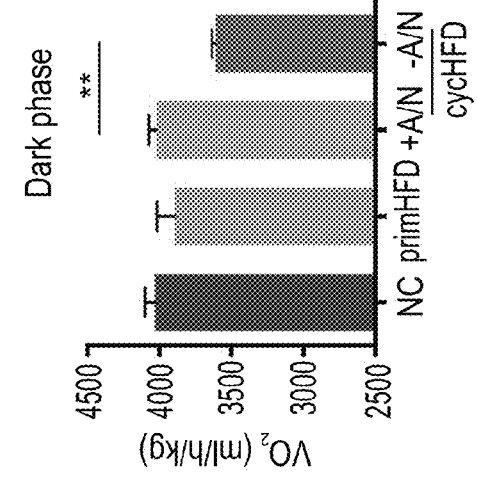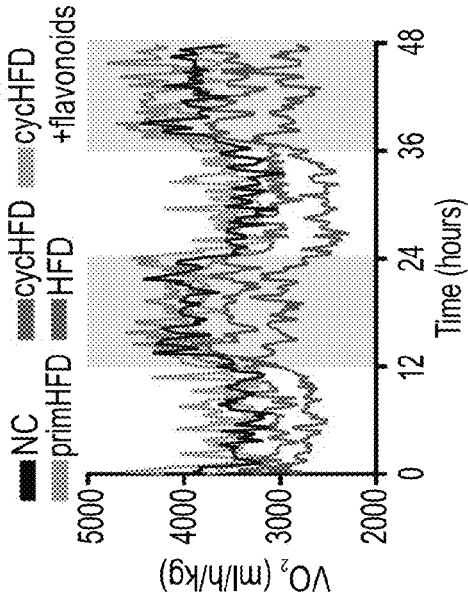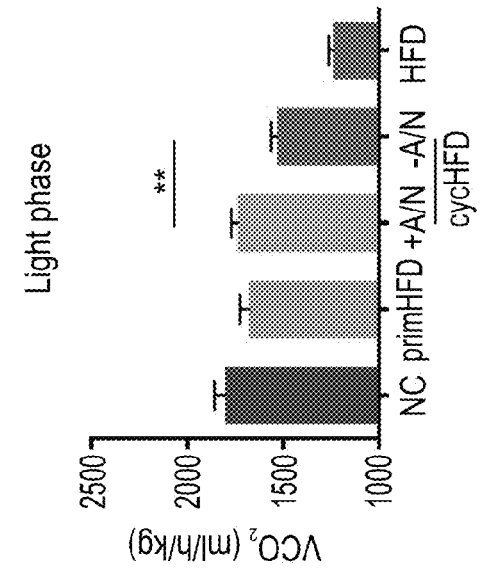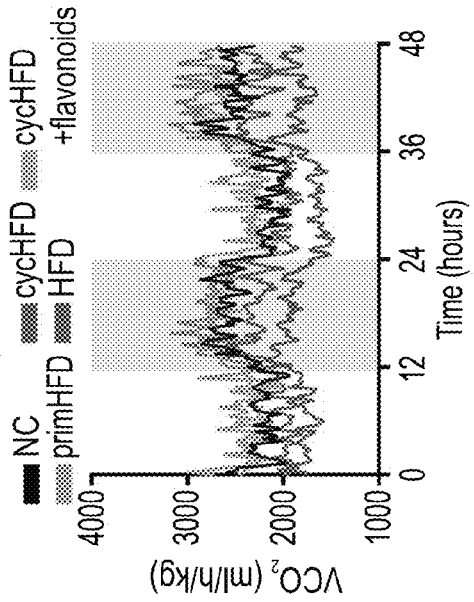

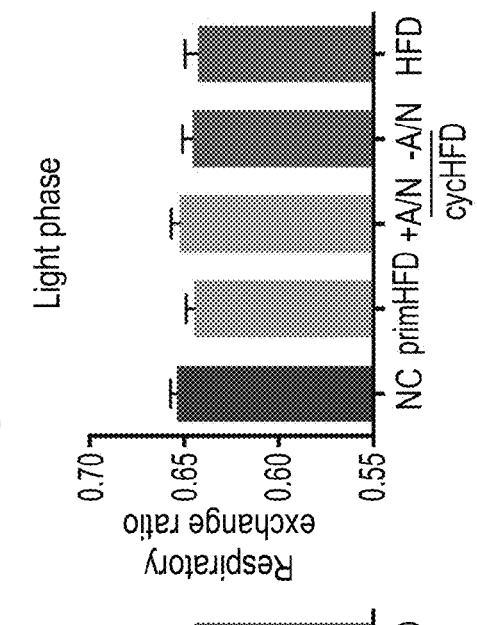
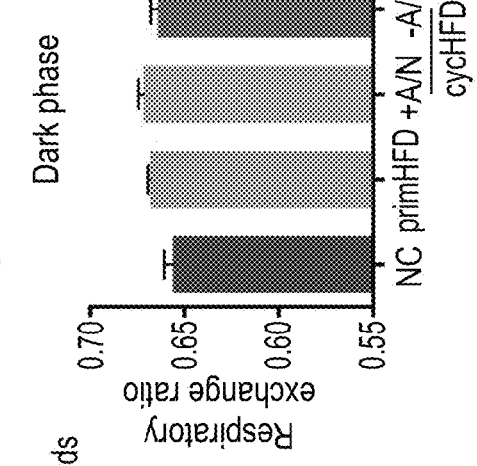
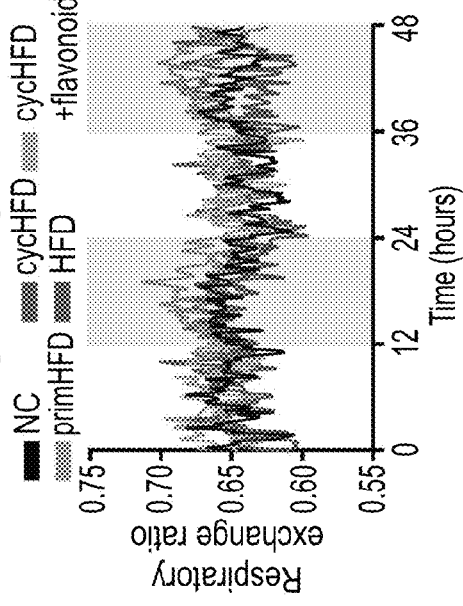
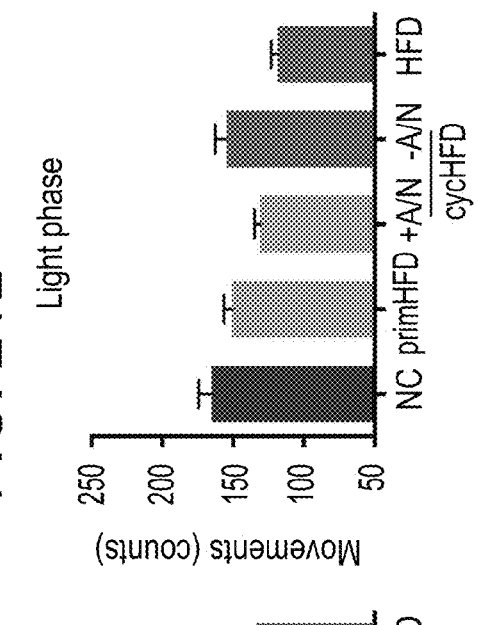
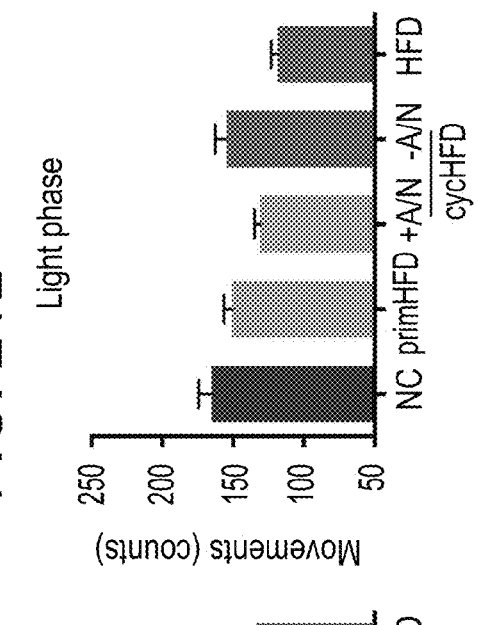
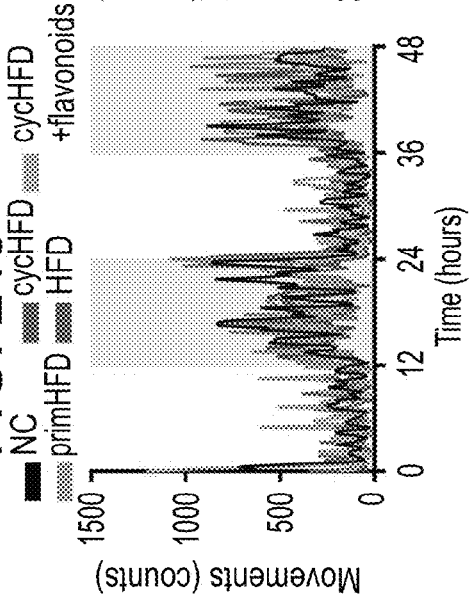

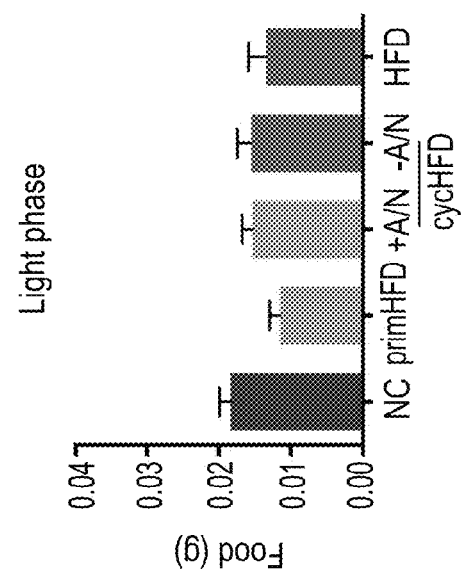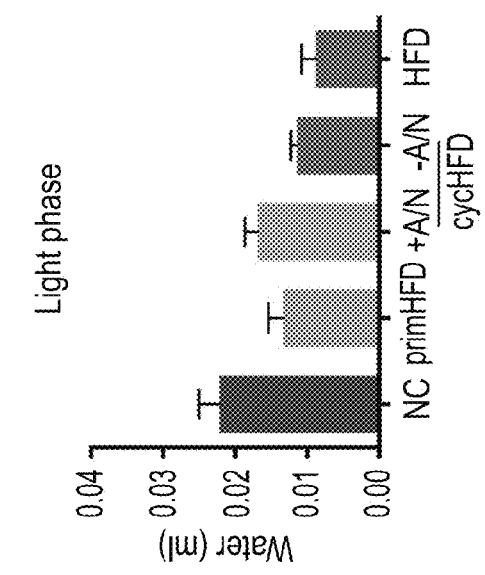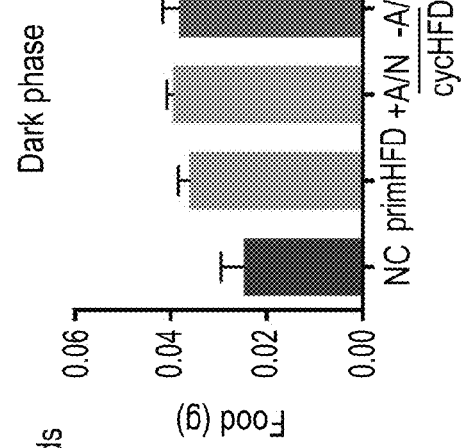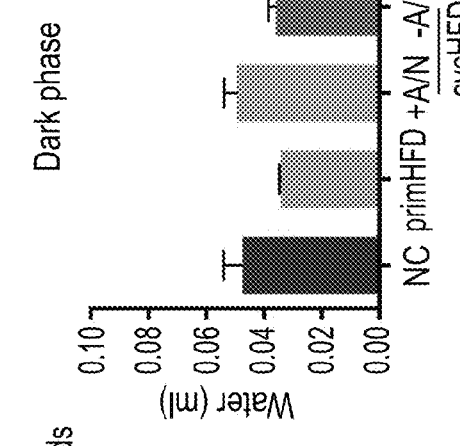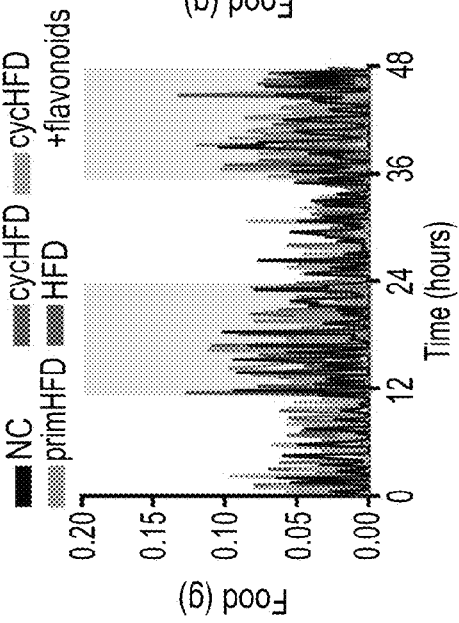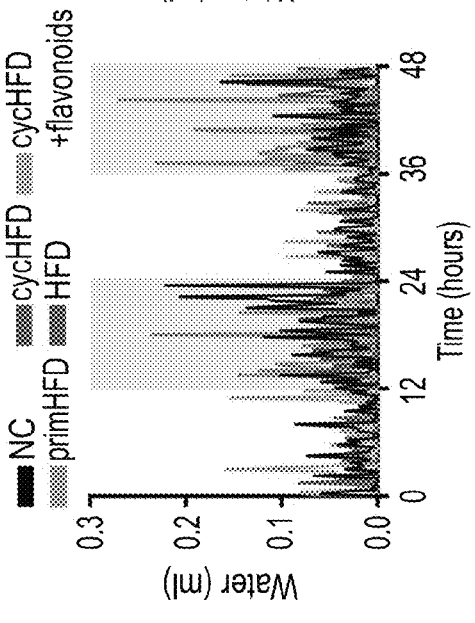

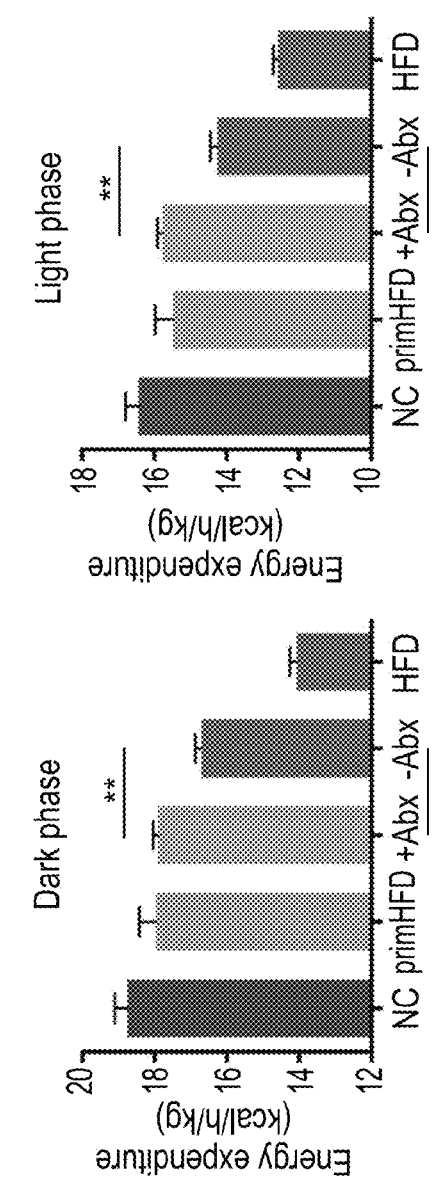
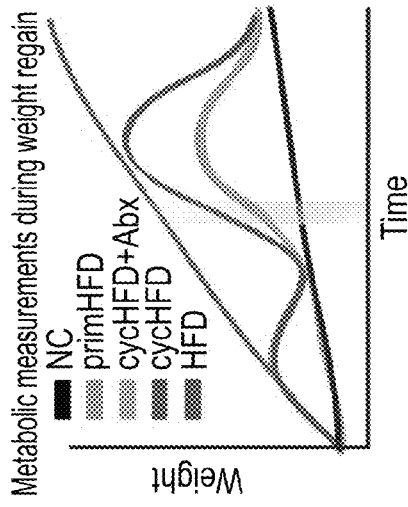
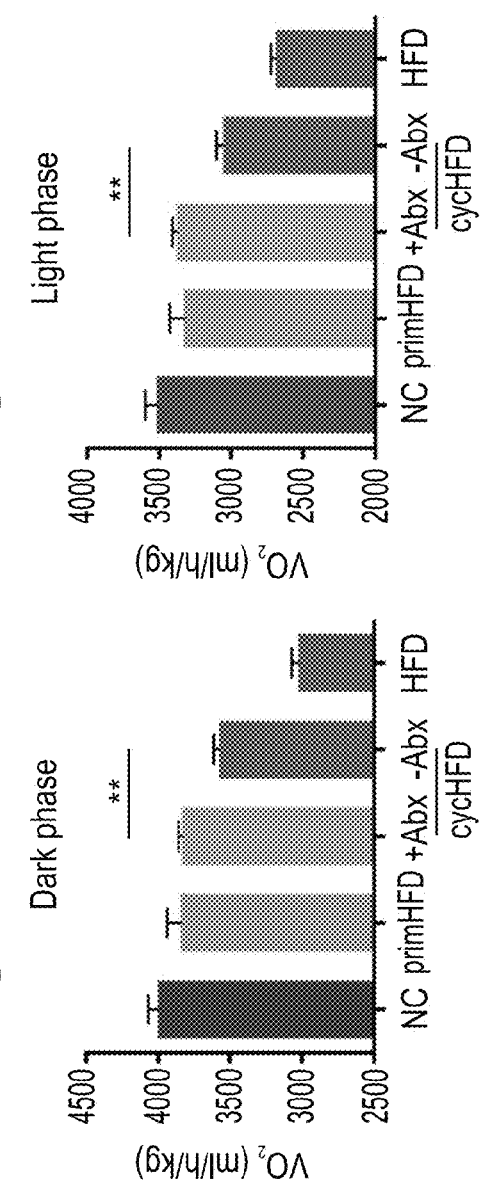
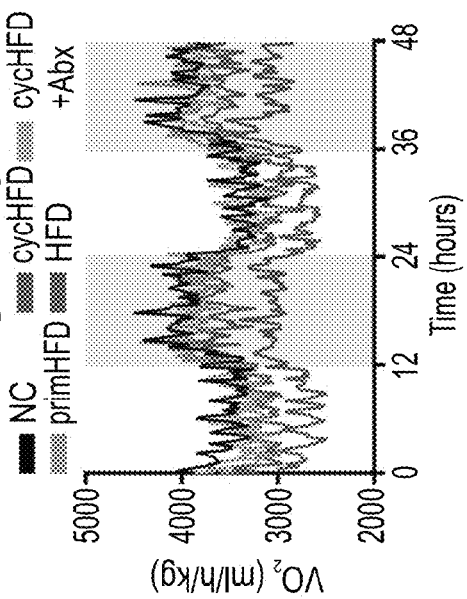

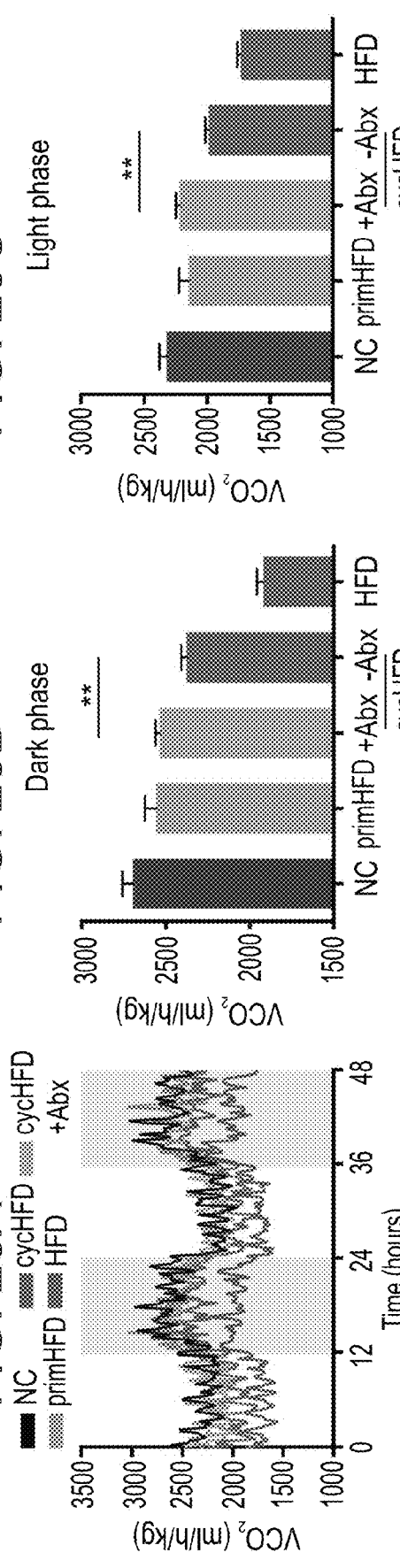
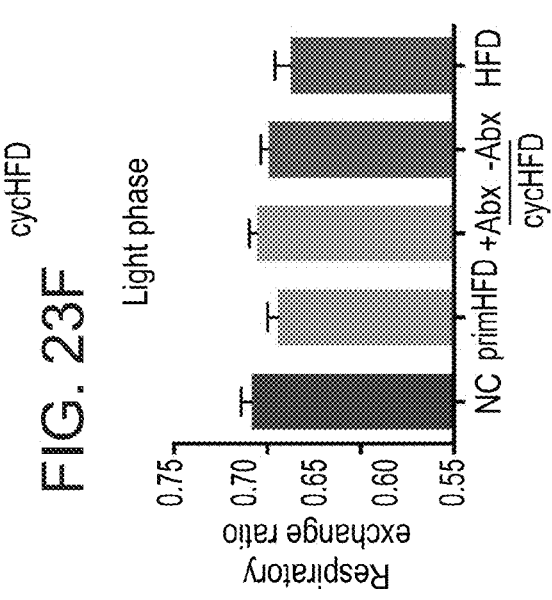

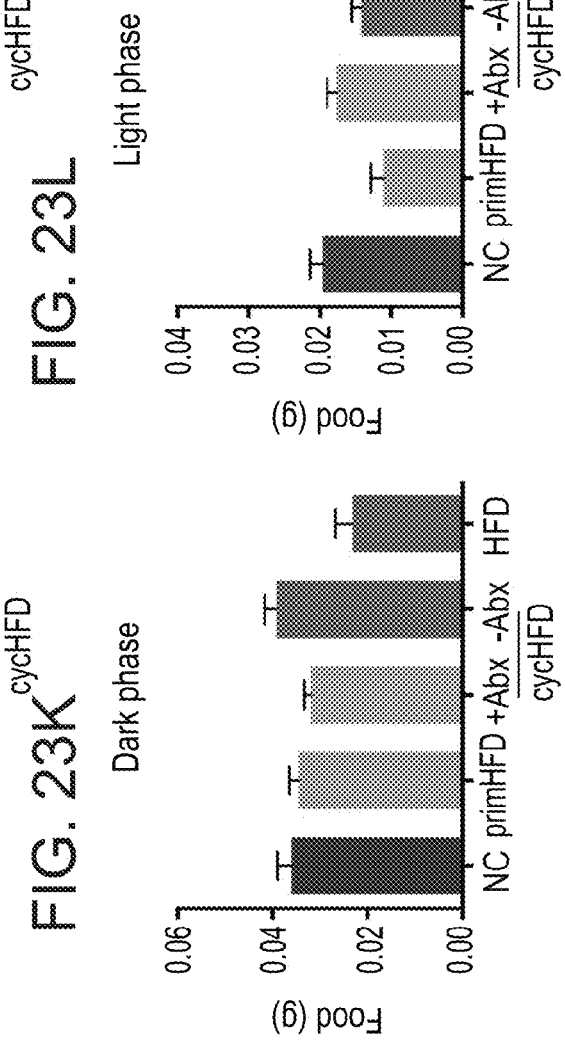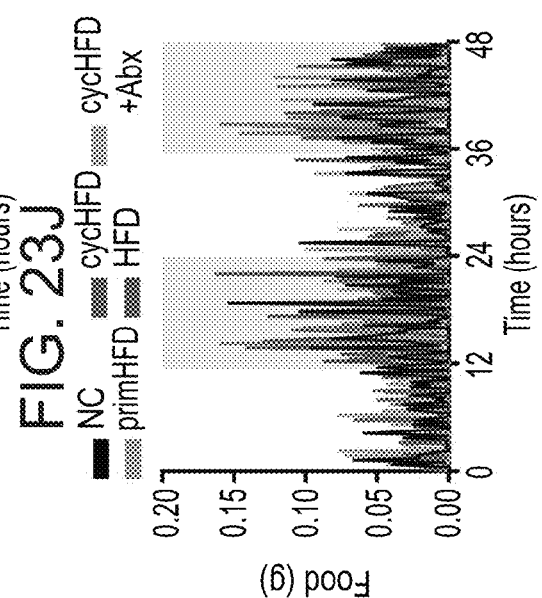

MICROBIOME-BASED DIAGNOSIS, PREDICTION AND TREATMENT OF RELAPSING OBESITY

RELATED APPLICATIONS

This application is a division of U.S. patent application Ser. No. 16/077,751 filed on Aug. 14, 2018, which is a National Phase of PCT Patent Application No. PCT/IL2017/050187 having International Filing Date of Feb. 14, 2017, which claims the benefit of priority under 35 USC § 119(e) of U.S. Provisional Patent Application Nos. 62/423,299 filed on Nov. 17, 2016 and 62/295,094 filed on Feb. 14, 2016. The contents of the above applications are all incorporated by reference as if fully set forth herein in their entirety.

SEQUENCE LISTING STATEMENT

The ASCII file, entitled 87799SequenceListing.txt, created on May 12, 2021, comprising 863 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to microbiome based methods of maintaining a target body weight and analyzing the likelihood of weight regain following a diet.

The past century has witnessed an alarming increase in the prevalence of obesity, with currently more than 44% of the adult world population estimated to be overweight, and over 300 million adults suffering from morbid obesity. In addition to its epidemic proportions, obesity is considered a major risk factor for a number of closely associated diseases, including type II diabetes mellitus affecting close to 500 million people worldwide, non-alcoholic fatty liver disease emerging as the most common liver disease in the developed world, and ischemic cardiovascular disease considered the leading cause of overall mortality. Collectively, the global obesity endemic has far-reaching consequences on life expectancy, quality of life, and healthcare costs.

Despite a continuous worldwide medical and scientific effort, no medical intervention to date has been consistently shown to have long-lasting effects in reversing the obesity epidemic. A plethora of dietary approaches have been claimed to efficiently induce a significant weight reducing effects, yet the vast majority of these have proven to be non-efficacious over prolonged period of time, or incompatible with long-term compliance. Moreover, in more than 80% of cases in which weight loss was initially successful, the reduced weight is not maintained, and instead followed by recurrent weight gain and relapsing metabolic complications within 12 months of initial weight reduction that exceeded the pre-dieting metabolic derangements. The post-dieting weight gain is not genetically driven, as exemplified in a large-scale twin study demonstrating a significant tendency to weight gain in dieting twins (some monozygotic) as compared to their non dieting sibling. This risk was further enhanced with each weight gain-dieting cycle. The exaggerated post-dieting weight gain was independent of starting weight, as noted by a study demonstrating that non-dieting teenagers featured half the risk to develop obesity as compared to dieting teens featuring an indistinguishable starting weight. Likewise, obesity relapse was suggested to be exercise-independent, as weight cycling predicted subsequent weight gain even in a group of 1800 highly active athletes. Thus, the mechanisms underlying the weight cycling-induced obesity phenomenon, commonly referred to as the 'yo-yo effect', remain mostly unknown.

An emerging and previously unappreciated factor affecting human metabolic homeostasis and the risk for obesity and its metabolic complications is the intestinal microbiome. Compositional and functional microbiome alterations, termed dysbiosis, have been shown in both animal models and humans to drive the tendency for obesity and its complications (7, 8). Moreover, dietary changes have been shown to be a central driver of microbiome composition and function, with dietary alterations significantly impacting the microbiome within days of initiation (9, 10).

SUMMARY OF THE INVENTION

According to an aspect of some embodiments of the present invention there is provided a method of analyzing the likelihood of weight regain in a subject who has reached a target weight by practicing a weight loss program, the method comprising determining an amount or presence of at least one microbe and/or product thereof in the gut microbiome of the subject, wherein the amount of the at least one microbe is altered during a prior weight gain period of the subject to reach a level representative of an obese subject and further wherein the amount of the at least one microbe is retained at the level following the weight loss program, wherein the amount or presence of the at least one microbe or product thereof is predictive of weight regain.

According to an aspect of some embodiments of the present invention there is provided a method of reducing the risk of weight gain in a subject who has reached a target weight by practicing a weight loss program comprising:
(a) determining an amount or presence of at least one microbe and/or product thereof in a gut microbiome of the subject, wherein the amount of the at least one microbe is altered during a prior weight gain period of the subject to reach a level representative of an obese subject and further wherein the amount of the at least one microbe is retained at the level following the weight loss program; and
(b) administering to the subject who has reached the target weight a therapeutically effective amount of an agent which up-regulates at least one microbe or product thereof which is down-regulated during the prior weight gain period or administering to the subject a therapeutically effective amount of an agent which down-regulates a microbe or product thereof which is up-regulated during the prior weight gain period, thereby reducing the risk of weight gain in the subject.

According to an aspect of some embodiments of the present invention there is provided a method of monitoring the efficacy of a dieting aid in a subject:
(a) treating the subject with a dieting aid; and
(b) analyzing for the presence or the level of at least one microbe and/or product thereof, wherein an amount of the at least one microbe or product thereofis altered during a prior weight gain period of the subject to reach a level representative of an obese subject and further wherein the amount of the at least one microbe is retained at the level following the weight loss program; wherein the level or presence of the at least one microbe or product thereof is indicative of the efficacy of a dieting aid.

According to an aspect of some embodiments of the present invention there is provided a method of reducing the risk of weight gain in a subject who has reached a target weight by practicing a weight loss program, the method comprising administering to the subject an agent which alters the gut microbiome of the subject so that a signature of the gut microbiome becomes more similar to a signature of a gut microbiome of a non-obese subject who has not undergone a weight loss program, thereby reducing weight gain in the subject.

According to further features in the described preferred embodiments, the at least one microbe is differentially present in the gut microbiome of the subject as compared with in the gut microbiome of a non-obese control who has not undergone a weight loss program.

According to further features in the described preferred embodiments, the product thereof is a metabolite.

According to further features in the described preferred embodiments, the signature of the gut microbiome comprises a microbe diversity.

According to further features in the described preferred embodiments, the agent is a fecal transplant of a healthy subject who has not undergone a weight loss program.

According to further features in the described preferred embodiments, the subject who has reached the target weight has terminated the weight loss program.

According to further features in the described preferred embodiments, the signature of the gut microbiome is a metabolite signature.

According to further features in the described preferred embodiments, the signature of the gut microbiome is a bacterial signature.

According to further features in the described preferred embodiments, the agent downregulates at least one metabolite selected from the group consisting of ursodeoxycholate, glycocholate, phenylacetate and heptanoate.

According to further features in the described preferred embodiments, the agent is a flavonoid.

According to further features in the described preferred embodiments, the flavonoid is apigenin and/or naringenin.

According to further features in the described preferred embodiments, the agent is a probiotic.

According to further features in the described preferred embodiments, the probiotic is a bacterial population associated with nitrate synthesis or heptose biosynthesis.

According to further features in the described preferred embodiments, the agent is an antibiotic.

According to further features in the described preferred embodiments, the antibiotic agent downregulates an amount and/or activity of the class Mollicutes or of the order Bacteroidales.

According to further features in the described preferred embodiments, the method further comprises analyzing the signature of the gut microbiome of the subject prior to the administering.

According to further features in the described preferred embodiments, the analyzing is effected in a fecal sample of the subject.

According to further features in the described preferred embodiments, the at least one microbe is set forth in FIG. 4F.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1G:
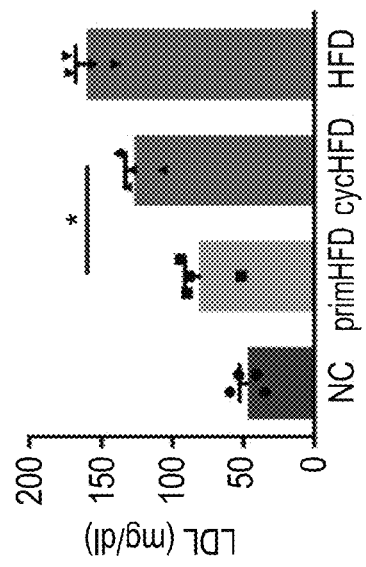
Figure 1H:
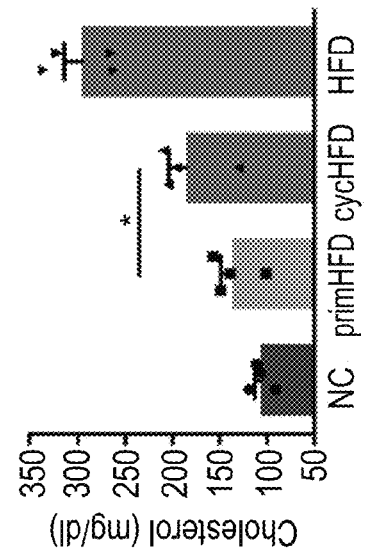

FIGS. 1A-1L illustrate enhanced recurrent weight gain after treatment of obesity. A, B, Schematic of experimental setup (A) and weights (B) of mice undergoing weight cycling and controls. C-J, Body fat content (C), coronal (above) and axial (below) MRI scans (D), glucose levels after GTT (E), glucose level quantification (F), and serum levels of leptin (G), total cholesterol (H), LDL (I), and HDL (J) of weight cycling mice during the second cycle of obesity and controls. K, L, Weight cycling in mice treated with celastrol to lose weight (K), and mice treated with leptin antagonist to induce weight gain (1). Colored bars below weight curves depict durations of the indicated treatments. Results in B-J are representative of more than 5 independent experiments; results in K-L are from one experiment. * $p<0.05$, n.s. not significant.

FIGS. 2A-2L illustrate persistent microbiome alterations after weight loss. A-D, Body fat content (A), glucose levels after GTT (B), glucose level quantification (C), and insulin levels (D) in post-dieting mice after return to normal weight compared to controls. E-F, Beta-diversity (E) and alpha-diversity (F) of microbiota composition over time in weight cycling mice and controls. G, Example of bacterial taxa whose abundance does not recover after dieting. H, I, Heatmaps of OTUs determined by 16S sequencing (H), and bacterial genes determined by metagenomic sequencing (I) over the course of weight gain and subsequent dieting. J, Principal component analysis of bacterial metagenomics over time in weight cycling mice and controls. K-J, Examples of KEGG functions whose abundance does not recover after dieting. Results are representative of more than 5 (A-H) or 2 (I-J) independent experiments.  $p<0.01$, * $p<0.001$, n.s. not significant.

FIGS. 3A-3L illustrate that microbiome alterations following weight loss drive exaggerated recurrent weight gain. A, Schematic of antibiotic intervention during weight cycling. B, C, Beta-diversity of fecal microbiota (B) and weight curve (C) over time in weight cycling mice undergoing antibiotic treatment. Colored bars below weight curve depict durations of the indicated treatments. D-F, Body fat content (D), glucose levels after GFF (E), and glucose level quantification (F) of weight cycling mice with or without antibiotic treatment during the second cycle of obesity. G, Schematic of fecal transplantation to germ-free mice after dieting. H, PCoA of fecal microbiota in FMT recipient mice one week after fecal transplantation. I, Weight curve of FMT recipient mice after fecal transplantation with or without HFD. J, Glucose levels after GTT in FMT recipients one week after fecal transplantation. K, Weight curve of mice that were monitored for microbiota equilibration after dieting before secondary obesity was induced. L, Microbial dissimilarity over time of weight cycling mice and mice on continuous HFD compared to NC controls. Results in B-J are representative of 3 independent experiments; results in K-L are from one experiment. * p<0.05, n.s. not significant.

FIGS. 4A-4F illustrate accurate prediction of post-dieting weight regain by microbiota features. A, Schematic of 16S data assembly from mice of identical weight and metabolic phenotype, but different history of obesity, for prediction of weight gain upon HFD feeding. B, Prediction of prior obesity based on 16S data. C, D, Correlation of predicted versus measured weight gain upon HFD feeding based solely on 16S data (C) or on a combination of 16S data and inferred information about prior obesity. E, Ranked list of OTUs contributing to algorithm-based weight production. F, List of 10 most important OTUs from (E).

FIGS. 5A-5F illustrate that microbiome modulation ameliorates the post-dieting weight gain. A, Schematic of fecal transplantation experiments. B, Weight curve of undergoing weight cycling, with fecal transplantations from either non-obese or cycling mice. C, Body fat content of weight cycling mice, with fecal transplantations from either non-obese or cycling mice, during the second cycle of obesity. D, Schematic of time points for metabolomics analysis. E, Relative metabolite abundances between weight cycling mice and mice on continuous HFD before and after dieting. Dashed lines indicate persistent changes of enriched or depleted metabolites that do not recover upon dieting. F, Weight curve of weight cycling mice receiving supplementation of apigenin and naringenin. Colored bars below weight curves depict durations of the indicated treatments. All results are representative of 2 independent experiments. * p<0.05

Figure 6B:
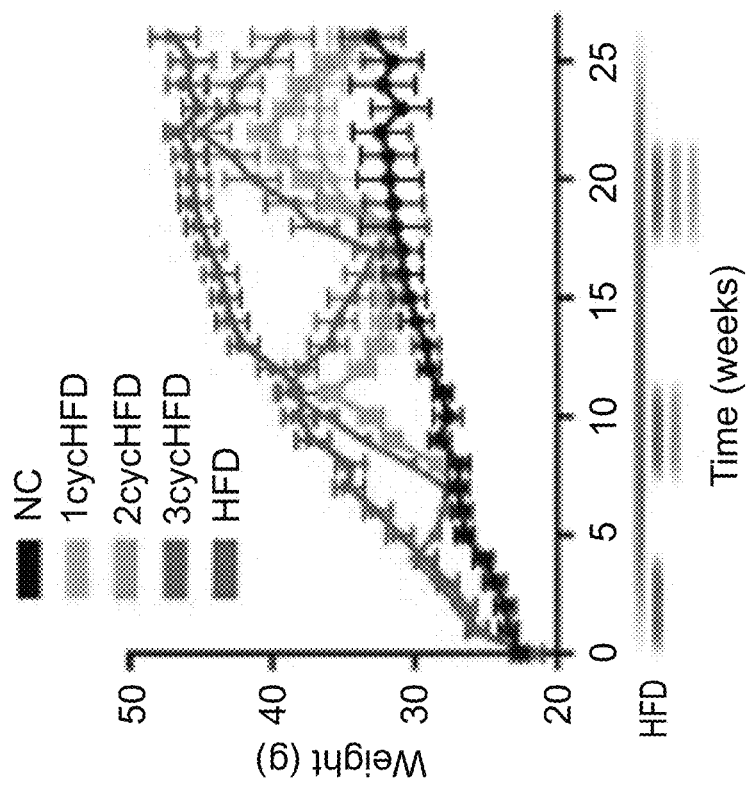
Figure 6A:
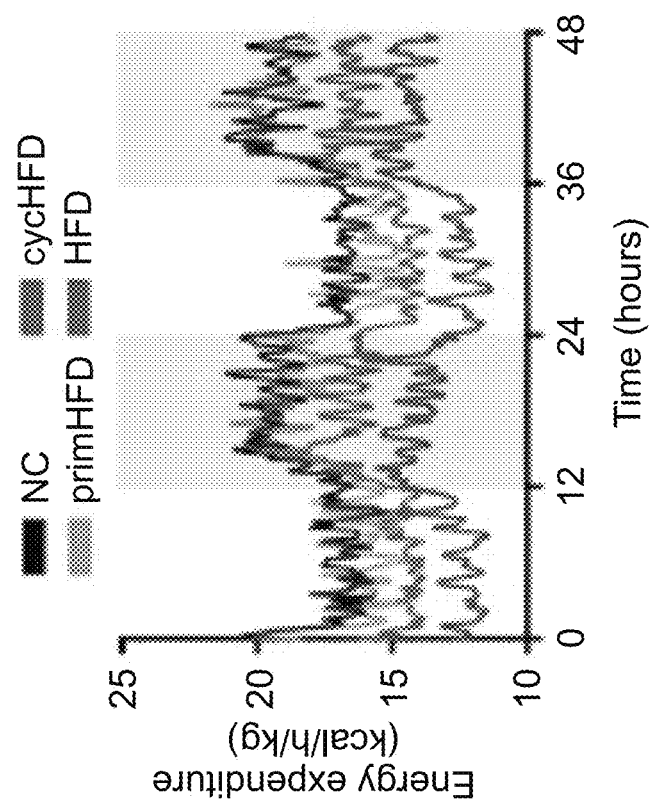

FIGS. 6A-6B illustrate enhanced recurrent weight gain after treatment of obesity. A. Energy expenditure over 48 hours B. Recurrent weight gain in mice undergoing three diet cycles. Colored bars below weight curves depict durations of the indicated treatments. N=10 per group (e, n=4). Experiments were repeated at least twice. Shown are mean SEM. * p<0.05, ** p<0.01 by ANOVA.

FIGS. 7A-7I illustrate persistent microbiome alterations after weight loss. A, Schematic of sampling times for microbiota analysis. B-F, Principal coordinate analyses (PCoA) of unweighted UniFrac distances of microbiota composition at the indicated time points. I. OTU heatmap of weight cycling mice and controls before (week 0), during (week 4), and after obesity (week 7). H, I, Principal component analysis (PCA) (H) and heatmap (I) of bacterial KEGG pathways in weight cycling mice and controls. N as indicated (H, n=10). Experiments were repeated at least twice. Shown are mean SEM. * p<0.05,  p<0.01, ** p<0.0001 by ANOVA.

Figure 8A:
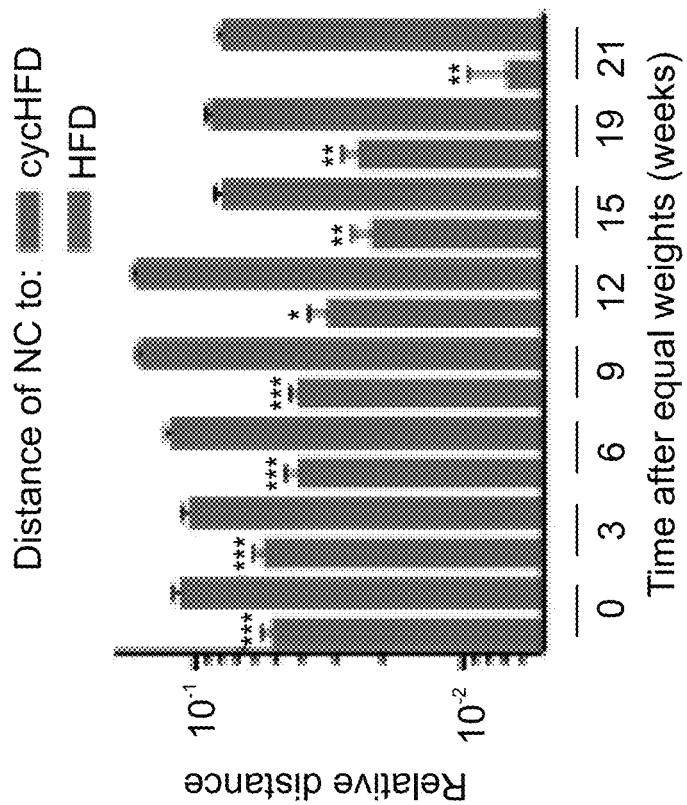
Figure 8B:
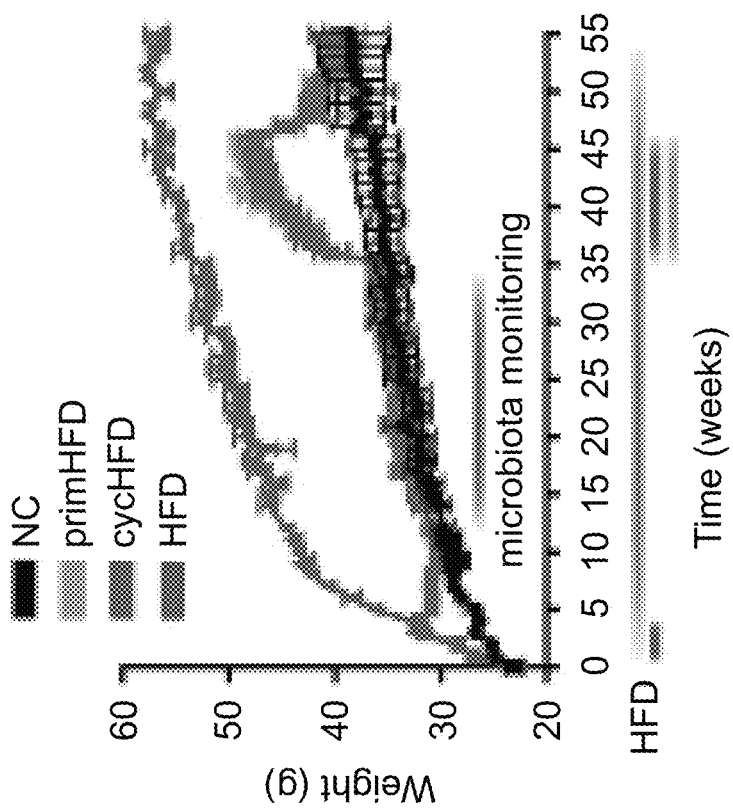

FIGS. 8A-8B illustrate post-dieting microbiome alterations drive exacerbated weight regain. A, Weight curve of mice monitored for microbiota equilibration after dieting before induction of secondary obesity. B, Microbial dissimilarity over time between cycHFD and HFD mice compared to NC controls. Shown are mean±SEM. *p<0.05,  p<0.01, * p<0.001, n.s. not significant by ANOVA.

FIGS. 9A-9K. Microbiome modulation ameliorates post-dieting weight regain. A-E, Schematic (A), weight curve (B), glucose level quantification after GTT (C), body fat content (D), and representative MRI scans during weight regain of weight cycling mice undergoing fecal microbiota transplantation (FMT)(E). F, G Relative abundances (F) and heatmap (G) of intestinal metabolites before, during, and after obesity. H-K, Normalized intestinal abundances of apigenin and naringenin before, during, and after obesity, as well as 15 weeks after successful dieting (H, I), in antibiotics-treated (Abx), germ-free (GF), and control mice (J), and in mice treated with antibiotics during weight loss. N=5. Experiments were repeated at least twice. Shown are mean f SEM. * p<0.05, ** p<0.01 by ANOVA or Mann-Whitney U-test (K).

Figure 10A:
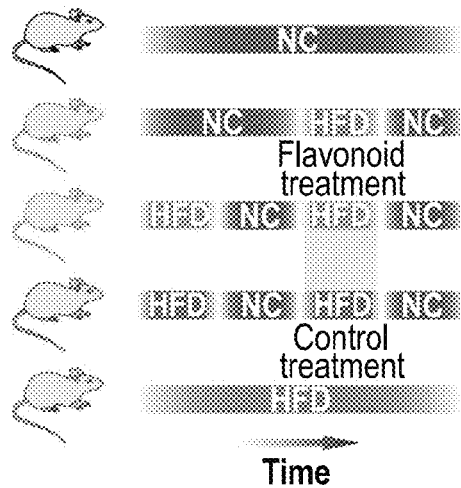

FIGS. 10A-ION. Metabolite modulation ameliorates post-dieting weight regain. a-f, Schematic (A), weight curve (B), representative MRI scans (C), representative energy expenditure recording (D), and quantifications during the dark phase (E) and light phase (F) of weight cycling mice with or without supplementation of apigenin and naringenin (A/N) during weight regain. G, Energy expenditure recording during weight regain of weight cycling mice with or without antibiotic treatment before weight regain. H-M, Brown adipose tissue (BAT) UCP-1 transcript (H-K) or protein (L,M) levels in mice on HFD or NC receiving A/N or vehicle by daily gavage for 2 weeks (H), in weight cycling mice with or without A/N treatment during weight regain (I). in BAT explants cultured with A/N for 24 hours, and in mice during weight regain after antibiotic treatment during weight loss. N, Model of diet-microbiota-energy expenditure interactions during dieting and weight regain. N=5. Experiments were repeated at least twice. Shown are mean f SEM. * p<0.05,  p<0.01, * p<0.001 by ANOVA and Mann Whitney U-test (1, K, M).

Figure 11A:
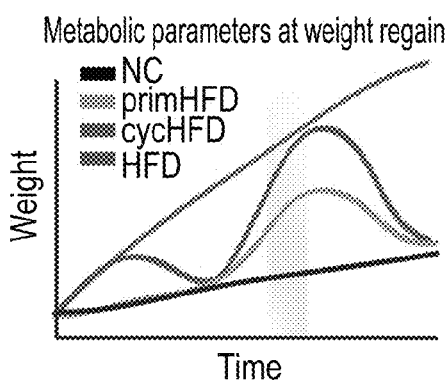
Figure 11B:
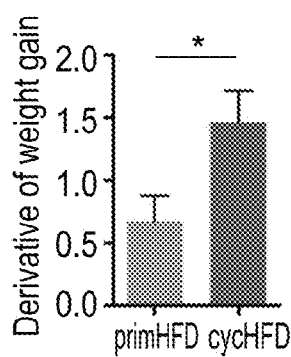

FIGS. 11A-11Q. Metabolic measurements during weight regain. A, Schematic indicating time point of metabolic measurements. B, Quantification of weight regain by weight gain slope. C, Net weight gain induced by 8 weeks of HFD in weight cycling mice and continuous HFD controls. D, E, Coronal (above) and axial (below) MRI scans (D), and quantification of body fat content (D). F, G, Serum levels of leptin (F) and HDL (G) during the second HFD exposure of mice undergoing weight cycling and controls. H, I, Quantification of dark phase (H) and light phase (I) energy expenditure upon weight regain of weight cycling mice. I-Q, Representative recordings (J, M, P, Q) and quantifications (K, L, N, O) of $O_2$ consumption (J-L) $CO_2$ consumption (M-O), physical activity (P) and food intake (Q) upon weight regain of weight cycling mice. Experiments were repeated twice. Shown are mean SEM. *p<0.05, ** p<0.01, n.s. not significant by ANOVA or Mann Whitney U-test (B, C)

Figure 12A:
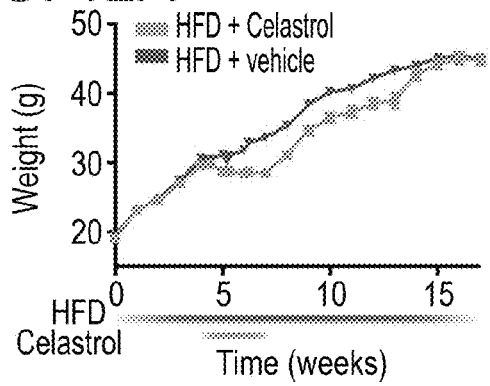
Figure 12B:
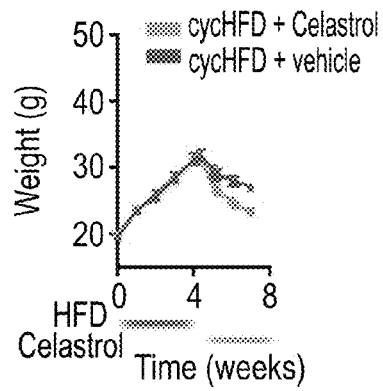
Figure 12C:
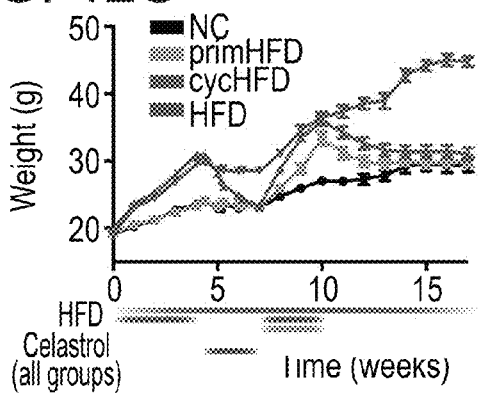
Figure 12D:
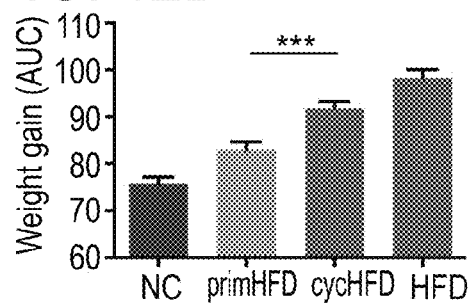
Figure 12E:
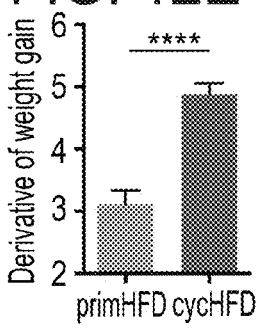
Figure 12F:
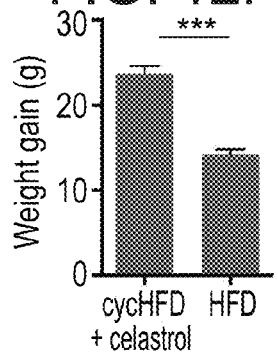
Figure 12G:
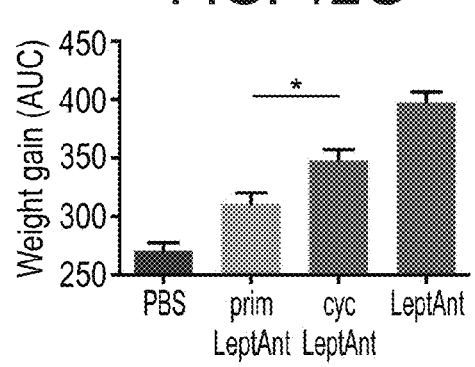
Figure 12H:
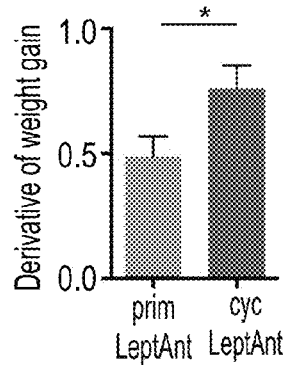
Figure 12I:
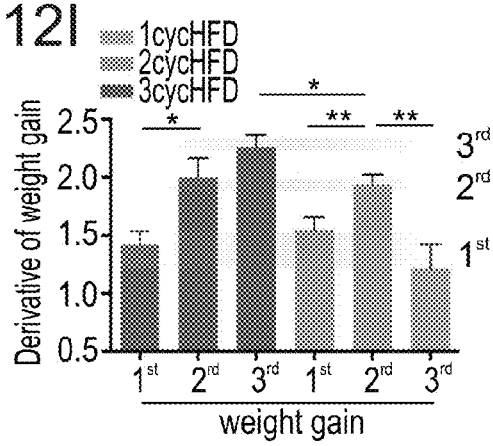
Figure 12J:
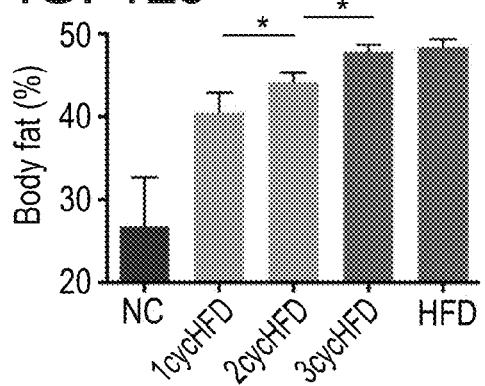
Figure 12K:
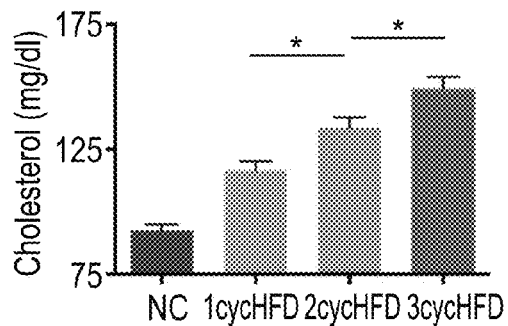
Figure 12L:
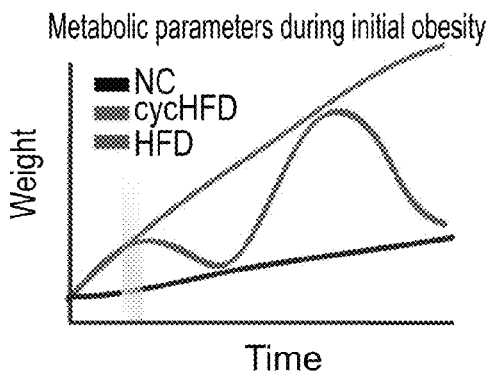
Figure 12M:
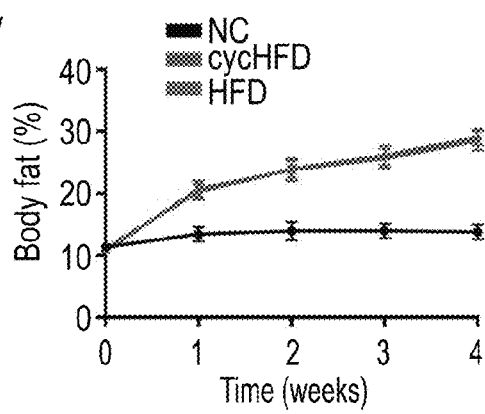
Figure 12N:
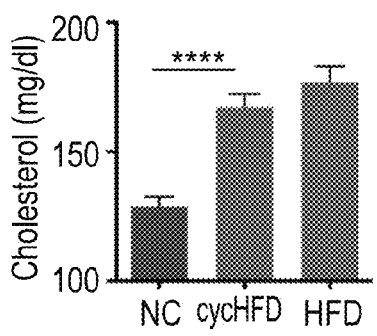
Figure 12O:
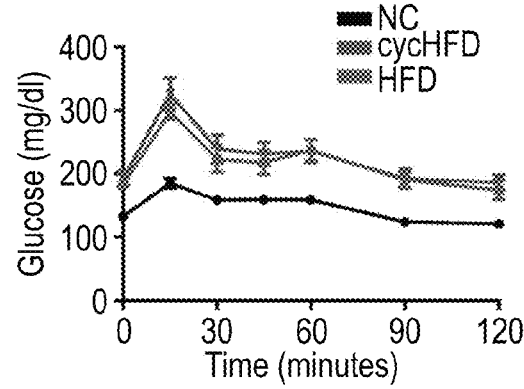
Figure 12P:
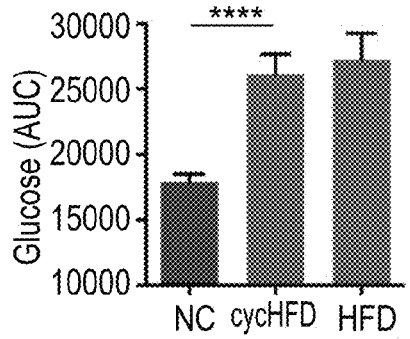
Figure 12Q:
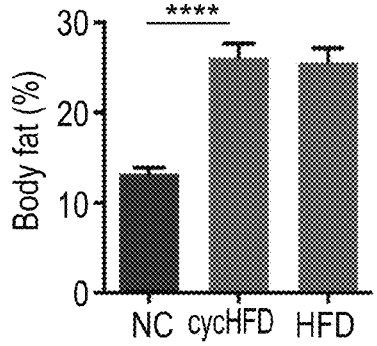
Figure 14G:
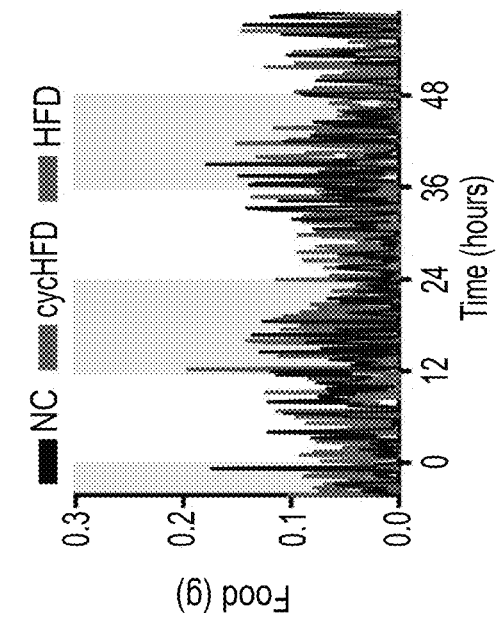
Figure 14H:
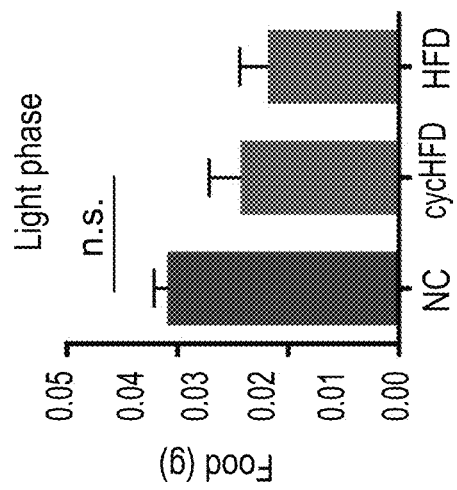
Figure 14I:
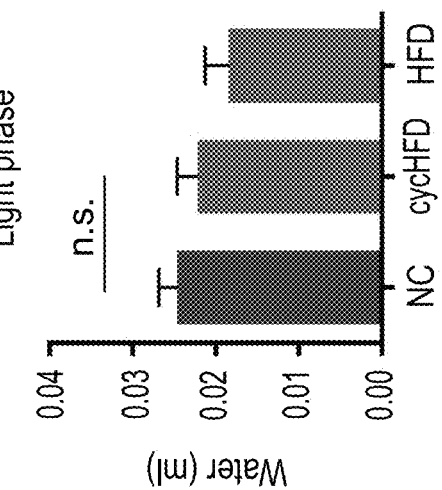
Figure 14J:
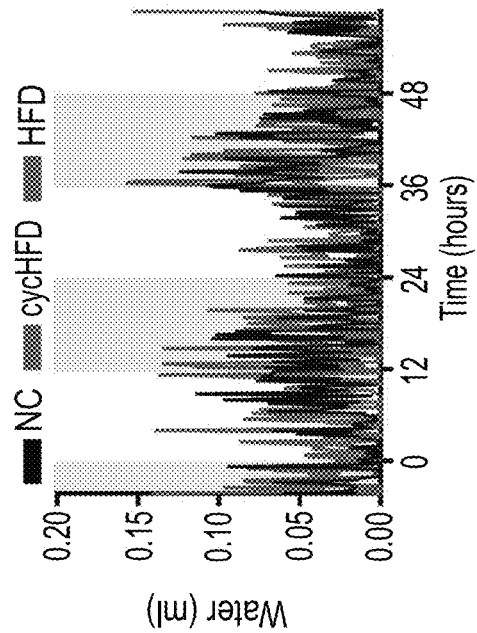
Figure 14K:
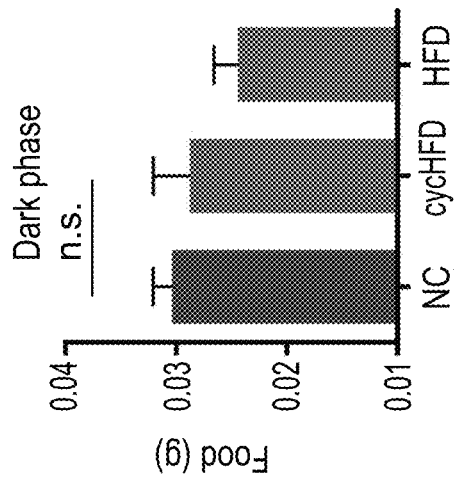
Figure 14L:
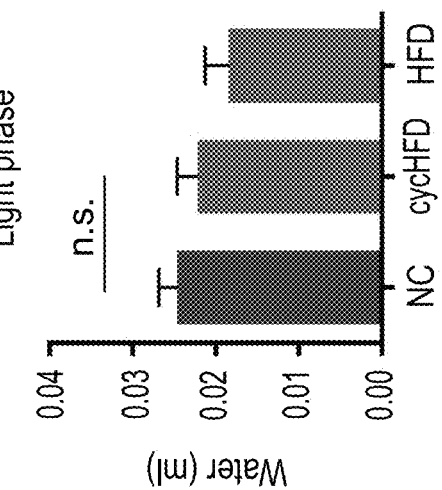

FIGS. 12A-12Q. A, B, The effect of celastrol on weight loss in mice continuously fed a HFD (A) and mice with alternating diets (B). C-F, Weight curve (C), weight regain quantification by AUC (D), weight regain slope (E), and net weight gain on HFD (F) by weight cycling mice treated with celastrol to lose weight and controls. G, H, Quantification of weight regain by AUC (G), weight regain slope (H) of leptin antagonist-treated weight cycling mice and controls. I-K, Weight gain slope (I), body fat content (J), and serum cholesterol levels (K) of weight cycling mice undergoing a third weight cycle and controls. L, Schematic of the analyzed time point in N-Q. M, Weight gain during 4 weeks of HFD. N-Q, Serum cholesterol levels (N), glucose levels after GTT (0), glucose level quantification (P), and quantification of body fat content (Q) in weight cycling mice during initial obesity and controls. Experiments were repeated at least twice. Shown are mean±SEM. * p<0.05,  p<0.01, * p<0.001, **** p<0.0001 by ANOVA.

FIGS. 13A-13L. Recovery of metabolic parameters after dieting. A, Schematic of the analyzed 'nadir' time point. B-F Body fat content (B), serum cholesterol levels (C), glucose levels after GTT (D), glucose level quantification (E), and serum insulin levels (F) in weight cycling mice upon return to normal weight. G-L, Representative recordings (G, J) and quantifications (H, I, K, L) of 02 and $CO_2$ consumption by weight cycling mice upon return to normal weight and controls. Experiments were repeated twice. Shown are mean±SEM. n.s. not significant by ANOVA.

FIGS. 14A-14L. Metabolic measurements after dieting. Representative recordings (A,D,G,J), dark phase quantifications (B,E,H,K), and light phase quantifications (C,F,I,L) of energy expenditure (A-C), physical activity (D-F), food intake (G-I), and water consumption (J-L) of weight cycling mice during weight regain and controls. Experiments were repeated twice. Shown are mean f SEM. n.s. not significant by ANOVA.

FIGS. 15A-15M. Persistent microbiome changes after dieting. A, Quantification of UniFrac distances of weight cycling mice from NC control at the indicated time points. Plots correspond to the PCoA analyses in FIGS. 7B-F. B-D, PCoA analyses and distance quantification (insets) of V3N4-targeted 16S sequencing of mice before (B), during (C), and after (D) diet-induced obesity and subsequent weight loss. E-I, Examples of OTUs whose abundance does (E, F) or does not recover (G-I) after dieting. J-M, PCoA analyses (J, K), UniFrac distance (L) and alpha-diversity (M) at the 'nadir' time point of post-dieting mice that had received celastrol to accelerate weight loss. Experiments were repeated twice. Shown are mean±SEM. * $p<0.05$,  $p<0.01$, * $p<0.001$, **** $p<0.0001$ by ANOVA.

FIGS. 16A-16J. Persistent metagenomic changes after dieting. A, Heatmap of normalized gene abundance in the microbiota of mice before (0 weeks), during (4 weeks), and after obesity (7 weeks). B, C, Examples of genes whose abundance does not recover after dieting. D, PCA of bacterial KEGG modules over time in weight cycling mice and controls. E-J, Examples of KEGG pathways whose abundance is reversibly decreased (E, F), reversibly increased (G, H), or persistently decreased (I, J) during obesity and dieting. Data are from one experiment. Shown are mean±SEM. * $p<0.05$, ** $p<0.01$ by ANOVA.

FIGS. 17A-17L. The post-dieting microbiota drives recurrent obesity. A, B, PCoA (A) and alpha-diversity (B) of fecal microbiota after dieting ('nadir' time point at week 8) from mice with or without antibiotic treatment during weight loss. C, Net weight gain induced by 8 weeks of HFD in weight cycling mice or continuous HFD control with or without antibiotic treatment between weeks 4 and 8. D, E, Glucose levels after oral GTT (D) and glucose level quantification after GTT (E) during secondary weight gain (week 12) in mice with or without antibiotic treatment during weight loss. F-H, PCoA of fecal microbiota from formerly obese mice and controls at the time of dieting-induced weight normalization (F), 15 weeks after weight normalization (G), and 21 weeks after weight normalization (H). I-K, Correlation analysis (I) and examples (J, K) of microbial taxa undergoing gradual normalization in abundance over a period of 21 weeks after weight normalization. L, Quantification of secondary weight gain after microbiota normalization. Experiments were repeated twice. Shown are mean±SEM. * $p<0.05$, ** $p<0.01$, n.s. not significant by ANOVA.

Figure 18A:
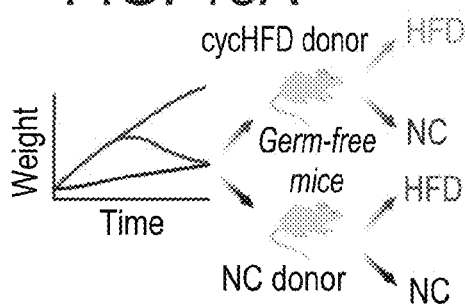

FIGS. 18A-18O Transfer, prediction and treatment of weight regain by microbiome features. A, Schematic of microbiota transfer to germ-free mice after dieting. Recipients were fed either HFD or NC. B-D, PCoA of recipient microbiota (B) and relative UniFrac distances to NC controls (C, D) of germ-free mice one week after transplantation with microbiota from weight cycling mice or controls, and fed either a NC (c) or HFD (D). E, F, Quantifications of weight gain (E) and blood glucose after GTT (F) in germ-free recipients of microbiota from weight cycling mice or controls. G,H, Correlation of predicted and measured weight gain when prediction is based solely on inferred history of obesity (G) or solely on 16S sequencing (H). I-K, PCoA of fecal microbiota (I) and relative UniFrac distances between donors J) and recipients (K) two weeks after the onset of daily FMT from cycHFD or NC mice to mice undergoing weight cycling. L-O, Quantification of secondary weight gain (L), net weight gain induced by 8 weeks of HFD feeding (M), glucose levels after GTT (N) and lean mass (0) in weight cycling mice and controls with or without FMT. Experiments were repeated twice. Shown are mean SEM. * $p<0.05$,  $p<0.01$, ** $p<0.0001$, n.s.not significant by ANOVA or Mann-Whitney U-test (C, D, J, K).

FIGS. 19A-19I. Persistent metabolomic changes after dieting. A-H, Examples of metabolites whose abundance is reversibly decreased (A, B), reversibly increased (C, D), persistently decreased (E, F), or persistently increased (G, H) during obesity and dieting. I, Schematic of flavonoid biosynthetic pathways leading to the production and conversion of naringenin. KEGG IDs of key enzymes are indicated. Genes found in our metagenomic data set are indicated in green. Data are from one experiment. Shown are mean f SEM. * $p<0.05$, ** $p<0.01$ by ANOVA.

Figure 20A:
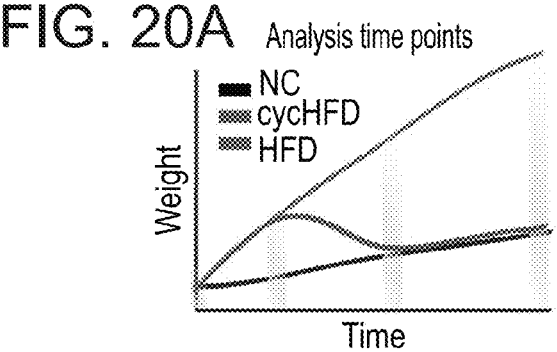

FIGS. 20A-20P. Microbiota control of post-dieting metabolic complications through intestinal flavonoids. A, Schematic showing sampling times in obesity/recovery cycle experiment. B, Dietary flavonoids in NC and HFD. C-E, Abundance of flavanone 4-reductase (C), chalcone synthase (D), and eriodictyol (E) over time in the feces of mice undergoing weight cycling and controls. F, Quantification of flavanone 4-reductase levels in fecal DNA relative to host DNA in weight cycling mice at the end of the weight loss period, with or without antibiotic treatment during weight loss. G, Schematic of sampling time upon weight regain. H, I, Abundance of apigenin (H) and naringenin (I) in the feces of mice undergoing post-dieting weight regain and controls. J-N, Flavonoid levels (J, K), PCoA of fecal microbiota (L), net weight gain induced by 8 weeks of HFD (M), and weight regain quantification by AUC (N) of weight cycling mice supplemented with apigenin and naringenin during the weight regain. 0, P, Weight curve (0) and weight gain quantification (P) of weight cycling mice with or without naringenin supplementation. Experiments were repeated twice. Shown are mean SEM. * $p<0.05$, ** $p<0.01$ by ANOVA or Mann-Whitney U-test (F, H, I).

FIGS. 21A-21L. Metabolic measurements in flavonoid-treated mice. Representative recordings (A,D,G,J), dark phase quantifications (B,E,H,K), and light phase quantifications (C,F,I,L) of 02 consumption (A-C), $CO_2$ consumption (D-F), respiratory exchange ratio (G-I), and physical activity (J-L) of weight cycling mice with or without supplementation of apigenin and naringenin (A/N) during weight regain. Data are from one experiment. Shown are mean±SEM. ** $p<0.01$ by ANOVA.

FIGS. 22A-22L Metabolic measurements in flavonoid- and antibiotics-treated mice. Representative recordings (A,D), dark phase quantifications (B,E), and light phase quantifications (C,F) of food (A-C) and water consumption (D-F), of weight cycling mice with or without supplementation of apigenin and naringenin (A/N) during weight regain. G, Schematic indicating time of metabolic measurements during the weight regain phase. H, I, Quantifications of energy expenditure in weight cycling mice with or without antibiotic treatment during weight loss. J-L, Representative recording (J) and quantifications (K, L) of 02 consumption by weight cycling mice with or without antibiotic treatment (Abx) during weight loss. Data are from one experiment. Shown are mean SEM. ** p<0.01 by ANOVA.

FIGS. 23A-23L. Metabolic measurements in antibiotics-treated mice. Representative recordings (A,D,G,F), dark phase quantifications (B,E,H,K), and light phase quantifications (C,F,I,L) of $CO_2$ consumption (A-C), respiratory exchange ratio (D-F), physical activity (G-I) and food intake (J-L) by weight cycling mice with or without antibiotic treatment (Abx) during weight loss. Data are from one experiment. Shown are mean SEM. ** p<0.01 by ANOVA.

DESCRIPTION OF SPECIFIC EMBODIMENTS OF THE INVENTION

The present invention, in some embodiments thereof, relates to methods of maintaining a target body weight and analyzing the likelihood of weight regain following a diet.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Obesity represents an emerging global burden, with significant efforts being devoted to weight reduction. However, the majority of dieting individuals fail to maintain a reduced weight over time, and instead undergo excessive weight regain. The mechanisms driving relapsing post-dieting obesity remain elusive.

The present inventors have now uncovered a memory-like signature of the intestinal microbiome that persists after successful dieting of obese mice and drives a tendency for exaggerated weight regain and metabolic alterations upon re-encounter of obesity-promoting conditions. This microbiome memory is characterized by a long-lived multi-omic microbial signature and is capable of transmitting the obesity-promoting phenotype.

Whilst reducing the present invention to practice, the present inventors developed a personalized machine-learning algorithm enabling microbiome-based prediction of relapsing weight gain in mice (FIGS. 4A-F), and demonstrated that fecal transplantation and 'post-biotic' intervention with the flavonoids apigenin and naringenin may prevent excessive secondary weight gain (FIGS. 5A-F).

Based on the above described results, the present inventors propose targeting the microbiome for diagnosing and treating dieting-induced relapsing obesity in humans.

The present inventors have further uncovered a possible mechanism by which the flavonoids prevent secondary weight gain. Specifically, the present inventors have found that the flavonoids apigenin and naringenin (as well as antibiotic treatment) upregulate expression of the thermogenic factor uncoupling protein-1 (UCP-1). Thus the present inventors propose that a high fat diet (HFD) promotes the growth of flavonoid-metabolizing bacteria, which in turn decrease the amount of bioavailable flavonoids, thereby negatively regulating UCP-1-driven energy expenditure and promoting recurrent weight gain. Accordingly, the present inventors contemplate agents other than the above mentioned flavonoids that upregulate expression of UCP-1 to prevent secondary weight gain.

Thus, according to a first aspect of the present invention there is provided a method of analyzing the likelihood of weight regain in a subject who has reached a target weight by practicing a weight loss program, the method comprising determining an amount or presence of at least one microbe and/or product thereof in the gut microbiome of the subject, wherein the amount of the at least one microbe is altered during a prior weight gain period of the subject to reach a level representative of an obese subject and further wherein the amount of the at least one microbe is retained at that level following the weight loss program, wherein the amount or presence of the at least one microbe or product thereof is predictive of weight regain.

As used herein the term "subject" refers to a mammalian subject (e.g. mouse, cow, dog, cat, horse, monkey, human), preferably human.

According to this aspect of the present invention, the method is used to predict the likelihood of relapsing weight gain (obesity) following a program of weight loss.

Thus, the subject of the present invention has lost at least 0.5 kg in weight, 1 kg in weight, 1.5 kg in weight, 2 kg in weight, 2.5 kg in weight, 3 kg in weight, 3.5 kg in weight, 4 kg in weight, 4.5 kg in weight, 5 kg in weight, 5.5 kg in weight, 6 kg in weight, 6.5 kg in weight, 7 kg in weight, 7.5 kg in weight, 8 kg in weight, 8.5 kg in weight, 9 kg in weight, 9.5 kg in weight, 10 kg in weight, 10.5 kg in weight, 11 kg in weight, 11.5 kg in weight, 12 kg in weight, 12.5 kg in weight, 13 kg in weight, 13.5 kg in weight, 14 kg in weight, 14.5 kg in weight, 15 kg in weight, 15.5 kg in weight, 16 kg in weight, 16.5 kg in weight, 17 kg in weight, 17.5 kg in weight, 18 kg in weight, 18.5 kg in weight, 19 kg in weight, 19.5 kg in weight or even 20 kg in weight.

According to one embodiment, the weight loss program is effect for at least 2 weeks, 3 weeks, 4 weeks, 5 weeks, 6 weeks, 7 weeks, 8 weeks, 9 weeks or 10 weeks. In one embodiment, the weight loss program is effected for 1 month-1 year, or 1 month-6 months. Preferably, the weight loss program is not effected for less than 1 week, 2 weeks or 3 weeks.

The target weight of the subject may be a weight wherein the BMI thereof is between 18.5-24.9. According to another embodiment, the target weight is the obese weight of the subject minus 1 kg, minus 2 kg, minus 3 kg, minus 4 kg, minus 5 kg, minus 6 kg, minus 7 kg, minus 8 kg, minus 9 kg, minus 10 kg or more.

The weight loss program may comprise a dietary weight loss program and/or an exercise weight loss program.

Preferably the weight loss of the subject is a result of a change in diet and/or exercise regime and not a result of illness.

Non-limiting examples of dietary weight loss programs include but are not limited to a South Beach Diet, a Dukin diet, a Stillman diet, an Atkins Diet, a gluten-free diet, a ketogenic diet, a low-residue diet, a liquid diet, a vegetarian diet, a low-calorie diet (e.g., Weight Watches, Jenny Craig, Nutrisystems), a low-fat diet, a low-carbohydrate diet, a low-protein diet, a low-monosodium glutamate (MSG) diet, a detox diet, an elimination diet, a specific carbohydrate diet, a diabetic diet, a dietary approach to stop hypertension diet (DASH) diet, a best bet diet, an organic diet, and combinations thereof.

Once the subject has reached his target weight, he may resume the same eating/exercise regime that he was on prior to the weight loss program. Alternatively, the subject may begin a new eating/exercise regime which aims at weight maintenance. Alternatively, the subject may continue the same weight loss program, yet not adhere to the program as stringently as when he used the program for weight loss purposes.

As mentioned, the method of this aspect of the present invention comprises determining an amount or presence of at least one microbe and/or product thereof in the gut microbiome of the subject. Whilst the level of any number of microbes or products thereof may be measured, it will be appreciated that the microbes which are used in the prediction (i.e. the relevant signature) are typically those that fulfill two criteria:

(i) their level is altered during a prior weight gain period of the subject to reach a level representative of an obese subject; and (ii) the microbe is retained at the level representative of the obese subject following the weight loss program (e.g. does not change more than 1%, 2%, 3%, 4%, 5%, 6%, 7%, 8%, 9% or 10% in either direction).

According to a particular embodiment, the level of the microbe is up-regulated during the prior weight gain period of the subject. The up-regulation may be at least 10% higher, 20% higher, 30% higher, 40% higher, 50% higher, 60% higher, 70% higher, 80% higher, 90% higher or even 100% than the level prior to the weight gain period.

According to another embodiment, the level of the microbe is down-regulated during the prior weight gain period of the subject. The down-regulation may be at least 10% lower, 20% lower, 30% lower, 40% lower, 50% lower, 60% lower, 70% lower, 80% lower, 90% lower or even lower % than the level prior to the weight gain period.

In other embodiments, the microbe which is used in the prediction (i.e. the one used in the microbiome signature) is one that is differentially present (by at least 10%, 20%, 30%, 40%, 50%, 60%, 7%, 80%, 90% or greater) in the gut microbiome of the subject as compared with in the gut microbiome of a non-obese control who has not undergone a weight loss program.

As used herein, the term "microbiome" refers to the totality of microbes (bacteria, fungae, protists), their genetic elements (genomes) in a defined environment.

According to a particular embodiment, the microbiome is a gut microbiome (i.e. intestinal microbiome).

In some embodiments, a microbiota sample is collected by any means that allows recovery of the microbes and without disturbing the relative amounts of microbes or components or products thereof of a microbiome. In some embodiments, the microbiota sample is a fecal sample. In other embodiments, the microbiota sample is retrieved directly from the intestine.

According to one embodiment the microbiome sample (e.g. fecal sample) is frozen and/or lyophilized prior to analysis. According to another embodiment, the sample may be subjected to solid phase extraction methods.

In some embodiments, the presence, level, and/or activity of between 5 and 100 types of microbes (e.g. bacteria) are measured. In some embodiments, the presence, level, and/or activity of between 50 and 500 types of microbes (e.g. bacteria) are measured. In some embodiments, the presence, level, and/or activity of substantially all species/classes/families of bacteria within the microbiome are measured. In still more embodiments, the presence, level, and/or activity of substantially all the bacteria within the microbiome are measured.

In some embodiments, only the microbes which fulfill the two criteria set forth above are measured.

In still other embodiments, the majority of the microbes which are measured fulfill the two criteria set forth herein above.

Figure 4E:
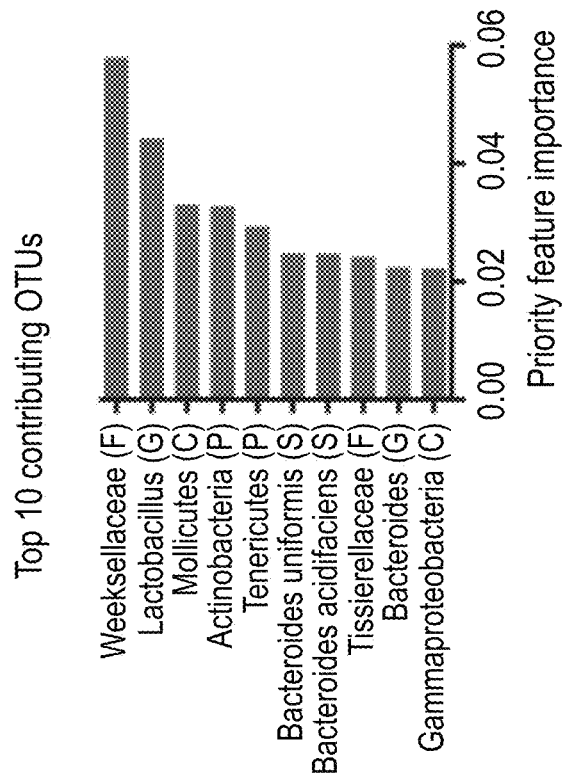
Figure 4F:
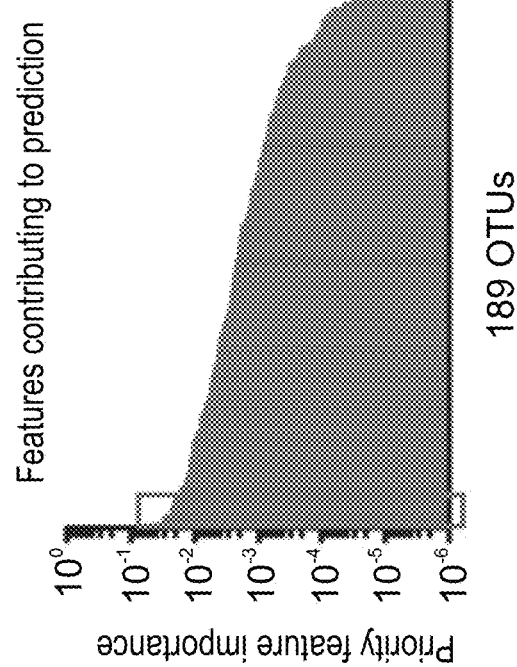

In still other embodiments, at least 1, 2, 3, 4, 5, 6, 7, 8, 9, or ten microbe classifications which are described in FIG. 4F of the Examples section is measured.

In still other embodiments, the majority of the microbes which are measured are described in FIG. 4F.

Measuring a level or presence of a microbe may be effected by analyzing for the presence of microbial component or a microbial by-product. Thus, for example the level or presence of a microbe may be effected by measuring the level of a DNA sequence. In some embodiments, the level or presence of a microbe may be effected by measuring 16S rRNA gene sequences or 18S rRNA gene sequences. In other embodiments, the level or presence of a microbe may be effected by measuring RNA transcripts. In still other embodiments the level or presence of a microbe may be effected by measuring proteins. In still other embodiments, the level or presence of a microbe may be effected by measuring metabolites.

Quantifying Microbial LeveLs:

It will be appreciated that determining the abundance of microbes may be affected by taking into account any feature of the microbiome. Thus, the abundance of microbes may be affected by taking into account the abundance at different phylogenetic levels; at the level of gene abundance; gene metabolic pathway abundances; sub-species strain identification; SNPs and insertions and deletions in specific bacterial regions; growth rates of bacteria, the diversity of the microbes of the microbiome, as further described herein below.

In some embodiments, determining a level or set of levels of one or more types of microbes or components or products thereof comprises determining a level or set of levels of one or more DNA sequences. In some embodiments, one or more DNA sequences comprises any DNA sequence that can be used to differentiate between different microbial types. In certain embodiments, one or more DNA sequences comprises 16S rRNA gene sequences. In certain embodiments, one or more DNA sequences comprises 18S rRNA gene sequences. In some embodiments, 1, 2, 3, 4, 5, 10, 15, 20, 25, 50, 100, 1,000, 5,000 or more sequences are amplified.

16S and 18S rRNA gene sequences encode small subunit components of prokaryotic and eukaryotic ribosomes respectively. rRNA genes are particularly useful in distinguishing between types of microbes because, although sequences of these genes differs between microbial species, the genes have highly conserved regions for primer binding. This specificity between conserved primer binding regions allows the rRNA genes of many different types of microbes to be amplified with a single set of primers and then to be distinguished by amplified sequences.

In some embodiments, a microbiota sample (e.g. fecal sample) is directly assayed for a level or set of levels of one or more DNA sequences. In some embodiments, DNA is isolated from a microbiota sample and isolated DNA is assayed for a level or set of levels of one or more DNA sequences. Methods of isolating microbial DNA are well known in the art. Examples include but are not limited to phenol-chloroform extraction and a wide variety of commercially available kits, including QIAamp DNA Stool Mini Kit (Qiagen, Valencia, Calif.).

In some embodiments, a level or set of levels of one or more DNA sequences is determined by amplifying DNA sequences using PCR (e.g., standard PCR, semi-quantitative, or quantitative PCR). In some embodiments, a level or set of levels of one or more DNA sequences is determined by amplifying DNA sequences using quantitative PCR. These and other basic DNA amplification procedures are well known to practitioners in the art and are described in Ausebel et al. (Ausubel F M, Brent R, Kingston R E, Moore D, Seidman J G, Smith J A, Struhl K (eds). 1998. Current Protocols in Molecular Biology. Wiley: New York).

In some embodiments, DNA sequences are amplified using primers specific for one or more sequence that differentiate(s) individual microbial types from other, different microbial types. In some embodiments, 16S rRNA gene sequences or fragments thereof are amplified using primers specific for 16S rRNA gene sequences. In some embodiments, 18S DNA sequences are amplified using primers specific for 18S DNA sequences.

In some embodiments, a level or set of levels of one or more 16S rRNA gene sequences is determined using phylochip technology. Use of phylochips is well known in the art and is described in Hazen et al. ("Deep-sea oil plume enriches indigenous oil-degrading bacteria." Science, 330, 204-208, 2010), the entirety of which is incorporated by reference. Briefly, 16S rRNA genes sequences are amplified and labeled from DNA extracted from a microbiota sample. Amplified DNA is then hybridized to an array containing probes for microbial 16S rRNA genes. Level of binding to each probe is then quantified providing a sample level of microbial type corresponding to 16S rRNA gene sequence probed. In some embodiments, phylochip analysis is performed by a commercial vendor. Examples include but are not limited to Second Genome Inc. (San Francisco, Calif.).

In some embodiments, determining a level or set of levels of one or more types of microbes comprises determining a level or set of levels of one or more microbial RNA molecules (e.g., transcripts). Methods of quantifying levels of RNA transcripts are well known in the art and include but are not limited to northern analysis, semi-quantitative reverse transcriptase PCR, quantitative reverse transcriptase PCR, and microarray analysis.

In some embodiments, determining a level or set of levels of one or more types of microbes comprises determining a level or set of levels of one or more microbial polypeptides. Methods of quantifying polypeptide levels are well known in the art and include but are not limited to Western analysis and mass spectrometry.

As mentioned herein above, as well as (or instead of) analyzing the level of microbes, the present invention also contemplates analyzing the level of microbial products.

Examples of microbial products include, but are not limited to mRNAs, polypeptides, carbohydrates and metabolites.

In some embodiments, the presence, level, and/or activity of metabolites of at least ten types of microbes are measured. In other embodiments, the presence, level, and/or activity of metabolites of between 5 and 100 types of microbes are measured. In some embodiments, the presence, level, and/or activity of metabolites of between 100 and 1000 or more types of microbes are measured. In other embodiments, the presence, level, and/or activity of metabolites of all types of bacteria within the microbiome are analyzed. In other embodiments, the presence, level, and/or activity of metabolites of all microbes within the microbiome are measured.

In some embodiments, only metabolites which fulfill the below two criteria are measured.
  (i) their level is altered during a prior weight gain period of the subject to reach a level representative of an obese subject; and
  (ii) the metabolite is retained at the level representative of the obese subject following the weight loss program (e.g. does not change more than 1%, 2%, 3%, 4%, 5%, 6%, 7%, 8%, 9% or 10% in either direction).

In still other embodiments, the majority of metabolites which are measured fulfill the two criteria set forth herein above.

As used herein, a "metabolite" is an intermediate or product of metabolism. The term metabolite is generally restricted to small molecules and does not include polymeric compounds such as DNA or proteins. A metabolite may serve as a substrate for an enzyme of a metabolic pathway, an intermediate of such a pathway or the product obtained by the metabolic pathway.

According to a particular embodiment, the metabolite is one that alters the composition or function of the microbiome.

In preferred embodiments, metabolites include but are not limited to sugars, organic acids, amino acids, fatty acids, hormones, vitamins, oligopeptides (less than about 100 amino acids in length), as well as ionic fragments thereof. Cells can also be lysed in order to measure cellular products present within the cell. In particular, the metabolites are less than about 3000 Daltons in molecular weight, and more particularly from about 50 to about 3000 Daltons.

The metabolite of this aspect of the present invention may be a primary metabolite (i.e. essential to the microbe for growth) or a secondary metabolite (one that does not play a role in growth, development or reproduction, and is formed during the end or near the stationary phase of growth.

Representative examples of metabolic pathways in which the metabolites of the present invention are involved include, without limitation, citric acid cycle, respiratory chain, photosynthesis, photorespiration, glycolysis, gluconeogenesis, hexose monophosphate pathway, oxidative pentose phosphate pathway, production and β-oxidation of fatty acids, urea cycle, amino acid biosynthesis pathways, protein degradation pathways such as proteasomal degradation, amino acid degrading pathways, biosynthesis or degradation of: lipids, polyketides (including, e.g., flavonoids and isoflavonoids), isoprenoids (including, e.g., terpenes, sterols, steroids, carotenoids, xanthophylls), carbohydrates, phenylpropanoids and derivatives, alkaloids, benzenoids, indoles, indole-sulfur compounds, porphyrines, anthocyans, hormones, vitamins, cofactors such as prosthetic groups or electron carriers, lignin, glucosinolates, purines, pyrimidines, nucleosides, nucleotides and related molecules such as tRNAs, microRNAs (miRNA) or mRNAs.

Representative examples of metabolites that may be analyzed according to this aspect of the present invention include, but are not limited to bile acid components such as ursodeoxycholate, glycocholate, phenylacetate and heptanoate and flavonoids such as apigenin and naringenin.

In some embodiments, levels of metabolites are determined by mass spectrometry, as further described herein below. In some embodiments, levels of metabolites are determined by nuclear magnetic resonance spectroscopy, as further described herein below. In some embodiments, levels of metabolites are determined by enzyme-linked immunosorbent assay (ELISA). In some embodiments, levels of metabolites are determined by colorimetry. In some embodiments, levels of metabolites are determined by spectrophotometry, as further described herein below.

Quantifying Metabolite Levels:

In one embodiment, metabolites are identified using a physical separation method.

The term "physical separation method" as used herein refers to any method known to those with skill in the art sufficient to produce a profile of changes and differences in small molecules produced in hSLCs, contacted with a toxic, teratogenic or test chemical compound according to the methods of this invention. In a preferred embodiment, physical separation methods permit detection of cellular metabolites including but not limited to sugars, organic acids, amino acids, fatty acids, hormones, vitamins, and oligopeptides, as well as ionic fragments thereof and low molecular weight compounds (preferably with a molecular weight less than 3000 Daltons, and more particularly between 50 and 3000 Daltons). For example, mass spectrometry can be used. In particular embodiments, this analysis is performed by liquid chromatography/electrospray ionization time of flight mass spectrometry (LC/ESI-TOF-MS), however it will be understood that metabolites as set forth herein can be detected using alternative spectrometry methods or other methods known in the art for analyzing these types of compounds in this size range.

Certain metabolites can be identified by, for example, gene expression analysis, including real-time PCR, RT-PCR, Northern analysis, and in situ hybridization.

In addition, biomarkers can be identified using Mass Spectrometry such as MALDI/TOF (time-of-flight), SELDL/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, tandem mass spectrometry (e.g., MS/MS, MS/MS/MS, ESI-MS/MS etc.), secondary ion mass spectrometry (SIMS), or ion mobility spectrometry (e.g. GC-IMS, IMS-MS, LC-IMS, LC-IMS-MS etc.).

Mass spectrometry methods are well known in the art and have been used to quantify and/or identify biomolecules, such as proteins and other cellular metabolites (see, e.g., Li et al., 2000; Rowley et al., 2000; and Kuster and Mann, 1998).

In certain embodiments, a gas phase ion spectrophotometer is used. In other embodiments, laser-desorption/ionization mass spectrometry is used to identify metabolites. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI").

In MALDI, the metabolite is mixed with a solution containing a matrix, and a drop of the liquid is placed on the surface of a substrate. The matrix solution then co-crystallizes with the biomarkers. The substrate is inserted into the mass spectrometer. Laser energy is directed to the substrate surface where it desorbs and ionizes the proteins without significantly fragmenting them. However, MALDI has limitations as an analytical tool. It does not provide means for fractionating the biological fluid, and the matrix material can interfere with detection, especially for low molecular weight analytes.

In SELDI, the substrate surface is modified so that it is an active participant in the desorption process. In one variant, the surface is derivatized with adsorbent and/or capture reagents that selectively bind the biomarker of interest. In another variant, the surface is derivatized with energy absorbing molecules that are not desorbed when struck with the laser. In another variant, the surface is derivatized with molecules that bind the biomarker of interest and that contain a photolytic bond that is broken upon application of the laser. In each of these methods, the derivatizing agent generally is localized to a specific location on the substrate surface where the sample is applied. The two methods can be combined by, for example, using a SELDI affinity surface to capture an analyte (e.g. biomarker) and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

In some embodiments, the data from mass spectrometry is represented as a mass chromatogram. A "mass chromatogram" is a representation of mass spectrometry data as a chromatogram, where the x-axis represents time and the y-axis represents signal intensity. In one aspect the mass chromatogram is a total ion current (TIC) chromatogram. In another aspect, the mass chromatogram is a base peak chromatogram. In other embodiments, the mass chromatogram is a selected ion monitoring (SIM) chromatogram. In yet another embodiment, the mass chromatogram is a selected reaction monitoring (SRM) chromatogram. In one embodiment, the mass chromatogram is an extracted ion chromatogram (EIC).

In an EIC, a single feature is monitored throughout the entire run. The total intensity or base peak intensity within a mass tolerance window around a particular analyte's mass-to-charge ratio is plotted at every point in the analysis. The size of the mass tolerance window typically depends on the mass accuracy and mass resolution of the instrument collecting the data. As used herein, the term "feature" refers to a single small metabolite, or a fragment of a metabolite. In some embodiments, the term feature may also include noise upon further investigation.

Detection of the presence of a metabolite will typically involve detection of signal intensity. This, in turn, can reflect the quantity and character of a biomarker bound to the substrate. For example, in certain embodiments, the signal strength of peak values from spectra of a first sample and a second sample can be compared (e.g., visually, by computer analysis etc.) to determine the relative amounts of particular metabolites. Software programs such as the Biomarker Wizard program (Ciphergen Biosystems, Inc., Fremont, Calif.) can be used to aid in analyzing mass spectra. The mass spectrometers and their techniques are well known.

A person skilled in the art understands that any of the components of a mass spectrometer, e.g., desorption source, mass analyzer, detect, etc., and varied sample preparations can be combined with other suitable components or preparations described herein, or to those known in the art. For example, in some embodiments a control sample may contain heavy atoms, e.g. $^{13}C$, thereby permitting the test sample to be mixed with the known control sample in the same mass spectrometry run. Good stable isotopic labeling is included.

In one embodiment, a laser desorption time-of-flight (TOF) mass spectrometer is used. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio.

In one embodiment of the invention, levels of metabolites are detected by MALDI-TOF mass spectrometry.

Methods of detecting metabolites also include the use of surface plasmon resonance (SPR). The SPR biosensing technology has been combined with MALDI-TOF mass spectrometry for the desorption and identification of metabolites.

Data for statistical analysis can be extracted from chromatograms (spectra of mass signals) using softwares for statistical methods known in the art. "Statistics" is the science of making effective use of numerical data relating to groups of individuals or experiments. Methods for statistical analysis are well-known in the art.

In one embodiment a computer is used for statistical analysis.

In one embodiment, the Agilent MassProfiler or MassProfilerProfessional software is used for statistical analysis. In another embodiment, the Agilent MassHunter software Qual software is used for statistical analysis. In other embodiments, alternative statistical analysis methods can be used. Such other statistical methods include the Analysis of Variance (ANOVA) test, Chi-square test, Correlation test, Factor analysis test, Mann-Whitney U test, Mean square weighted derivation (MSWD), Pearson product-moment correlation coefficient, Regression analysis, Spearman's rank correlation coefficient, Student's T test, Welch's T-test, Tukey's test, and Time series analysis.

In different embodiments, signals from mass spectrometry can be transformed in different ways to improve the performance of the method. Either individual signals or summaries of the distributions of signals (such as mean, median or variance) can be so transformed. Possible transformations include taking the logarithm, taking some positive or negative power, for example the square root or inverse, or taking the arcsin (Myers, Classical and Modem Regression with Applications, 2nd edition, Duxbury Press, 1990).

In one embodiment, the method is carried out by analyzing the microbes of the microbiome of the subject and comparing its microbial composition to the microbial composition of a microbiome of a non-obese subject who has not undergone a weight loss program. When the two microbiomes have a statistically significant similar signature, then the likelihood of gaining weight is reduced as compared to a subject having a microbiome which is not statistically significantly similar to that of the non-obese subject who has not undergone a weight loss program.

In another embodiment, the method is carried out by analyzing the metabolites of the metabolome of the subject and comparing its metabolite composition to the metabolite composition of a metabolome of a non-obese subject who has not undergone a weight loss program. When the two metabolomes have a statistically significant similar signature, then the likelihood of gaining weight is reduced as compared to a subject having a metabolome which is not statistically significantly similar to that of the non-obese subject who has not undergone a weight loss program.

The present embodiments encompass the recognition that microbial signatures can be relied upon as proxy for microbiome composition and/or activity. Microbial signatures comprise data points that are indicators of microbiome composition and/or activity. Thus, according to the present invention, changes in microbiomes can be detected and/or analyzed through detection of one or more features of microbial signatures.

In some embodiments, a microbial signature includes information relating to absolute amount of one or more types of microbes, and/or products thereof. In some embodiments, a microbial signature includes information relating to relative amounts of five, ten, twenty, fifty, one hundred or more types of microbes and/or products thereof.

In other embodiments, the microbial signature of the gut microbiome comprises a microbe diversity.

In other embodiments, the microbial signature of the gut microbiome comprises metabolite signature.

In other embodiments, the microbial signature of the gut microbiome comprises a bacterial signature.

Preferably, the signature comprises at least 1, 5, 10, 20, 30, 40, 50, 60, 70, 80, 90, 100, 150, 200, 250, 300 microbes or products thereof that fulfill the two criteria set forth herein above.

According to one embodiment of this aspect of the present invention two microbiome signatures can be have a statistically significant similar signature when they comprise at least 50% of the same microbes, at least 60% of the same microbes, at least 70% of the same microbes, at least 80% of the same microbes, at least 90% of the same microbes, at least 91% of the same microbes, at least 92% of the same microbes, at least 93% of the same microbes, at least 94% of the same microbes, at least 95% of the same microbes, at least 96% of the same microbes, at least 97% of the same microbes, at least 98% of the same microbes, at least 99% of the same microbes or 100% of the same microbes.

Additionally, or alternatively, microbiomes may have a statistically significant similar signature when the quantity (e.g. occurrence) in the microbiome of at least one microbe of interest is identical. According to another embodiment, microbiomes may have a statistically significant similar signature when the relative ratio in the microbiome of at least 10% of its microbes are identical. According to another embodiment, microbiomes may have a statistically significant similar signature when the relative ratio in the microbiome of at least 20% of its microbes are identical.

According to another embodiment, microbiomes may have a statistically significant similar signature when the relative ratio in the microbiome of at least 30% of its microbes are identical. According to another embodiment, microbiomes may have a statistically significant similar signature when the relative ratio in the microbiome of at least 40% of its microbes are identical. According to another embodiment, microbiomes may have a statistically significant similar signature when the relative ratio in the microbiome of at least 50% of its microbes are identical.

According to another embodiment, microbiomes may have a statistically significant similar signature when the relative ratio in the microbiome of at least 60% of its microbes are identical. According to another embodiment, microbiomes may have a statistically significant similar signature when the relative ratio in the microbiome of at least 70% of its microbes are identical. According to another embodiment, microbiomes may have a statistically significant similar signature when the relative ratio in the microbiome of at least 80% of its microbes are identical.

According to another embodiment, microbiomes may have a statistically significant similar signature when the relative ratio in the microbiome of at least 90% of its microbes are identical. Thus, the fractional percentage of microbes (e.g. relative amount, ratio, distribution, frequency, percentage, etc.) of the total may be statistically similar.

According to another embodiment, in order to classify a microbe as belonging to a particular genus, family, order, class or phylum, it must comprise at least 90% sequence homology, at least 91% sequence homology, at least 92% sequence homology, at least 93% sequence homology, at least 94% sequence homology, at least 95% sequence homology, at least 96% sequence homology, at least 97% sequence homology, at least 98% sequence homology, at least 99% sequence homology to a reference microbe known to belong to the particular genus. According to a particular embodiment, the sequence homology is at least 95%.

According to another embodiment, in order to classify a microbe as belonging to a particular species, it must comprise at least 90% sequence homology, at least 91% sequence homology, at least 92% sequence homology, at least 93% sequence homology, at least 94% sequence homology, at least 95% sequence homology, at least 96% sequence homology, at least 97% sequence homology, at least 98% sequence homology, at least 99% sequence homology to a reference microbe known to belong to the particular species. According to a particular embodiment, the sequence homology is at least 97%.

In determining whether a nucleic acid or protein is substantially homologous or shares a certain percentage of sequence identity with a sequence of the invention, sequence similarity may be defined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215:403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See www(dot)ncbi(dot)nlm(dot)nih(dot)gov for more details.

According to still another embodiment, two microbiome signatures can be classified as being similar, if the relative number of genes belonging to a particular pathway is similar.

According to still another embodiment, two microbiome signatures can be classified as being similar, if the relative amount of a product generated by the microbes is similar.

The prediction of this aspect of the present invention may be made using an algorithm (e.g. a machine learning algorithm) which takes into account the relevance (i.e. weight) of particular microbes and/or products thereof in the composition. The algorithm may be built using gut microbiome data of a population of subjects classified according to their dietary state (e.g. a classification of non-obese, non dieting subjects, a classification of obese subjects and a classification of non-obese, post-dieting subjects).

The database may include other parameters relating to the subjects, for example the weight of the subject, the blood chemistry of the subject, the genetic profile of the subject, the BMI of the subject, the eating habits of the subject and/or the health of the subject (e.g. diabetic, pre-diabetic, other metabolic disorder, hypertension, cardiac disorder etc.).

As used herein the term "machine learning" refers to a procedure embodied as a computer program configured to induce patterns, regularities, or rules from previously collected data to develop an appropriate response to future data, or describe the data in some meaningful way.

Use of machine learning is particularly, but not exclusively, advantageous when the database includes multidimensional entries.

The database can be used as a training set from which the machine learning procedure can extract parameters that best describe the dataset. Once the parameters are extracted, they can be used to predict the likelihood of weight regain in a subject.

In machine learning, information can be acquired via supervised learning or unsupervised learning. In some embodiments of the invention the machine learning procedure comprises, or is, a supervised learning procedure. In supervised learning, global or local goal functions are used to optimize the structure of the learning system. In other words, in supervised learning there is a desired response, which is used by the system to guide the learning.

In some embodiments of the invention the machine learning procedure comprises, or is, an unsupervised learning procedure. In unsupervised learning there are typically no goal functions. In particular, the learning system is not provided with a set of rules. One form of unsupervised learning according to some embodiments of the present invention is unsupervised clustering in which the data objects are not class labeled, a priori.

Representative examples of "machine learning" procedures suitable for the present embodiments, including, without limitation, clustering, association rule algorithms, feature evaluation algorithms, subset selection algorithms, support vector machines, classification rules, cost-sensitive classifiers, vote algorithms, stacking algorithms, Bayesian networks, decision trees, neural networks, instance-based algorithms, linear modeling algorithms, k-nearest neighbors analysis, ensemble learning algorithms, probabilistic models, graphical models, regression methods, gradient ascent methods, singular value decomposition methods and principle component analysis. Among neural network models, the self-organizing map and adaptive resonance theory are commonly used unsupervised learning algorithms. The adaptive resonance theory model allows the number of clusters to vary with problem size and lets the user control the degree of similarity between members of the same clusters by means of a user-defined constant called the vigilance parameter.

Following is an overview of some machine learning procedures suitable for the present embodiments.

Association rule algorithm is a technique for extracting meaningful association patterns among features.

The term "association", in the context of machine learning, refers to any interrelation among features, not just ones that predict a particular class or numeric value. Association includes, but it is not limited to, finding association rules, finding patterns, performing feature evaluation, performing feature subset selection, developing predictive models, and understanding interactions between features.

The term "association rules" refers to elements that co-occur frequently within the databases. It includes, but is not limited to association patterns, discriminative patterns, frequent patterns, closed patterns, and colossal patterns.

A usual primary step of association rule algorithm is to find a set of items or features that are most frequent among all the observations. Once the list is obtained, rules can be extracted from them.

The aforementioned self-organizing map is an unsupervised learning technique often used for visualization and analysis of high-dimensional data. Typical applications are focused on the visualization of the central dependencies within the data on the map. The map generated by the algorithm can be used to speed up the identification of association rules by other algorithms. The algorithm typically includes a grid of processing units, referred to as "neurons". Each neuron is associated with a feature vector referred to as observation. The map attempts to represent all the available observations with optimal accuracy using a restricted set of models. At the same time the models become ordered on the grid so that similar models are close to each other and dissimilar models far from each other. This procedure enables the identification as well as the visualization of dependencies or associations between the features in the data.

Feature evaluation algorithms are directed to the ranking of features or to the ranking followed by the selection of features based on their impact on the likelihood of the subject under analysis to regain weight.

The term "feature" in the context of machine learning refers to one or more raw input variables, to one or more processed variables, or to one or more mathematical combinations of other variables, including raw variables and processed variables. Features may be continuous or discrete.

Information gain is one of the machine learning methods suitable for feature evaluation. The definition of information gain requires the definition of entropy, which is a measure of impurity in a collection of training instances. The reduction in entropy of the target feature that occurs by knowing the values of a certain feature is called information gain. Information gain may be used as a parameter to determine the effectiveness of a feature in explaining the likelihood of the subject under analysis to regain weight. Symmetrical uncertainty is an algorithm that can be used by a feature selection algorithm, according to some embodiments of the present invention. Symmetrical uncertainty compensates for information gain's bias towards features with more values by normalizing features to a [0,1] range.

Subset selection algorithms rely on a combination of an evaluation algorithm and a search algorithm. Similarly to feature evaluation algorithms, subset selection algorithms rank subsets of features. Unlike feature evaluation algorithms, however, a subset selection algorithm suitable for the present embodiments aims at selecting the subset of features with the highest impact on the likelihood of the subject under analysis to regain weight, while accounting for the degree of redundancy between the features included in the subset. The benefits from feature subset selection include facilitating data visualization and understanding, reducing measurement and storage requirements, reducing training and utilization times, and eliminating distracting features to improve classification.

Two basic approaches to subset selection algorithms are the process of adding features to a working subset (forward selection) and deleting from the current subset of features (backward elimination). In machine learning, forward selection is done differently than the statistical procedure with the same name. The feature to be added to the current subset in machine learning is found by evaluating the performance of the current subset augmented by one new feature using cross-validation. In forward selection, subsets are built up by adding each remaining feature in turn to the current subset while evaluating the expected performance of each new subset using cross-validation. The feature that leads to the best performance when added to the current subset is retained and the process continues. The search ends when none of the remaining available features improves the predictive ability of the current subset. This process finds a local optimum set of features.

Backward elimination is implemented in a similar fashion. With backward elimination, the search ends when further reduction in the feature set does not improve the predictive ability of the subset. The present embodiments contemplate search algorithms that search forward, backward or in both directions. Representative examples of search algorithms suitable for the present embodiments include, without limitation, exhaustive search, greedy hill-climbing, random perturbations of subsets, wrapper algorithms, probabilistic race search, schemata search, rank race search, and Bayesian classifier.

A decision tree is a decision support algorithm that forms a logical pathway of steps involved in considering the input to make a decision.

The term "decision tree" refers to any type of tree-based learning algorithms, including, but not limited to, model trees, classification trees, and regression trees.

A decision tree can be used to classify the databases or their relation hierarchically. The decision tree has tree structure that includes branch nodes and leaf nodes. Each branch node specifies an attribute (splitting attribute) and a test (splitting test) to be carried out on the value of the splitting attribute, and branches out to other nodes for all possible outcomes of the splitting test. The branch node that is the root of the decision tree is called the root node. Each leaf node can represent a classification (e.g., whether a particular portion of the group database matches a particular portion of the subject-specific database) or a value (e.g., a predicted the likelihood of the subject under analysis to regain weight). The leaf nodes can also contain additional information about the represented classification such as a confidence score that measures a confidence in the represented classification (i.e., the likelihood of the classification being accurate). For example, the confidence score can be a continuous value ranging from 0 to 1, which a score of 0 indicating a very low confidence (e.g., the indication value of the represented classification is very low) and a score of 1 indicating a very high confidence (e.g., the represented classification is almost certainly accurate).

Support vector machines are algorithms that are based on statistical learning theory. A support vector machine (SVM) according to some embodiments of the present invention can be used for classification purposes and/or for numeric prediction. A support vector machine for classification is referred to herein as "support vector classifier," support vector machine for numeric prediction is referred to herein as "support vector regression".

An SVM is typically characterized by a kernel function, the selection of which determines whether the resulting SVM provides classification, regression or other functions. Through application of the kernel function, the SVM maps input vectors into high dimensional feature space, in which a decision hyper-surface (also known as a separator) can be constructed to provide classification, regression or other decision functions. In the simplest case, the surface is a hyper-plane (also known as linear separator), but more complex separators are also contemplated and can be applied using kernel functions. The data points that define the hyper-surface are referred to as support vectors.

The support vector classifier selects a separator where the distance of the separator from the closest data points is as large as possible, thereby separating feature vector points associated with objects in a given class from feature vector points associated with objects outside the class. For support vector regression, a high-dimensional tube with a radius of acceptable error is constructed which minimizes the error of the data set while also maximizing the flatness of the associated curve or function. In other words, the tube is an envelope around the fit curve, defined by a collection of data points nearest the curve or surface.

An advantage of a support vector machine is that once the support vectors have been identified, the remaining observations can be removed from the calculations, thus greatly reducing the computational complexity of the problem. An SVM typically operates in two phases: a training phase and a testing phase. During the training phase, a set of support vectors is generated for use in executing the decision rule. During the testing phase, decisions are made using the decision rule. A support vector algorithm is a method for training an SVM. By execution of the algorithm, a training set of parameters is generated, including the support vectors that characterize the SVM. A representative example of a support vector algorithm suitable for the present embodiments includes, without limitation, sequential minimal optimization.

The Least Absolute Shrinkage and Selection Operator (LASSO) algorithm is a shrinkage and/or selection algorithm for linear regression. The LASSO algorithm may minimizes the usual sum of squared errors, with a regularization, that can be an L1 norm regularization (a bound on the sum of the absolute values of the coefficients), an L2 norm regularization (a bound on the sum of squares of the coefficients), and the like. The LASSO algorithm may be associated with soft-thresholding of wavelet coefficients, forward stagewise regression, and boosting methods. The LASSO algorithm is described in the paper: Tibshirani, R, Regression Shrinkage and Selection via the Lasso, J. Royal. Statist. Soc B., Vol. 58, No. 1, 1996, pages 267-288, the disclosure of which is incorporated herein by reference.

A Bayesian network is a model that represents variables and conditional interdependencies between variables. In a Bayesian network variables are represented as nodes, and nodes may be connected to one another by one or more links. A link indicates a relationship between two nodes. Nodes typically have corresponding conditional probability tables that are used to determine the probability of a state of a node given the state of other nodes to which the node is connected. In some embodiments, a Bayes optimal classifier algorithm is employed to apply the maximum a posteriori hypothesis to a new record in order to predict the probability of its classification, as well as to calculate the probabilities from each of the other hypotheses obtained from a training set and to use these probabilities as weighting factors for future predictions about the likelihood of a subject to regain weight. An algorithm suitable for a search for the best Bayesian network, includes, without limitation, global score metric-based algorithm. In an alternative approach to building the network, Markov blanket can be employed. The Markov blanket isolates a node from being affected by any node outside its boundary, which is composed of the node's parents, its children, and the parents of its children.

Instance-based algorithms generate a new model for each instance, instead of basing predictions on trees or networks generated (once) from a training set.

The term "instance", in the context of machine learning, refers to an example from a database.

Instance-based algorithms typically store the entire database in memory and build a model from a set of records similar to those being tested. This similarity can be evaluated, for example, through nearest-neighbor or locally weighted methods, e.g., using Euclidian distances. Once a set of records is selected, the final model may be built using several different algorithms, such as the naive Bayes.

As well as predicting the likelihood of a subject to regain weight following a weight loss product, the present method may also be used to determine the efficacy of a dieting aid.

Thus, according to another aspect of the present invention there is provided a method of monitoring the efficacy of a dieting aid in a subject:

(a) treating the subject with a dieting aid; and
(b) analyzing for the presence or the level of at least one microbe and/or product thereof, wherein an amount of the at least one microbe or product thereof is altered during a prior weight gain period of the subject to reach a level representative of an obese subject and further wherein the amount of the at least one microbe is retained at the level following the weight loss program;
wherein the level or presence of the at least one microbe or product thereof is indicative of the efficacy of a dieting aid.

As used herein, the phrase "dieting aid" refers to an agent, procedure or activity which aids in weight reduction.

The dieting agent may be a food, a chemical, a nutraceutical, a pharmaceutical agent.

The procedure of this aspect of the present invention may be a surgical procedure.

An example of an activity of this aspect of the present invention is an exercise regime.

According to this aspect of the present invention, when there is an increase in the level (e.g. by at least 10%, 20%, 30%, 40%, 50%, 60%, 70%, 80%, 90% or more) of at least one microbe (and/or product thereof), which is down-regulated during a prior weight gain period of the subject to reach a level representative of an obese subject and wherein the microbe is retained at that level following the weight loss program, it is indicative that the dietary aid is efficacious.

According to this aspect of the present invention, when there is an increase (e.g. by at least 10%, 20%, 30%, 40%, 50%, 60%, 70%, 80%, 90% or more) in the level of at least 20 microbes (and/or products thereof), which are down-regulated during a prior weight gain period of the subject to reach a level representative of an obese subject and wherein the microbes are retained at that level following the weight loss program, it is indicative that the dietary aid is efficacious.

According to this aspect of the present invention, when there is an increase (e.g. by at least 10%, 20%, 30%, 40%, 50%, 60%, 70%, 80%, 90% or more) in the level of at least 50 microbes (and/or products thereof), which are down-regulated during a prior weight gain period of the subject to reach a level representative of an obese subject and wherein the microbes are retained at that level following the weight loss program, it is indicative that the dietary aid is efficacious.

According to this aspect of the present invention, when there is an increase (e.g. by at least 10%, 20%, 30%, 40%, 50%, 60%, 70%, 80%, 90% or more) in the level of at least 100 microbes (and/or products thereof), which are down-regulated during a prior weight gain period of the subject to reach a level representative of an obese subject and wherein the microbes are retained at that level following the weight loss program, it is indicative that the dietary aid is efficacious.

According to this aspect of the present invention, when there is a decrease (e.g. by at least 10%, 20%, 30%, 40%, 50%, 60%, 70%, 80%, 90% or more) in the level of at least one microbe (and/or product thereof), which is up-regulated during a prior weight gain period of the subject to reach a level representative of an obese subject and wherein the microbe is retained at that level following the weight loss program, it is indicative that the dietary aid is efficacious.

According to this aspect of the present invention, when there is a decrease (e.g. by at least 10%, 20%, 30%, 40%, 50%, 60%, 70%, 80%, 90% or more) in the level of at least 20 microbes (and/or products thereof), which are up-regulated during a prior weight gain period of the subject to reach a level representative of an obese subject and wherein the microbes are retained at that level following the weight loss program, it is indicative that the dietary aid is efficacious.

According to this aspect of the present invention, when there is a decrease (e.g. by at least 10%, 20%, 30%, 40%, 50%, 60%, 70%, 80%, 90% or more) in the level of at least 50 microbes (and/or products thereof), which are up-regulated during a prior weight gain period of the subject to reach a level representative of an obese subject and wherein the microbes are retained at that level following the weight loss program, it is indicative that the dietary aid is efficacious.

According to this aspect of the present invention, when there is a decrease (e.g. by at least 10%, 20%, 30%, 40%, 50%, 60%, 70%, 80%, 90% or more) in the level of at least 100 microbes (and/or products thereof), which are up-regulated during a prior weight gain period of the subject to reach a level representative of an obese subject and wherein the microbes are retained at that level following the weight loss program, it is indicative that the dietary aid is efficacious.

The present inventors further propose it is possible to reduce the risk of weight gain in a subject by administering to the subject agents that modulate his/her microbiome in a way such that his/her microbiome becomes more similar to a non-obese, non dieting subject.

Thus, according to another aspect of the present invention there is provided a method of reducing the risk of weight gain in a subject who has reached a target weight by practicing a weight loss program, the method comprising administering to the subject an agent which alters the gut microbiome of the subject so that a signature of the gut microbiome becomes more similar to a signature of a gut microbiome of a non-obese subject who has not undergone a weight loss program, thereby reducing weight gain in the subject.

According to one embodiment, the agent is one which up-regulates at least one microbe or product thereof (that is down-regulated during weight gain and remains down-regulated during subsequent weight loss).

Exemplary microbial compositions contemplated by the present inventors include those that are associated with nitrate synthesis and/or heptose biosynthesis.

For example, the present invention contemplates microbial compositions (e.g. probiotic compositions), which are derived from the gut microbiome of a healthy subject that is not overweight (e.g. has a BMI between 18.5-24.9) and further who has not undergone a weight loss program (e.g. in the last year, preferably last two years).

As used herein, the term "probiotic" refers to any microbial type that is associated with health benefits in a host organism and/or reduction of risk and/or symptoms of a disease, disorder, condition, or event in a host organism. In some embodiments, probiotics are formulated in a food product, functional food or nutraceutical. In some embodiments, probiotics are types of bacteria.

The microbial compositions of this aspect of the present invention may be statistically significantly similar to a microbiome of a non-obese subject who has not undergone a weight loss program (e.g. in the last year, preferably last two years).

The microbial compositions may be taken from a microbiota sample of the non-obese subject, who has not undergone a weight loss program.

A microbiota sample comprises a sample of microbes and or components or products thereof from a microbiome.

Alternatively, the microbial composition may be artificially created by adding known amounts of different microbes.

It will be appreciated that the microbial composition which is derived from the microbiota sample of a non-obese subject may be manipulated prior to administrating by increasing the amount of a particular strain or depleting the amount of a particular strain.

Alternatively, the microbial compositions are treated in such a way so as not to alter the relative balance between the microbial species and taxa comprised therein.

In some embodiments, the microbial composition is expanded ex vivo using known culturing methods prior to administration. In other embodiments, the microbial composition is not expanded ex vivo prior to administration.

According to one embodiment, the microbial composition is not derived from fecal material.

According to still another embodiment, the microbial composition is devoid (or comprises only trace quantities) of fecal material (e.g, fiber).

The probiotic microorganism may be in any suitable form, for example in a powdered dry form. In addition, the probiotic microorganism may have undergone processing in order for it to increase its survival. For example, the microorganism may be coated or encapsulated in a polysaccharide, fat, starch, protein or in a sugar matrix. Standard encapsulation techniques known in the art can be used. For example, techniques discussed in U.S. Pat. No. 6,190,591, which is hereby incorporated by reference in its entirety, may be used.

According to a particular embodiment, the probiotic microorganism composition is formulated in a food product, functional food or nutraceutical.

In some embodiments, a food product, functional food or nutraceutical is or comprises a dairy product. In some embodiments, a dairy product is or comprises a yogurt product. In some embodiments, a dairy product is or comprises a milk product.

In some embodiments, a dairy product is or comprises a cheese product. In some embodiments, a food product, functional food or nutraceutical is or comprises a juice or other product derived from fruit. In some embodiments, a food product, functional food or nutraceutical is or comprises a product derived from vegetables. In some embodiments, a food product, functional food or nutraceutical is or comprises a grain product, including but not limited to cereal, crackers, bread, and/or oatmeal. In some embodiments, a food product, functional food or nutraceutical is or comprises a rice product. In some embodiments, a food product, functional food or nutraceutical is or comprises a meat product.

As mentioned, the present inventors further propose administering metabolites of microbes as a proxy for the microbes themselves.

Exemplary metabolites that may be provided include, but are not limited to flavonoids, such as apigenin and/or naringenin.

Prior to administration of the probiotic or metabolite, the subject may be pretreated with an agent which reduces the number of naturally occurring microbes in the microbiome (e.g. by antibiotic treatment). According to a particular embodiment, the treatment significantly eliminates the naturally occurring gut microflora by at least 20%, 30% 40%, 50%, 60%, 70%, 80% or even 90%.

In still other embodiments, the agent is one which reduces ursodeoxycholate, glycocholate, phenylacetate and/or heptanoate.

According to another embodiment, the agent is one which down-regulates at least one microbe or product thereof(that is up-regulated during weight gain and remains down-regulated during subsequent weight loss).

Thus, the present inventors contemplate the use of antibiotic agents for preventing weight regain.

As used herein, the term "antibiotic agent" refers to a group of chemical substances, isolated from natural sources or derived from antibiotic agents isolated from natural sources, having a capacity to inhibit growth of, or to destroy bacteria. Examples of antibiotic agents include, but are not limited to; Amikacin; Amoxicillin; Ampicillin; Azithromycin; Azlocillin; Aztreonam; Aztreonam; Carbenicillin; Cefaclor, Cefepime; Cefetamet; Cefinetazole; Cefixime; Cefonicid; Cefoperazone; Cefotaxime; Cefotetan; Cefoxitin; Cefpodoxime; Cefprozil; Cefsulodin; Ceftazidime; Ceftizoxime; Ceftriaxone; Cefuroxime; Cephalexin; Cephalothin; Cethromycin; Chloramphenicol; Cinoxacin; Ciprofloxacin; Clarithromycin; Clindamycin; Cloxacillin; Co-amoxiclavuanate; Dalbavancin; Daptomycin; Dicloxacillin; Doxycycline; Enoxacin; Erythromycin estolate; Erythromycin ethyl succinate; Erythromycin glucoheptonate; Erythromycin lactobionate; Erythromycin stearate; Erythromycin; Fidaxomicin; Fleroxacin; Gentamicin; Imipenem; Kanamycin; Lomefloxacin; Loracarbef; Methicillin; Metronidazole; Mezlocillin; Minocycline; Mupirocin; Nafcillin; Nalidixic acid; Netilmicin; Nitrofurantoin; Norfloxacin; Ofloxacin; Oxacillin; Penicillin G; Piperacillin; Retapamulin; Rifaxamin, Rifampin; Roxithromycin; Streptomycin; Sulfamethoxazole; Teicoplanin; Tetracycline; Ticarcillin; Tigecycline; Tobramycin; Trimethoprim; Vancomycin; combinations of Piperacillin and Tazobactam; and their various salts, acids, bases, and other derivatives. Antibacterial antibiotic agents include, but are not limited to, aminoglycosides, carbacephems, carbapenems, cephalosporins, cephamycins, fluoroquinolones, glycopeptides, lincosamides, macrolides, monobactams, penicillins, quinolones, sulfonamides, and tetracyclines.

In one embodiment, the antibiotic is a broad spectrum antibiotic (e.g. vancomycin, neomycin, ampicillin, and metronidazole).

In another embodiment, the antibiotic is a narrow spectrum antibiotic.

Antibacterial agents also include antibacterial peptides. Examples include but are not limited to abaecin; andropin; apidaecins; bombinin; brevinins; buforin II; CAP18; cecropins; ceratotoxin; defensins; dermaseptin; dermcidin; drosomycin; esculentins; indolicidin; LL37; magainin; maximum H5; melittin; moricin; prophenin; protegrin; and or tachyplesins.

According to particular embodiments, the antibiotic agent reduces an amount and/or activity of bacteria the class Mollicutes or of the order Bacteroidales.

It will be appreciated that the above described method for reducing the risk or weight regain may be effected in a personalized or non-personalized fashion. As a personalized therapy, the method includes a step of determining an amount or presence of at least one microbe and/or product thereof in a gut microbiome of the subject, wherein the amount of the at least one microbe is altered during a prior weight gain period of the subject to reach a level representative of an obese subject and further wherein the amount of the at least one microbe is retained at the level following the weight loss program.

The agents which are administered are tailored according to the results of the analysis, wherein an agent which up-regulates at least one microbe or product thereof which is down-regulated during the prior weight gain period is administered or an agent which down-regulates a microbe or product thereof which is up-regulated during the prior weight gain period is administered.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, C T (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hanies, B. D., and Higgins S. J., eds. (1985); "Transcription and Translation" Hames, B. D., and Higgins S. J., eds. (1984); "Animal Cell Culture" Freshney, R. 1., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, C A (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Mice: C57B1/6 mice were purchased from Harlan and allowed to acclimatize to the animal facility environment for 2 weeks before used for experimentation. Outbred Swiss Webster germ-free mice were born in the Weizmann Institute germ-free facility and routinely monitored for sterility. For fecal transplantation experiments, 100 mg of stool was resuspended in 1 ml of PBS, homogenized, and filtered through a 70 µm strainer.

Recipient mice were gavaged with 200 µl of the filtrate.

In all experiments, age-matched male mice were used. Mice were 8 weeks of age at the beginning of experiments. For antibiotic treatment, mice were given a combination of vancomycin (1 g/l), ampicillin (1 g/l), kanamycin (1 g/l), and metronidazole (1 g/l) in their drinking. All antibiotics were obtained from Sigma Aldrich and given for the indicated time periods.

Stool samples were collected fresh and on the basis of individual mice. Fresh stool samples were collected into tubes, immediately frozen in liquid nitrogen upon collection, and stored at −80° C. until DNA isolation.

All experimental procedures were approved by the local IACUC.

Glucose tolerance test: Mice were fasted for 6 hours and subsequently given 200 µl of a 0.2 g/ml glucose solution (JT Baker) by oral gavage. Blood glucose was determined at 0, 15,30,60,90, and 120 minutes after glucose challenge (Contour™ blood glucose meter, Bayer, Switzerland).

Magnetic resonance imaging: Mice were anesthetized with isofluorane (5% for induction, 1-2% for maintenance) mixed with oxygen (1 liter/min) and delivered through a nasal mask. Once anesthetized, the animals were placed in a head-holder to assure reproducible positioning inside the magnet. Respiration rate was monitored and kept throughout the experimental period around 60-80 breaths per minute. MRI experiments were performed on 9.4 Tesla BioSpec Magnet 94/20 USR system (Bruker, Germany) equipped with gradient coils system capable of producing pulse gradient of up to 40 gauss/cm in each of the three directions. All MR images were acquired with a quadrature resonator coil (Bruker). The MRI protocol included two sets of coronal and axial multi-slices T2-weighted MR images. The T2-weighted images were acquired using the multi-slice RARE sequence (TR=2500 ms, TE=35 ms, RARE factor=8), with matrix size being 256×256, four averages, corresponding to an image acquisition time of 2 min 40 sec per set. The first set was used to acquire 21 axial slices with 1.00 mm slice thickness (no gap). The field of view was selected with 4.2×4.2 cm². The second set was used to acquire 17 coronal slices with 1.00 mm slice thickness (no gap). The field of view was selected with 7.0×5.0 cm².

Total fat and lean mass of mice were measured by EchoMRI-100™ (Echo Medical Systems, Houston, TX).

Metabolic measurements: Food intake and locomotor activity were measured using the PhenoMaster system (TSE-Systems, Bad Homburg, Germany), which consists of a combination of sensitive feeding sensors for automated measurement and a photobeam-based activity monitoring system detects and records ambulatory movements, including rearing and climbing, in each cage. All parameters were measured continuously and simultaneously. Mice were trained singly-housed in identical cages prior to data acquisition.

Glucose, triglycerides, total cholesterol and high density lipoprotein (HDL) levels were measured in mouse serum by SpotChem EZ Chemistry Analyzer (Arkray, Japan).

Concentrations of leptin (Mouse Leptin DUO set, R&D Systems) and insulin (Ultra-sensitive mouse insulin ELISA kit, Crystal Chem) in the serum were measured using ELISA according to the manufacturer's instructions.

Flow cytometry: The stromal-vascular fraction of visceral white adipose tissue was obtained. The isolated cells were washed with cold PBS and resuspended in PBS containing 1% BSA for direct cell surface staining. Single-cell suspensions were stained with antibodies for 30 min on ice against CD45, F4/80, CD11b, TCRP, and NK1.1 (all obtained from Biolegend). Stained cells were analyzed on a BD-LSR-Fortessa cytometer and were analyzed with FlowJo software.

Taxonomic Microbiota Analysis: Frozen fecal samples were processed for DNA isolation using the MoBio Power-Soil kit according to the manufacturer's instructions. For the 16S rRNA gene PCR amplification, lng of the purified fecal DNA was used for PCR amplification. Amplicons spanning the variable region 1/2 (V1/2) of the 16S rRNA gene were generated by using the following barcoded primers: Fwd 5'-XXXXXXXXAGAGTTTGATCCTGGCTCAG-3' (SEQ ID NO: 1), Rev 5'-TGCTGCCTCCCGTAGGAGT-3' (SEQ ID NO: 2), where X represents a barcode base. The reactions were subsequently pooled and cleaned (PCR clean kit, Promega), and the PCR products were then sequenced on an Illumina MiSeq in 500 bp paired-end method. The reads were then processed using the QIIME (Quantitative Insights Into Microbial Ecology, www(dot)qiime(dot)org) analysis pipeline as described Caporaso, J. G. et al. Nature methods 7, 335-336, doi:10.1038/nmeth.f.303 (2010); Elinav, E. et al. Cell 145, 745-757, doi:10.1016/j.cell.2011.04.022 (2011). In brief, fasta quality files and a mapping file indicating the barcode sequence corresponding to each sample were used as inputs, reads were split by samples according to the barcode, taxonomical classification was performed using the RDP-classifier, and an OTU table was created. Closed-reference OTU mapping was employed using the Green-genes database. Rarefaction was used to exclude samples with insufficient count of reads per sample. Sequences sharing 97% nucleotide sequence identity in the V2 region were binned into operational taxonomic units (97% ID OTUs). For beta-diversity, weighted unifrac measurements were plotted according to the two principal coordinates based on 10,000 reads per sample. The OTU tables used for our analyses are made accessible online.

Metagenomic Sequence Mapping: Illumina sequencing reads were mapped to a gut microbial gene catalogue using GEM mapper[35] with the following parameters: -m 0:08—s 0-q offset33—gemqualitythreshold 26.

Functional Assignment: Reads mapped to the gut microbial gene catalog were assigned a KEGG[36,37]. Genes were subsequently mapped to KEGG modules and pathways. For the KEGG pathway analysis, only pathways whose gene coverage was above 0.2 were included. Bacterial assignment to metabolic pathways was done by mapping of metagenomic reads to genes from the respective metagenomic modules. Mapped reads were extracted and re-mapped to a bacterial genomes database. Reads that were successfully mapped were grouped into genera, and those not mapped were marked as 'unknowns'.

Metabolomics study: Fecal samples were collected, immediately frozen in liquid nitrogen and stored at −80° C. Sample preparation and analysis was performed by Metabolon Inc. Samples were prepared using the automated Micro-Lab STAR@ system from (Hamilton). To remove protein, dissociate small molecules bound to protein or trapped in the precipitated protein matrix, and to recover chemically diverse metabolites, proteins were precipitated with methanol. The resulting extract was divided into five fractions: one for analysis by UPLC-MS/MS with positive ion mode electrospray ionization, one for analysis by UPLC-MS/MS with negative ion mode electrospray ionization, one for LC polar platform, one for analysis by GC-MS, and one sample was reserved for backup. Samples were placed briefly on a TurboVap® (Zymark) to remove the organic solvent. For LC, the samples were stored overnight under nitrogen before preparation for analysis. For GC, each sample was dried under vacuum overnight before preparation for analysis.

Data Extraction and Compound Idendfication: Raw data was extracted, peak-identified and QC processed using Metabolon's hardware and software. Compounds were identified by comparison to library entries of purified standards or recurrent unknown entities. Metabolite Quantification and Data Normalization: Peaks were quantified using area-under-the-curve. For studies spanning multiple days, a data normalization step was performed to correct variation resulting from instrument inter-day tuning differences. Statistical analysis was done by Welch's two-sample t-test. For statistical significance testing, p-values are given and q-values for the level of 0.05 is the false positive rate.

Statistical Analysis: Data are expressed as mean f SEM. P-values $<0.05$ were considered significant. * $p<0.05$;  $p<0.01$; * $p<0.001$; **** $p<0.0001$. Comparisons between two groups were performed using two-tailed student's t test unless otherwise specified. Comparison between multiple groups was performed using ANOVA, and Mann-Whitney U-test was used to correct for multiple comparisons.

Classification of obesity history: Mouse obesity history was predicted using Random Forest Classification (sklearn 0.15.2) (Pedregosa et al., 2011) with the features being the relative abundances of 16S OTUs as outputted by QIIME. Classification was made in leave-one-out-cross validation.

Prediction of weight regain following HFD diet: Future weight gain of mice was predicted in leave-one-out-cross validation. For each held out mouse, a classifier of obesity history was first learned and used to classify the obesity history of the held out mouse as described above. Then, training data mice with the same obesity history as the held out mouse were taken, and gradient boosting regression (GBR, sklearn 0.15.2) was applied to learn a model that predicts their weight regain on the HFD diet. Input to this model consists of the 16S OTUs which were used within the GBR algorithm to predict weight regain.

Metagenomic analysis: The present inventors filtered metagenomic reads containing Illumina adapters, filtered low quality reads and trimmed low quality read edges. They detected host DNA by mapping with GEM (Marco-Sola et al., 2012) to the mouse genome with inclusive parameters, and removed those reads. They assigned length-normalized RA of genes, obtained by similar mapping with GEM to the reference catalog of (Li et al., 2014), to KEGG Orthology (KO) entries (Kanehisa and Goto, 2000), and these were then normalized to a sum of 1. They calculated RA of KEGG modules and pathways by summation. They considered only samples with >100K metagenomics reads.

Quality control of metagenomic reads and removal of host DNA: The present inventors applied Trimmomatic (Bolger et al., 2014) with the following parameters:

ILLUMINACLIP:<Trueseq3 adapters fasta file>:2:30:10 LEADING:25 TRAILING:25 MINLEN:50. They removed host DNA by mapping to the mouse genome (mm10, downloaded from www(dot)genome(dot)ucsc(dot)edu) and removed any mapped reads (see section below).

Mapping of metagenomic sequencing reads. Mapping was performed using the GEM mapper (Marco-Sola et al., 2012) with the following parameters:

q offset-33-gem-quality-threshold 26-m 0.1-e 0.1-min-matched-bases 0.8—max-big-indel-length 15-s 3-d'all'-D 1-v-T 2-p -E 0.3-max-extendable-matches 'all' —max-extensions-per-match 5;

with the addition of modifier:

m set to 0.05 for mapping to the mouse genome. Resulted mappings were retained as long as they had at least 50 matched bases with minimal quality of 26.

Genetic content relative abundance calculation. The present inventors mapped reads to the integrated reference catalog of the human gut microbiome (Xiao et al., 2014). For each gene in the catalog, they counted the fraction of reads mapped to it from each sample, normalized by gene length in kilobases. Reads mapping to more than one location were split so that each location received an equal fraction of the mapped read. They subsequently assigned mapped reads to KEGG Orthology (KO) entries (Kanehisa and Goto, 2000) using the gene annotation table available at www(dot)meta(dot)genomics(dot)cn/. They then calculated gene relative abundances by normalizing the KEGG genes of each sample to sum to 1. To calculate the abundances of KEGG pathways and modules, they summed the relative abundance of genes in each pathway and module.

Example 1

Enhanced recurrent weight gain after treatment of obesity

To study the mechanisms underlying post-dieting weight gain, a mouse model of relapsing obesity was used, in which mice were exposed to cycles of high-fat diet (HFD) feeding, intermitted by normal chow (NC) consumption (cycHFD). Consequently, in these mice, weight gain and features of the metabolic syndrome developed during exposure to HFD, followed by recuperation and weight reduction during exposure to NC, ensuing by a second cycle of HFD and associated metabolic derangements. As controls, mice continuously fed a HFD, mice continuously fed an NC diet and mice which were exposed to only a single cycle of HFD (primIFD) were used (FIG. 1A). As observed in recurrently dieting humans (3), a preceding obesity-weight loss cycle rendered mice susceptible to accelerated and enhanced secondary weight gain, even after fully returning to baseline weight (FIG. 1B). This relapsing obesity was characterized by an increase in total body fat as determined by MRI (FIGS. 1C-D), enhanced glucose intolerance as measured by an oral glucose tolerance test (FIGS. 1E-F), and elevated serum levels of leptin, total cholesterol, low-density lipoprotein (LDL), and triglycerides (FIGS. 1G-J) as compared to mice featuring a single identical HFD exposure.

Furthermore, exacerbated metabolic derangements following a weight gain/weight reduction cycle were similarly observed when weight loss was pharmacologically enhanced, as exemplified by experiments using celastrol, a quinone methide recently found to induce weight loss. In this model, weight gain induced by HFD consumption was followed by celastrol-mediated 'active dieting'). Upon reinstatement of HFD, mice developed exacerbated secondary weight gain (FIG. 1K), as compared to celastrol-treated controls without preceding obesity.

Figure 1J:
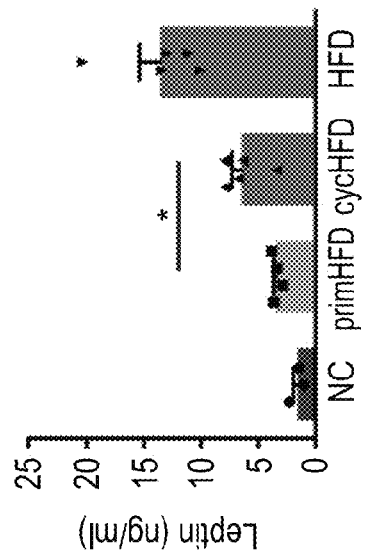
Figure 1I:
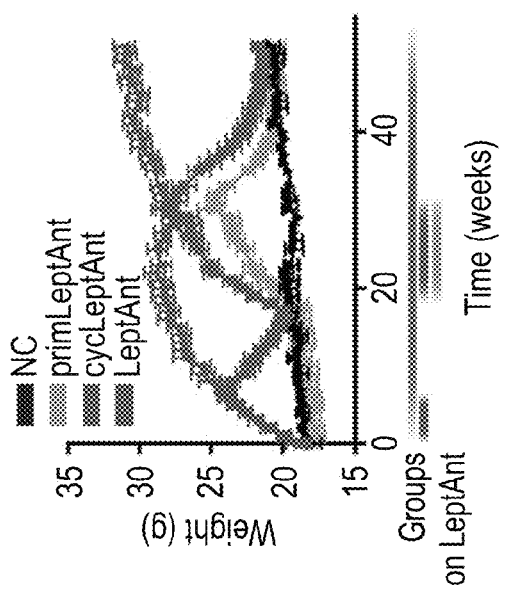
Figure 1K:
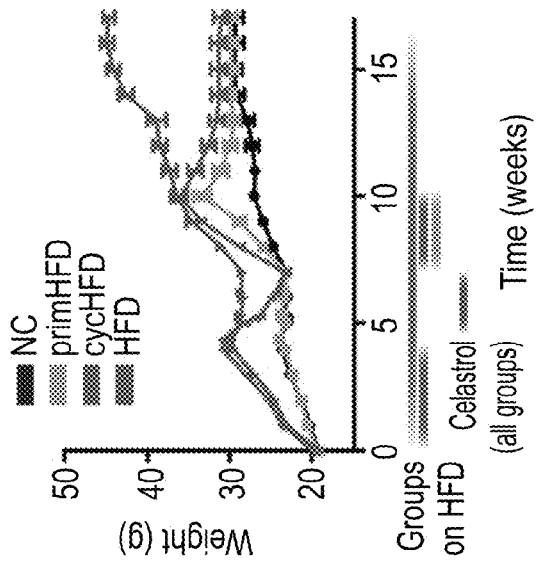

To rule out that this phenomenon was related to diet composition-related factors, rather than to the effect of post-obesity dieting, a different model of recurrent weight gain was employed, which utilized competitive inhibition of leptin signaling. The hyperactive leptin inhibitors were recently shown to alter peripheral leptin signaling and leptin transport into the central nervous system, thereby inducing an acquired and reversible state of leptin deficiency characterized by hyperphagia and weight gain even on normal chow diet (13). Indeed, mice which were injected with the leptin antagonist for one week while consuming NC significantly gained weight, and fully returned to normal weight upon cessation of leptin antagonist injection (FIG. 1J). As in the previous models, upon a second challenge by leptin antagonist, these mice featured enhanced weight regain as compared to mice on primary exposure to leptin antagonist (FIG. 1J). Together, these experiments demonstrate that a previous weight gain-dieting cycle enhances the susceptibility for a secondary weight gain and aggravated its associated metabolic complications, thus recapitulating the 'yo-yo effect' of recurrent post-dieting obesity.

Example 2

Persistence of a Memory-Like Microbiome Signature after Weight Loss

Since secondary weight gain was associated with enhanced metabolic derangements despite a full return to normal weight, it was hypothesized that initial obesity had caused persistent abnormalities that predisposed mice to relapsing metabolic disease upon re-feeding with HFD. The present inventors therefore performed metabolic profiling at the nadir phase, i.e. when previously obese mice had returned to their original weight. However, despite marked metabolic derangements during the obese phase, body fat content, glucose tolerance, and serum insulin levels were indistinguishable between post-dieting mice and their non-cycling controls (FIGS. 2A-D). Similarly, other hallmarks of obesity, such as physical activity, food and drink intake, oxygen consumption, energy expenditure, serum levels of leptin, and adipose tissue inflammation all returned to normal levels upon weight loss. In contrast, the composition of the intestinal microbiome, which had assumed a dysbiotic state during obesity, did not return to the original composition even following post-dieting weight and metabolic normalization, and featured an intermediate configuration between the dysbiotic and normal states (FIG. 2E). Likewise, bacterial diversity was lost during the obese state, but did not recover despite return to normal weight and metabolic homeostasis (FIG. 2F). The persistence of obesity-induced effects on the microbiome was driven by multiple bacterial taxa not returning to normal levels upon weight loss, including Mollicutes and Bacteroidales (FIGS. 2G-H). In addition, microbiome functionality, as determined by shotgun metagenomic sequencing, did not fully recover in previously dieting mice, both at the level of gene content (FIGS. 2I-J) and KEGG functionalities (FIGS. 2K-L). For instance, bacterial nitrate respiration and heptose biosynthesis were persistently abrogated in weight cycling mice (FIGS. 2K-L).

Such memory profiles were also observed in the microbiota of celastrol-treated mice, and in mice that had been administered leptin antagonist to induce weight cycling, indicating that the observed persistence effect of obesity-induced dysbiosis applies across various modes of weight gain and dieting.

Collectively, these data indicate that the microbiome exhibits a memory-like configuration upon reversal of obesity by dieting, even at a state when metabolic normality is reached.

Example 3

The Persistent Altered Microbiome Drives Exaggerated Recurrent Weight Gain

The present inventors next sought to investigate whether the post-obesity microbiome signature was causally involved in the metabolic complications associated with relapsing weight gain.

To this end, following a HFD consumption period, mice were treated with broad-spectrum antibiotics (vancomycin, neomycin, ampicillin, and metronidazole) during the following weight loss period (FIG. 3A). Notably, antibiotic treatment during dieting abolished the persistence of a post-obesity microbiome signature upon return to normal weight, as determined by 16S sequencing, and equilibrated the microbiota composition between previously obese mice and constantly lean controls (FIG. 3B). Remarkably, antibiotic treatment also abrogated the exacerbation of metabolic derangements upon weight regain, including body fat content and glucose intolerance, while control mice without antibiotics that were included in the same experiment showed enhanced metabolic aberrations in the second weight cycle (FIGS. 3B-F).

Figure 3G:
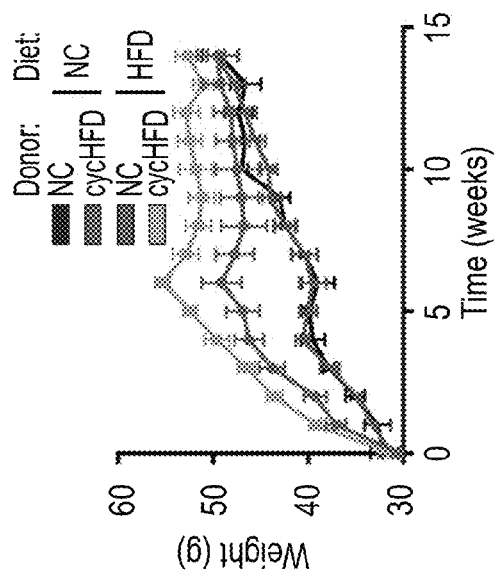
Figure 3H:
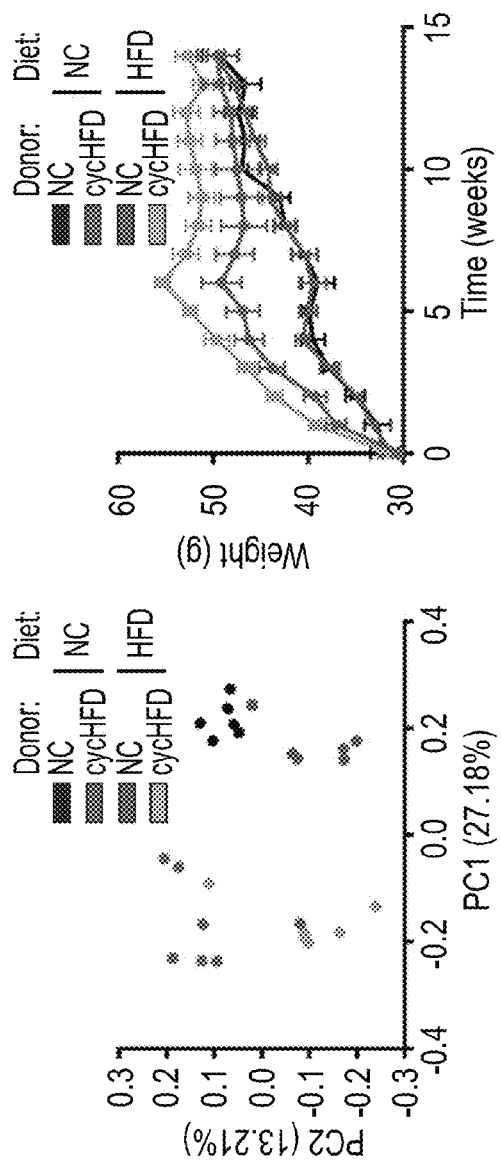
Figure 3I:
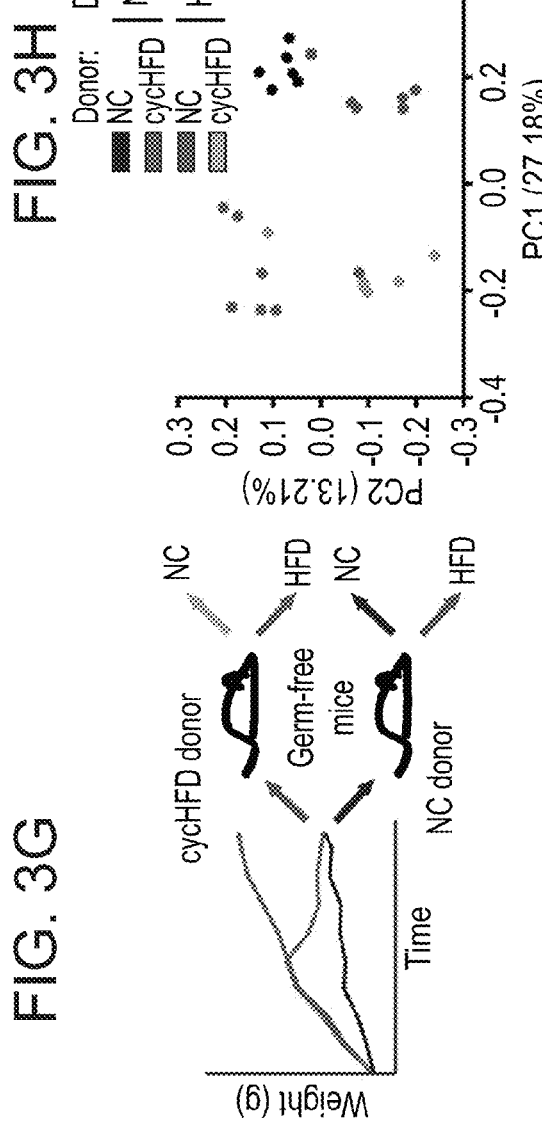
Figure 3J:
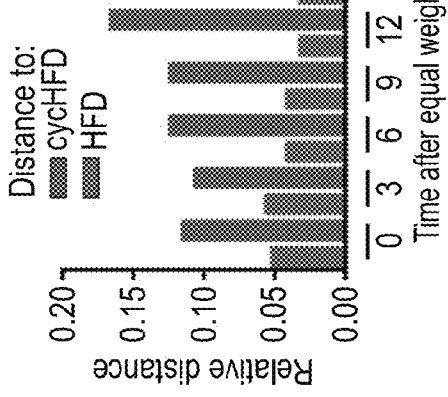

To further corroborate the causative role of the altered post-dieting microbiome in driving a secondary weight gain, fecal transplantation experiments were performed, in which the microbiota from previously obese mice (cycHFD) and from phenotypically identical controls (NC) was transferred to germ-free mice, which were subsequently fed either a NC diet or HFD (FIG. 3G). The compositional differences between the microbiota from formerly weight cycling mice and controls persisted in the germ-free recipients (FIG. 3L). Interestingly, under normal chow conditions, naïve and post-cycling microbiome-transplanted germ-free mice featured similar weight and glucose tolerance (FIGS. 3I, J), indicating that the post-obesity microbiome per se did not contain obesogenic properties. In contrast, when fed a HFD, recipients of post-weight cycling microbiota exhibited significantly enhanced weight gain and glucose intolerance compared to recipients of microbiome from control mice (FIGS. 3I, J). Thus, the germ-free recipients closely mirrored the phenotypes of the donor mice, demonstrating that the susceptibility to secondary weight gain can be transferred by means of fecal transplantation and induce enhanced metabolic derangements, even in the absence of a history of obesity. Together, these data suggest that the post-dieting microbiota is both necessary and sufficient to confer susceptibility to metabolic complications upon re-exposure to obesity-inducing conditions.

Figure 3K:
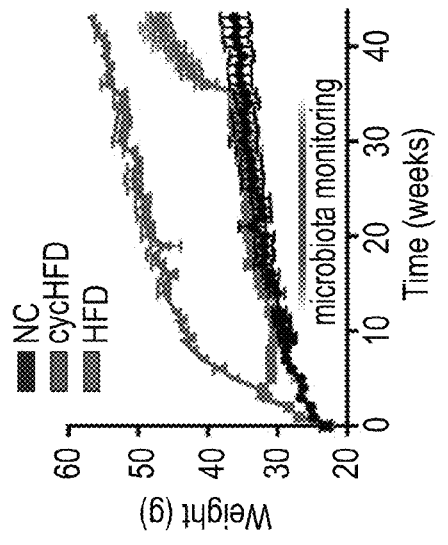
Figure 3L:
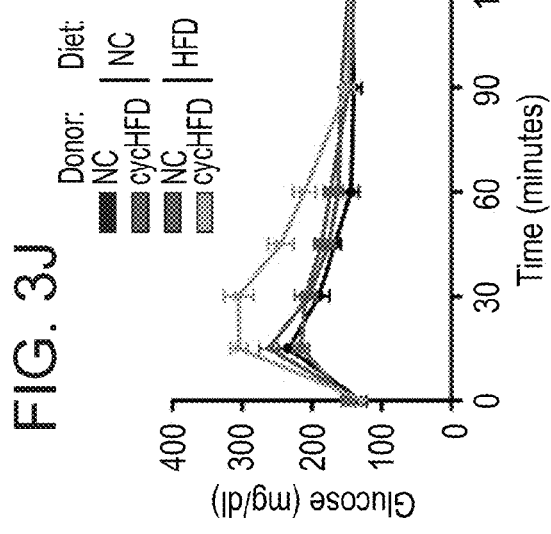

To determine the duration of persistence of the post-dieting microbiome alterations, the microbiota composition was monitored every three weeks upon return of previously weight cycling mice to phenotypic normality (FIG. 3K). Notably, only 21 weeks after weight equilibration, i.e. a time period more than five times longer than the initial weight gain or dieting period, the microbiota composition of formerly cycling mice became indistinguishable from that of age-matched lean mice (FIG. 3L). Notably, the full recovery of the microbiota composition was associated with ameliorated weight regain upon re-exposure to HFD (FIG. 3K). Together, these results demonstrate that following obesity and dieting, a long-lasting persistent microbiome configuration drives a marked tendency for exaggerated weight regain and associated metabolic disturbances induced by a second weight gain period Example 4

Accurate Prediction of Post-Dieting Weight Regain by Microbiota Parameters

Given the causal link between the persistently altered microbiome following cycling weight gain and dieting and the susceptibility to exacerbated secondary metabolic abnormalities, the present inventors next sought to develop a strategy to predict individual probabilities to undergo recurrent weight gain based on the microbiota composition at the post-dieting 'nadir" period. They therefore devised a machine-leaning algorithm which performs a two-step prediction of the extent of weight regain upon secondary exposure to HFD compared to primary exposure to HFD. In the first step, the fecal microbiomes from post-dieting 'ex-obese" mice are profiled in a manner that is blinded with respect to the history of obesity (FIG. 4A). These profiles are then used to predict the likelihood whether the fecal sample was obtained from a post-dieting or control mouse using a standard leave-out-out cross-validation scheme, which was carried out with very high true positive rate (ROC score 0.96, FIG. 4B). The microbiota profile is also used to predict the degree of weight gain upon exposure to HFD, which was achieved with considerable accuracy (R=0.58, FIG. 4C). In the second step, both inferred information about obesity history and predicted weight gain on HFD are integrated to achieve higher accuracy in weight gain prediction. In our cohort, this yielded a high correlation between predicted and measured weight gain upon HFD exposure (R=0.76, FIG. 4D).

To determine which features of the microbiota contribute to the algorithm's ability to predict the degree of weight gain, all operational taxonomic units (OTUs) detected in the fecal microbiomes were ranked according to feature importance for prediction (FIG. 4E). Of note, a total of 189 OTUs contributed to the algorithm's predictions, with modest relative contributions of each single OTU (FIG. 4E), indicating that a whole consortium of commensal bacteria, rather than a small group of species, drives the microbiome memory after dieting and the susceptibility to relapsing obesity. Among the 10 OTUs with the highest contribution to weight gain prediction were *Lactobacillus* spp. and the class of Mollicutes (FIG. 4F), both of which have reported associations with obesity (15, 16).

Together, these results indicate that persistent post-obesity structures in the microbiota can be used not only to infer the history of obesity, but to accurately predict the degree of weight regain upon recurrence of obesity-inducing conditions.

Example 5

Microbiome Modulation Ameliorates the Post-Dieting Weight Gain

Finally, the present inventors determined whether microbiome modulation during the post-weight cycling period can be employed to ameliorate the tendency for exaggerated weight gain and its metabolic complications. Several microbiome modulation approaches have been suggested, with various clinical efficacies. These include pro-biotic therapy involving exogenous introduction of commensal bacterial strains into an altered microbiome configuration (17), pre-biotic treatment involving dietary modulation of the microbiome (18), post-biotic intervention involving administration of combinations of microbiome-secreted or -modulated molecules that participate in host-microbiome interactions (19-21), and fecal microbiome transplantation (FMT) involving a total replacement of a disease-associated microbiome with a 'healthy' microbiome 22). Since one of the hallmarks of the post-weight cycling microbiota signature was persistently reduced bacterial diversity (FIG. 2F), the present inventors performed FMT during the 'nadir' post-dieting period, using 'naïve' or control post-dieting microbiomes as donors (FIG. 5A).

Notably, recipients of 'healthy' microbiota exhibited ameliorated secondary weight gain, which was indistinguishable from that of mice that were exposed to HFD for the first time (FIG. 5B). Recipients of 'non-cycling' microbiome also featured less body fat mass compared to mice undergoing a control FMT with 'cycling' microbiome (FIG. 5C). These results indicate that the restoration of normal microbiota function after dieting may prevent exacerbation of metabolic derangements upon weight regain.

Finally, given the effectiveness of FMT interventions, the present inventors sought to determine the mechanisms by which the microbiota predisposes to recurrent obesity after weight loss. They therefore compared the fecal metabolomes of mice undergoing diet-induced weight gain and return to normal weight to control mice that remained lean (FIG. 5D). Expectedly, HFD induced major alterations in the fecal metabolome. In the majority of cases, the levels of metabolites returned to normal upon weight loss. However, for a number of metabolites, the obesity-induced changes persisted after return to phenotypic normality (FIG. 5E). Among the obesity-induced persistent metabolites were the bile acid components ursodeoxycholate and glycocholate as well as phenylacetate and heptanoate. The metabolites depleted by HFD whose levels did not recover upon re-gain of metabolic health were the dietary flavonoids apigenin and naringenin (FIG. 5D), two compounds reported to influence food intake and adipocyte differentiation (23-26). It was hypothesized that FMT ameliorated relapsing obesity through supplementation of abrogated levels of apigenin and naringenin after dieting. The present inventors therefore orally administered both flavonoids to post-dieting mice when their weight and metabolic parameters had returned to normal levels. Remarkably, this metabolite treatment, similar to FMT, ameliorated secondary weight gain and metabolic complications (FIG. 5F). This effect was also achieved by administering naringenin alone. Taken together, these results suggest that metabolite treatment may restore the healthy function of the microbiome after dieting and thereby prevent the metabolic complications associated with weight regain and relapsing obesity.

Example 6

Enhanced Recurrent Weight Gain after Resolution of Obesity (Further to Example 1)

Figure 11C:
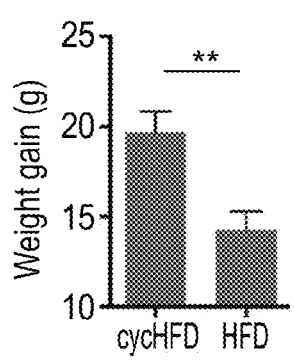
Figure 11D:
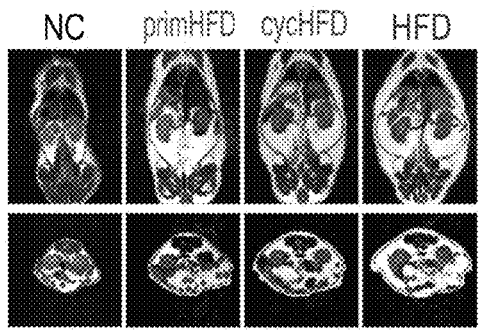
Figure 11E:
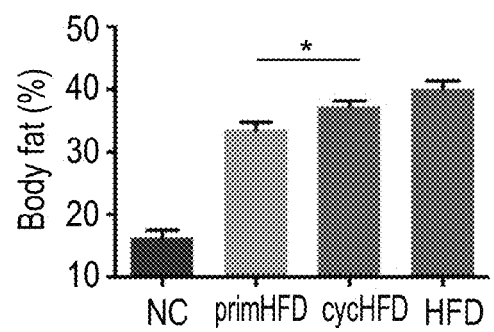
Figure 11F:
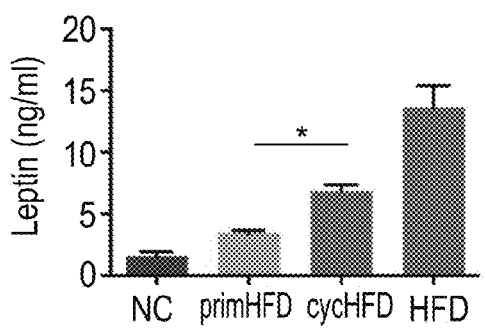
Figure 11G:
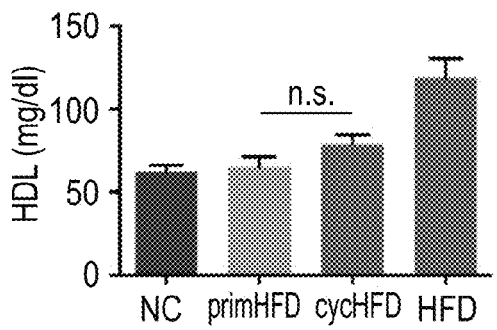
Figure 11H:
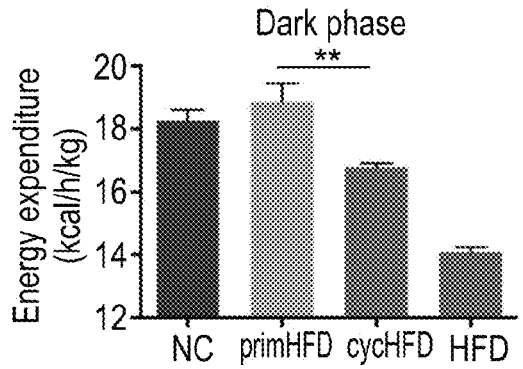
Figure 11I:
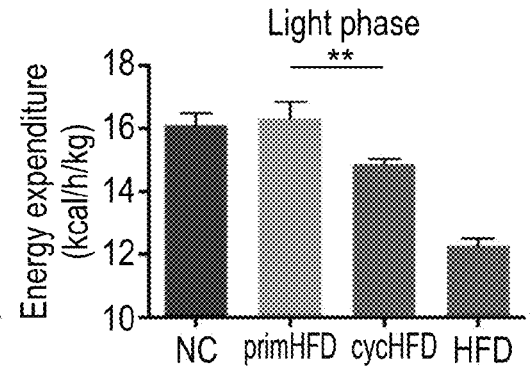

To study the mechanisms modulating post-dieting weight regain, a mouse model of recurrent obesity was utilized, in which mice were exposed to cycles of high-fat diet (HFD) feeding, interleaved by normal chow (NC) consumption (cycHFD, FIG. 1A). Consequently, in these mice, weight gain and metabolic syndrome developed during primary exposure to HFD, followed by recuperation and weight reduction during exposure to NC, and then by reemergence of weight gain and associated metabolic disturbances in subsequent HFD-mediated obesity cycles. As controls, mice continuously fed a HFD, mice continuously fed a NC diet, and mice that were exposed to only a single cycle of HFD (primHFD) were used (FIG. 1A). As observed in recurrently dieting humans, a preceding obesity-weight loss cycle rendered mice susceptible to accelerated secondary weight gain, even after fully returning to baseline weight (FIGS. 1B-C and FIGS. 11A-B). As a result, the net weight gain, i.e. the weight induced during identical durations of high-fat feeding, was higher in the weight cycling group as compared to mice continuously fed a HFD (FIG. 11C). The maximal weight reached by both weight cycling and continuous HFD groups was comparable, and higher than in mice exposed to a first cycle of HFD (FIG. 1B). Moreover, as compared to mice featuring a single HFD exposure, recurrent obesity was characterized by a significant increase in total body fat as determined by MRI (FIGS. 11D-E), enhanced glucose intolerance (FIGS. 1E-F), and elevated serum leptin (FIG. 11F) and low-density lipoprotein (LDL) levels (FIG. 1I), but not high-density lipoprotein (HDL) (FIG. 11G). Accelerated weight regain in post-dieting mice was associated with decreased energy expenditure (FIG. 6A and FIGS. 11H-O), while physical activity and food intake remained unaffected (FIGS. 11P-Q).

Figure 1L:
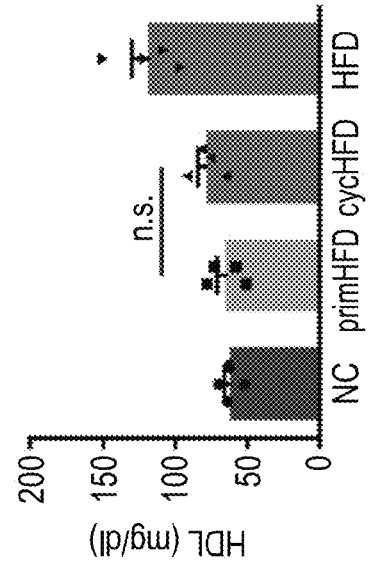

Similarly, exacerbated metabolic derangements following a weight gain/weight reduction cycle were observed when weight loss was pharmacologically enhanced by celastrol, a quinone methide recently found to induce weight loss[12] (FIGS. 12A-B). Upon reinstatement of HFD, mice developed significantly exacerbated secondary weight gain (FIGS. 12C-F), as compared to celastrol-treated controls without preceding obesity. Furthermore, to model recurrent obesity induced by hyperphagia rather than dietary composition, leptin signaling was pharmacologically-inhibited. Mice administered a leptin antagonist for one week while consuming NC significantly gained weight, and fully returned to normal weight upon cessation of leptin antagonist treatment. Upon a second challenge by leptin antagonist, these mice featured a more pronounced weight regain as compared to mice administered leptin antagonist for the first time (FIG. 1L and FIGS. 12G-H).

When exposed to a third cycle of HFD-induced obesity, weight cycling mice exhibited a further exacerbation in weight gain (FIG. 6B and FIG. 12I), obesity (FIG. 12J), and dyslipidemia (FIG. 12K) as compared to control animals experiencing secondary or primary weight gain cycles. Together, these experiments suggest that previous obesity-dieting cycles progressively enhance the susceptibility to accelerated weight regain and associated metabolic complications.

Example 7

Persistence of Obesity-Induced Microbiome Alterations after Weight Loss (Further to Example 2)

Given the above results, the present inventors hypothesized that initial obesity had caused persistent abnormalities that predisposed mice to relapsing metabolic disease upon re-feeding with HFD. They therefore performed metabolic profiling at the 'primary obesity' phase (FIG. 12L) and at the 'nadir' phase (FIG. 13A), i.e. when previously obese mice had returned to normal weight that was indistinguishable from that of NC-fed controls. Despite marked metabolic derangements during the primary obesity phase (FIGS. 12M-Q), neither body fat content, serum cholesterol, glucose tolerance, nor serum insulin levels were significantly different between post-dieting mice and their non-cycling controls during the 'nadir' post-obesity phase (FIGS. 13B-F). Similarly, other hallmarks of obesity, such as oxygen consumption, energy expenditure, physical activity, as well as food and drink intake fully returned to normal baseline levels upon weight loss during the 'nadir' phase (FIGS. 13G-L and FIGS. 14A-L).

Figure 7A:
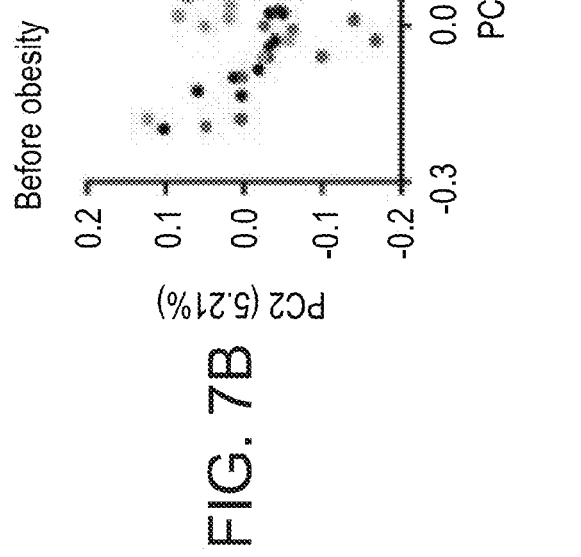
Figure 7B:
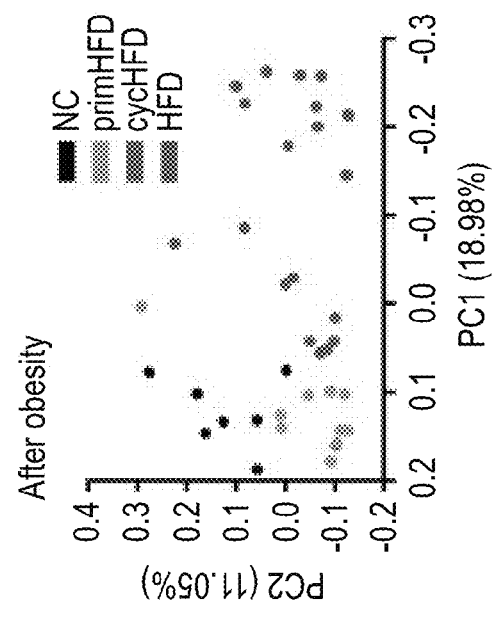
Figure 7C:
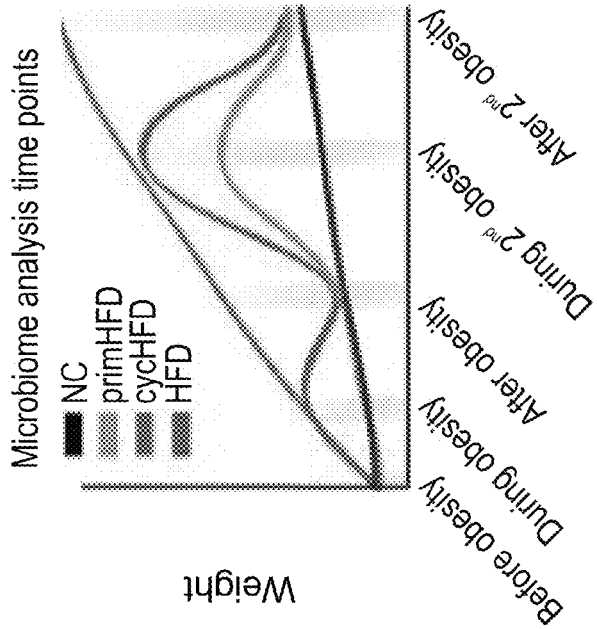
Figure 7D:
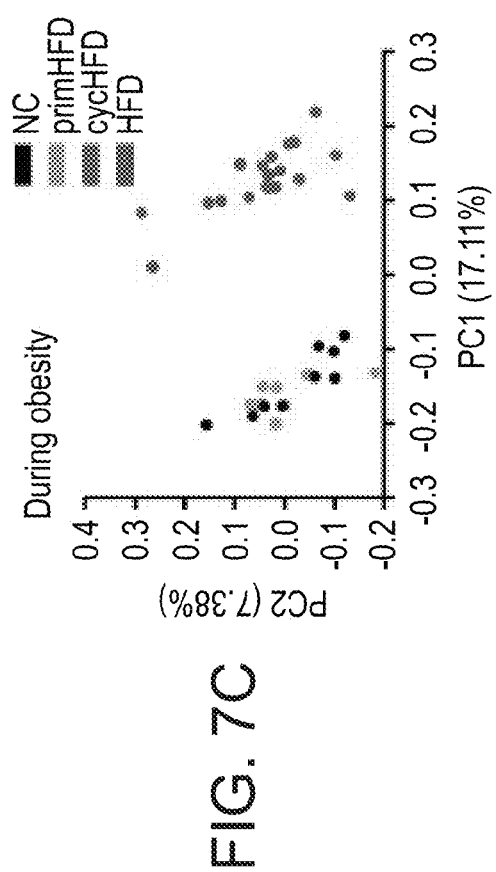
Figure 15A:
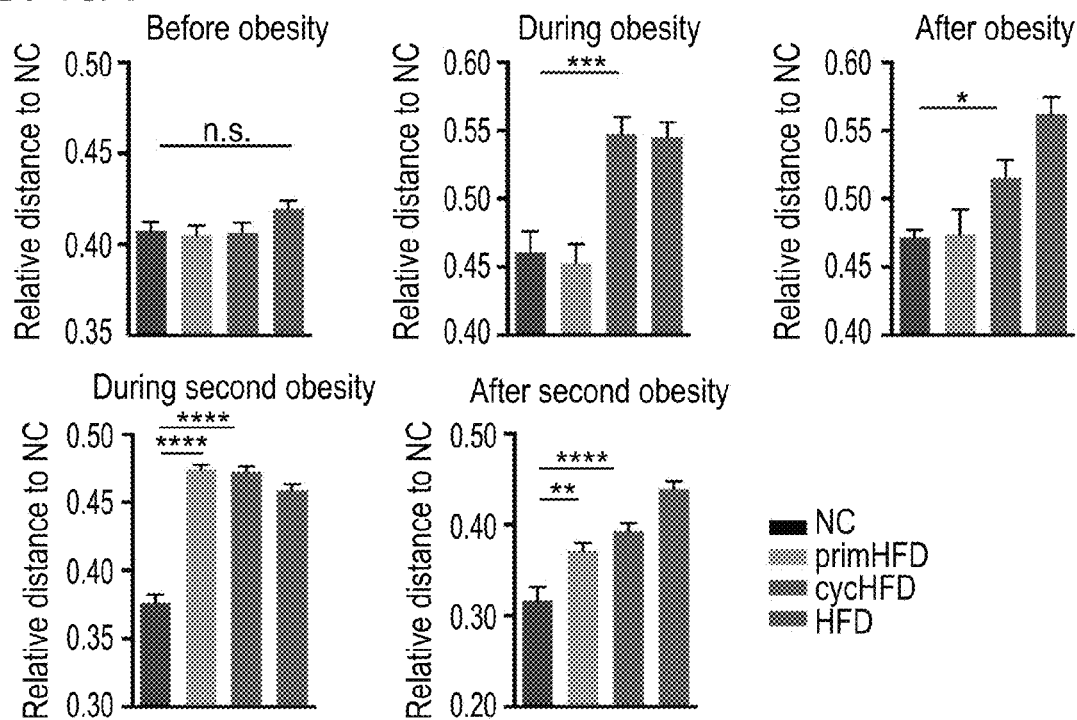
Figure 15B:
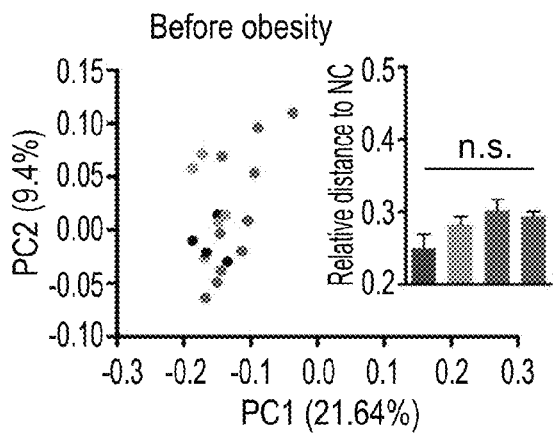
Figure 15C:
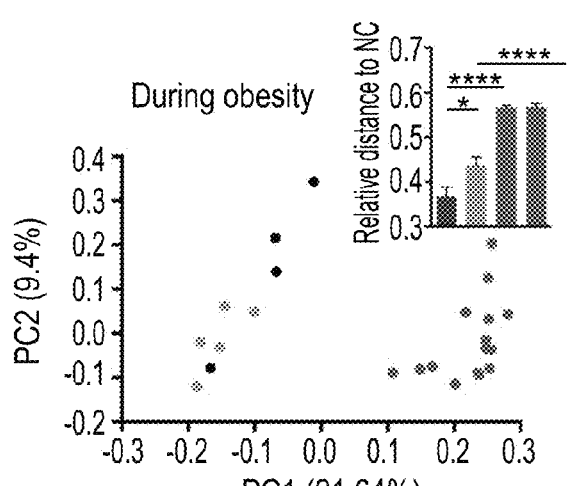
Figure 15D:
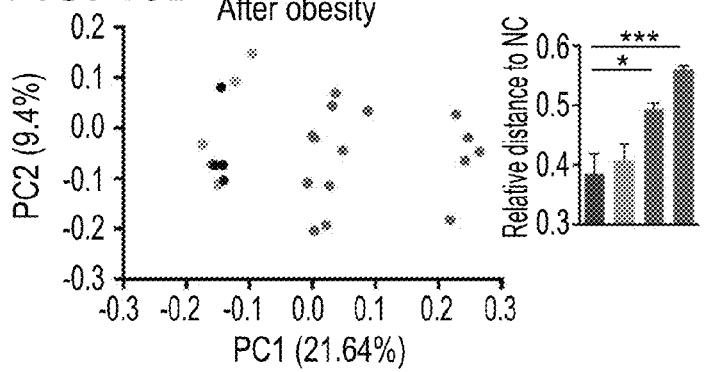

In contrast, the composition of the intestinal microbiota, which had assumed a dysbiotic state during the primary obesity phase, did not return to its original composition following post-dieting weight and metabolic normalization (FIGS. 7A-D and FIG. 15A). Instead, the microbiota assumed an intermediate configuration between the dysbiotic and normal states (FIG. 7D and FIG. 15A). A similar microbiome configuration shift was observed after recovery from a second cycle of recurrent obesity (FIGS. 7E,F and FIG. 15A). These findings were confirmed by targeting an alternative region of the 16S locus for amplicon sequencing (FIGS. 15B-D). Notably, in addition to the significant alteration in bacterial composition persisting after metabolic normalization (FIG. 2E), bacterial alpha-diversity was reduced during the obese state but did not recover upon return to normal weight and metabolic homeostasis (FIG. 2F). To determine the operational taxonomic units (OTUs) that remained altered after dieting, the OTU abundance of weight cycling mice was normalized to age-matched NC controls and the OTUs were classified according to their temporal behavior. Notably, only 45% of all OTUs returned to pre-obesity levels after dieting (FIG. 7G and FIGS. 15E-F), while obesity-induced effects on the microbiome persisted in multiple bacterial taxa (FIGS. 15G-L). Similarly, persistent post-obesity microbiota alterations in composition and alpha-diversity were noted in mice in which weight loss had been aided with celastrol treatment (FIGS. 15J-M).

Figure 7I:
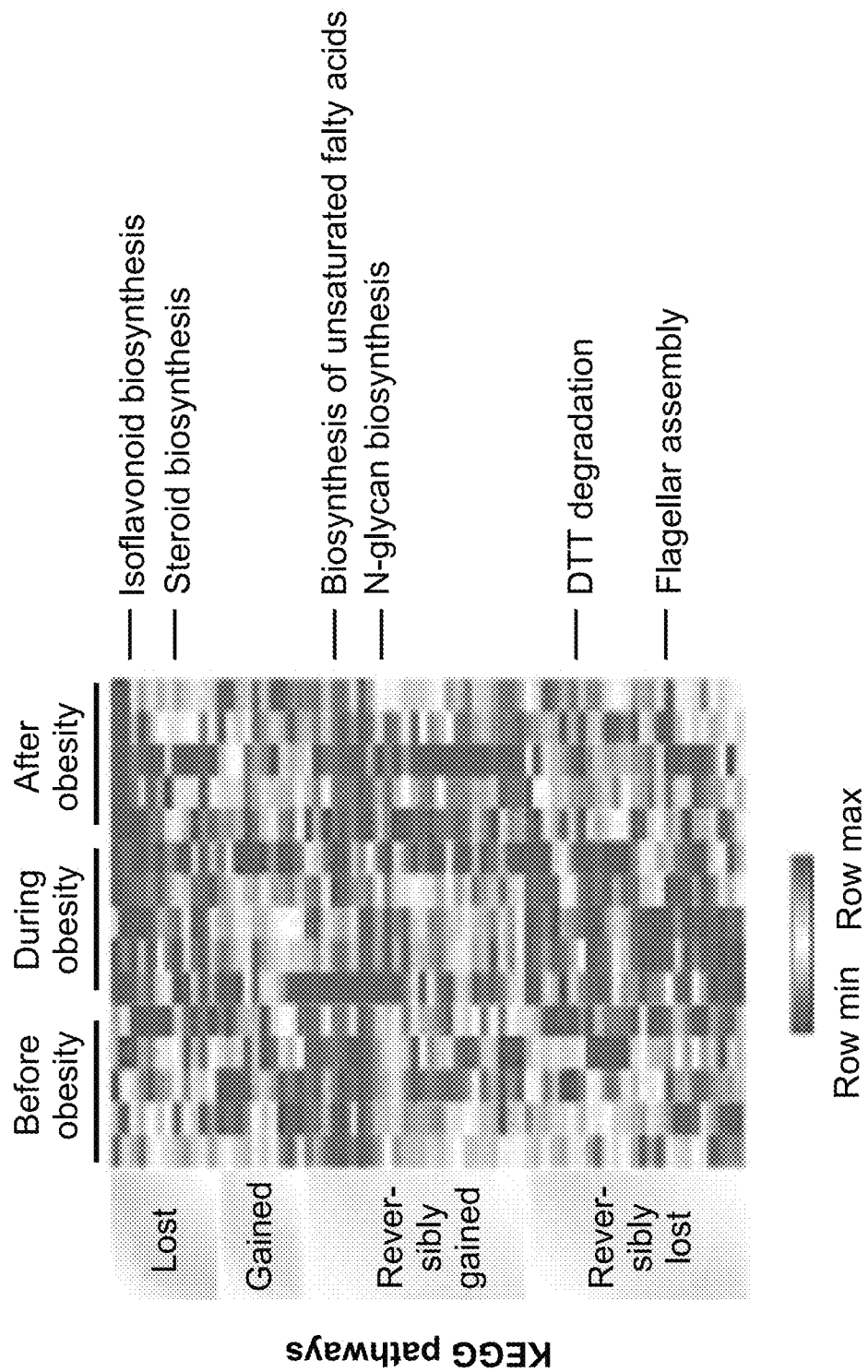
Figure 16A:
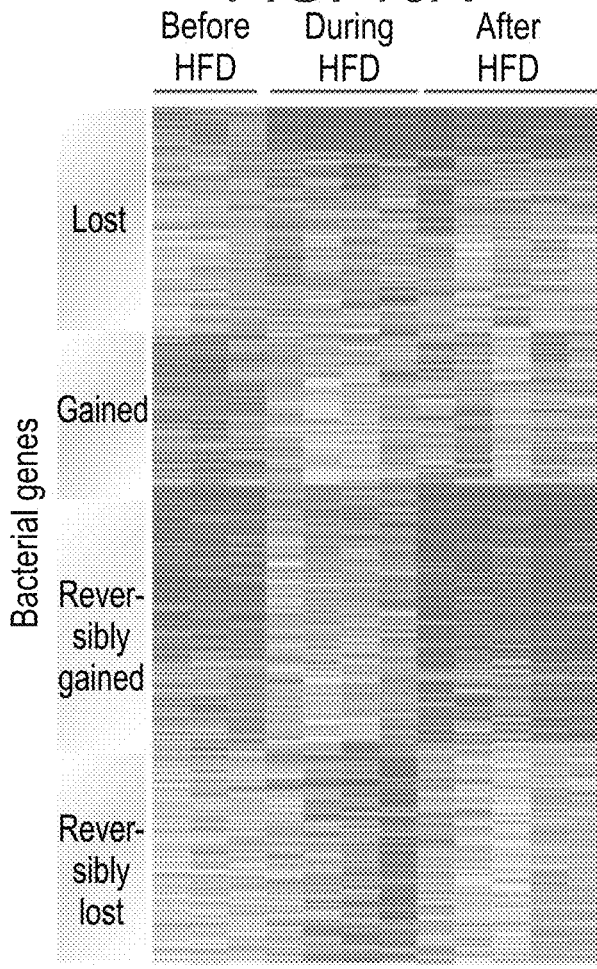
Figure 16B:
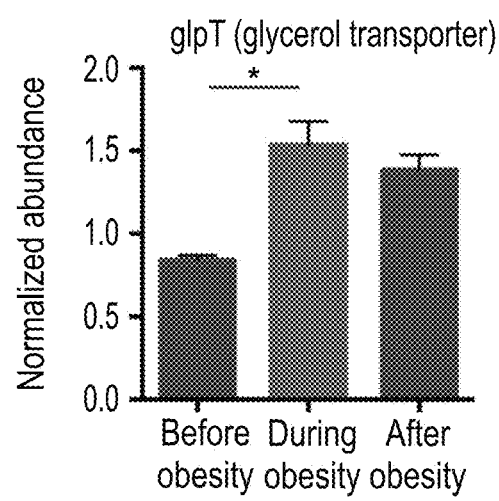
Figure 16C:
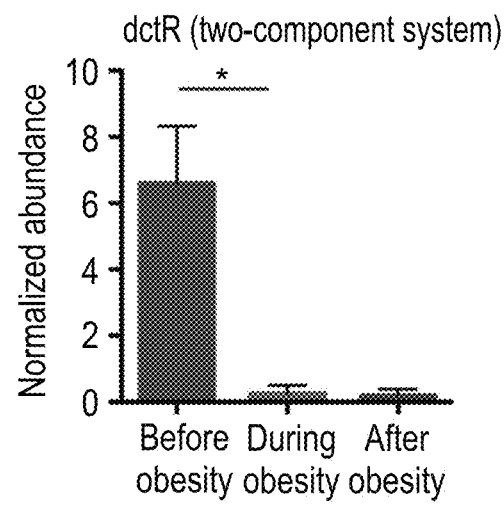
Figure 16D:
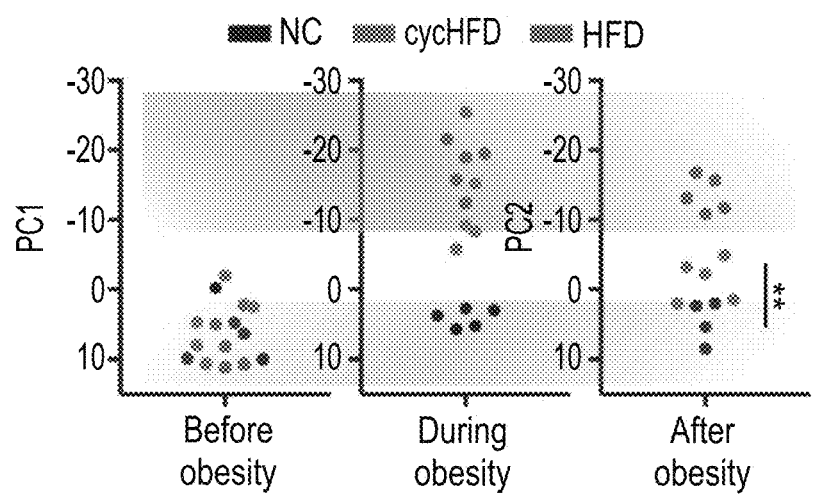
Figure 16E:
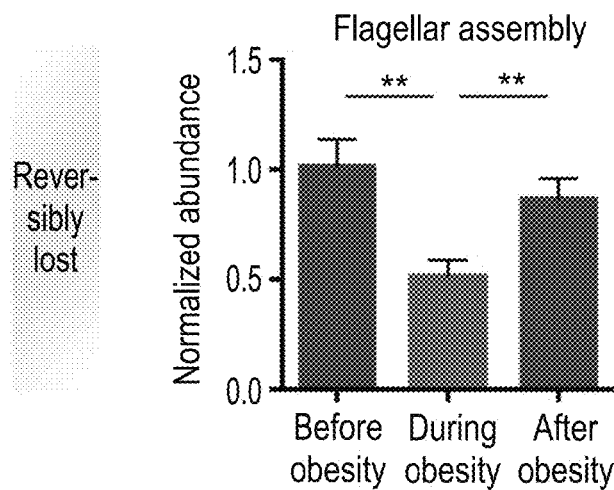
Figure 16F:
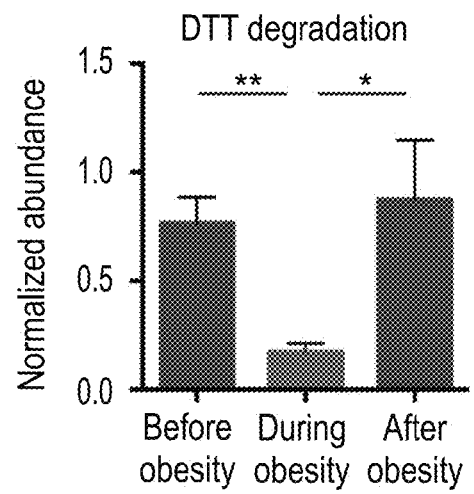
Figure 16G:
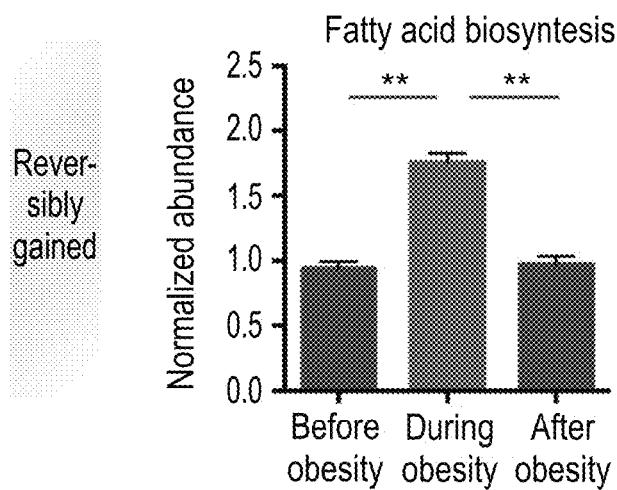
Figure 16H:
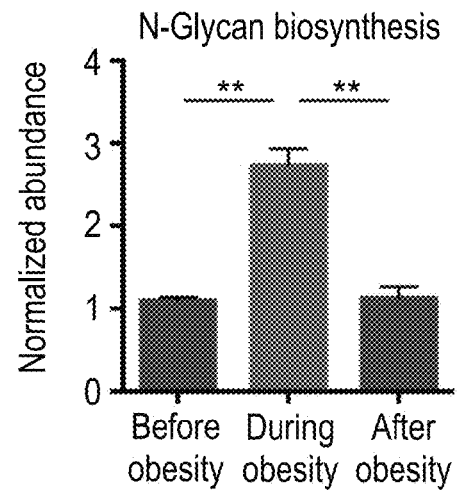
Figure 16I:
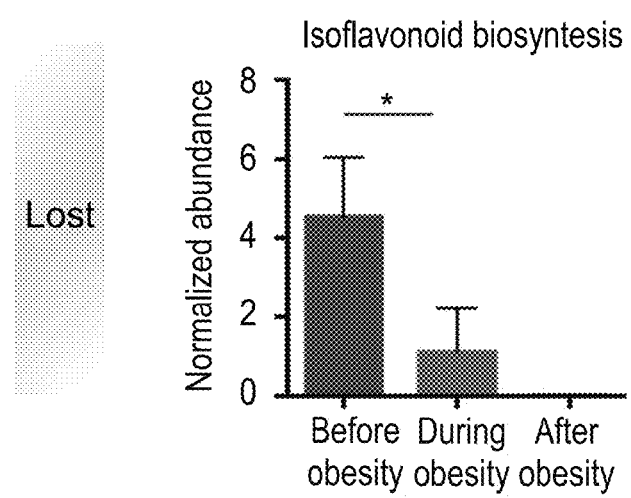
Figure 16J:
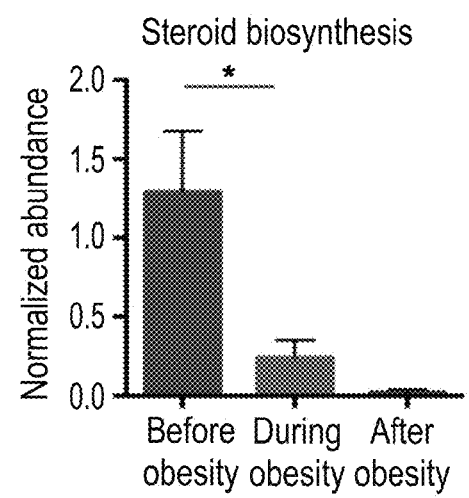

To determine the functional consequences of this incomplete post-dieting microbiota recovery, the present inventors performed shotgun metagenomic sequencing and normalized the temporal behavior of gene abundances to NC controls. They identified 773 bacterial genes whose abundance was altered by high-fat diet and did not return to control levels after dieting (FIGS. 16A-C). Likewise, microbial functionalities did not fully recover in previously dieting mice, both at the level of gene modules (FIG. 16D) and functional pathways (FIG. 7H). Similar to OTUs, reversal of obesity led only to a partial recovery of microbial functions (FIGS. 16E-H), with multiple obesity-induced microbiome aberrations persisting during weight loss (FIG. 7I). Abundances of genes from multiple metabolic pathways, including isoflavonoid and steroid biosynthesis, were reduced during high-fat feeding and did not recover upon dieting (FIGS. 16I-J). Collectively, these data indicate that reversal of obesity by dieting results in a microbiome configuration that remains altered as compared to control mice without prior obesity, even at a state when metabolic normalization is reached.

Example 8

Post-Dieting Microblome Alterations Contribute to Exacerbated Weight Regain (Further to Example 3)

Figure 17A:
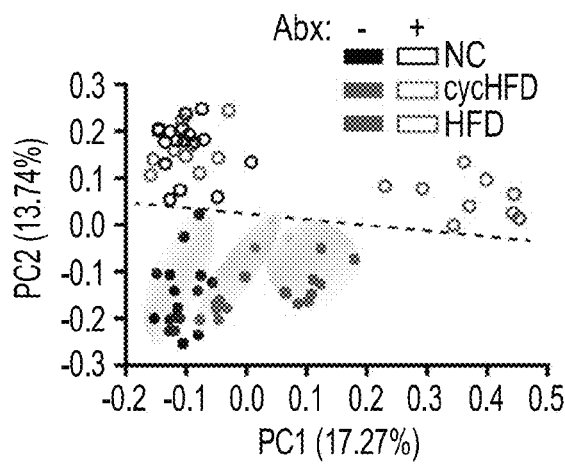
Figure 17B:
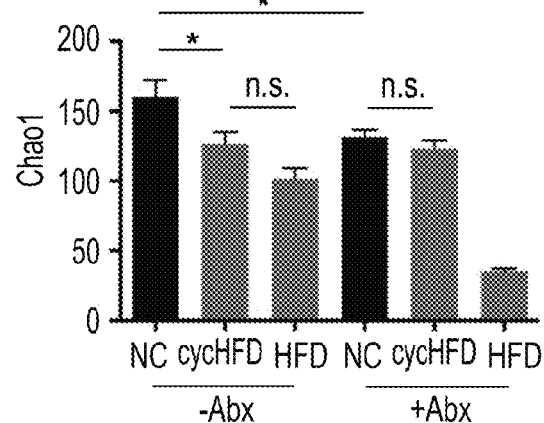
Figure 17C:
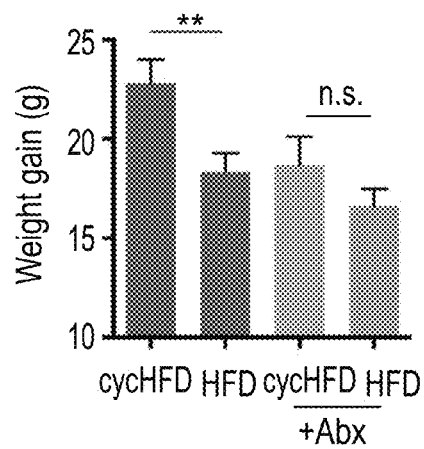
Figure 17D:
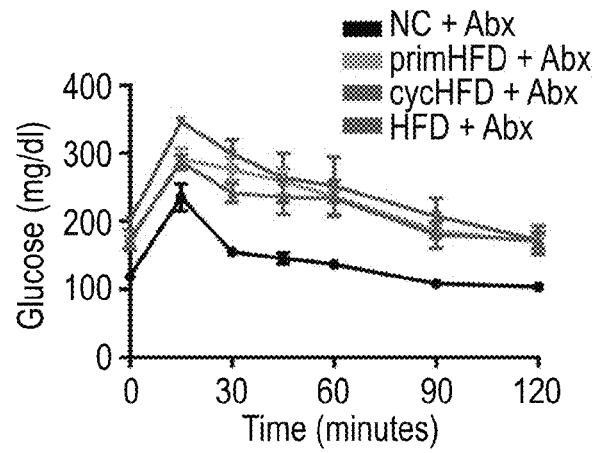
Figure 17E:
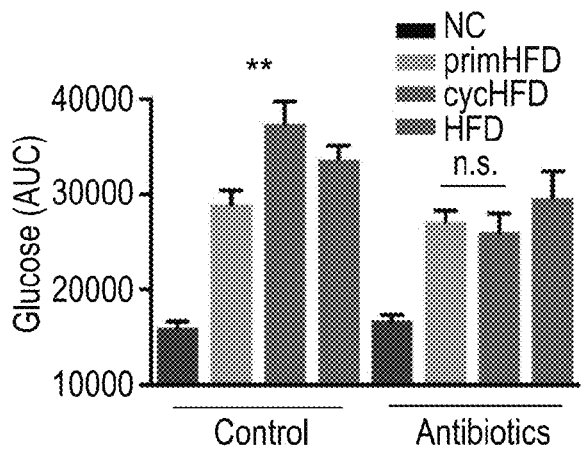
Figure 17F:
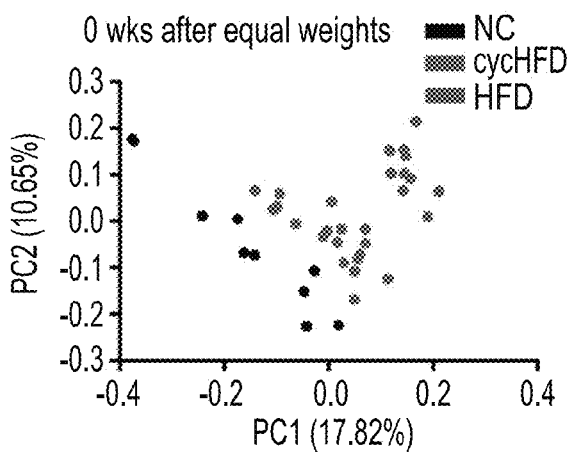
Figure 17G:
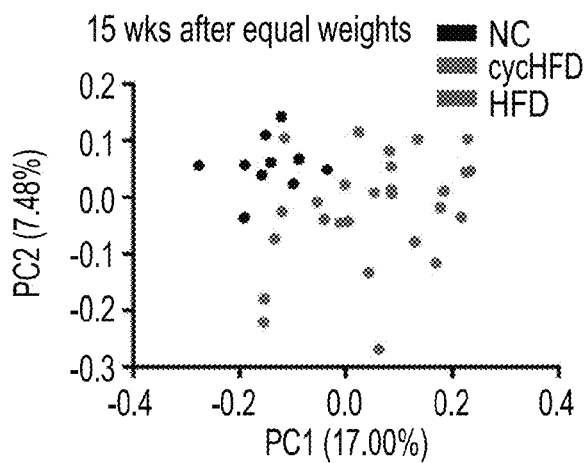
Figure 17H:
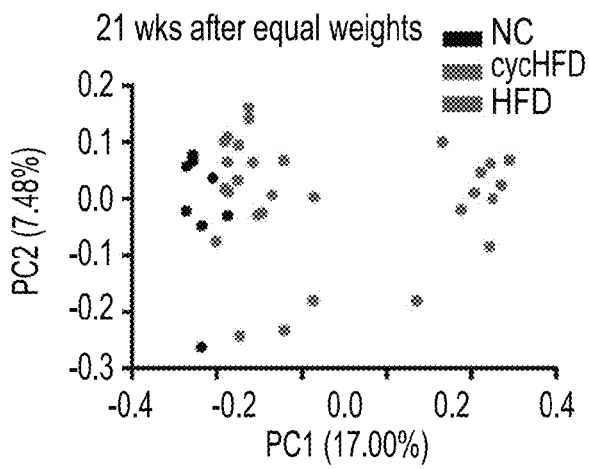

The present inventors next sought to investigate whether the persistent post-obesity microbiome signature was causally involved in the metabolic complications associated with recurrent weight gain. To this end, they treated mice with broad-spectrum antibiotics during the post-obesity weight loss period (FIG. 3A). Expectedly, antibiotic treatment during dieting abolished the post-obesity microbiome signature and equilibrated the microbiota composition and alpha diversity between previously obese mice and NC controls, while the microbiota of non-antibiotics-treated controls maintained an intermediate configuration (FIG. 3B and FIGS. 17A-B). Remarkably, antibiotic treatment also abrogated the exacerbation of metabolic derangements upon re-exposure to HFD, including weight gain, body fat content and glucose intolerance, as compared to non-antibiotics-treated weight-cycling mice (FIGS. 3C,D and FIGS. 17C-E).

Figure 17I:
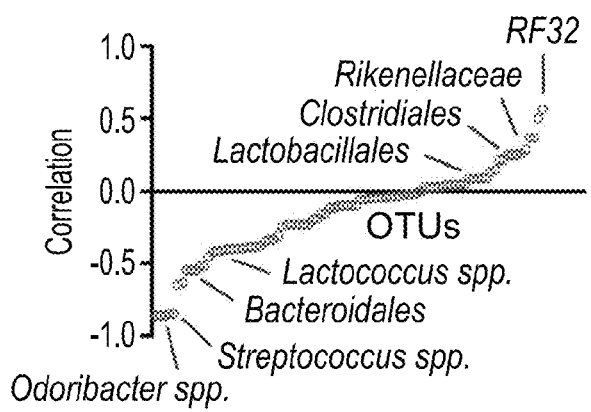
Figure 17J:
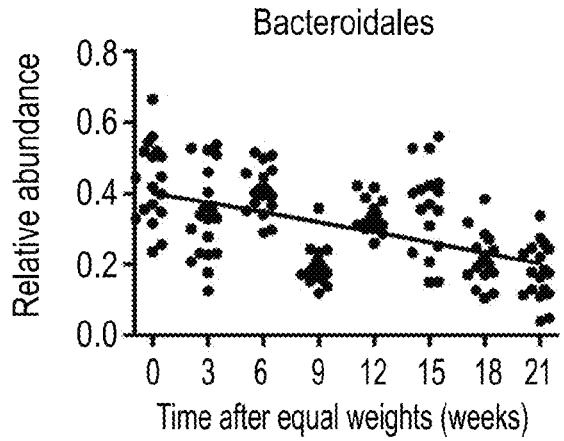
Figure 17K:
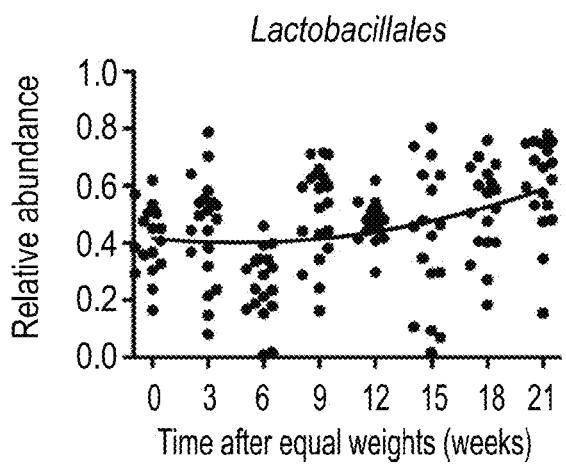
Figure 17L:
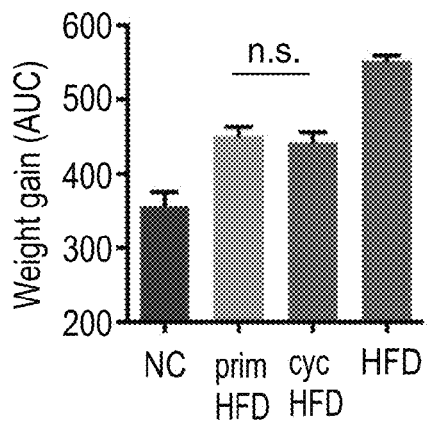

Next, the time required for spontaneous reversal of the persistent post-dieting microbiome alterations was determined. To this end, the microbiota composition was monitored every three weeks upon return of previously obese mice to phenotypic normality (FIG. 8A). Notably, spontaneous reversion of the post-cycling microbiota composition back to NC configuration was achieved only 21 weeks after the completion of successful dieting, i.e. a time period more than five times longer than the initial weight gain or dieting period (FIG. 8B and FIGS. 17F-H). The return to compositional normality in the post-obesity microbiota was associated with gradual acquisition or loss of bacterial taxa (FIGS. 17I-K). Importantly, following the spontaneous microbiota equilibration, re-exposure to HFD resulted in an indistinguishable weight gain in the cycling versus primary HFD-fed mouse groups (FIG. 8A and FIG. 17L).

Figure 18B:
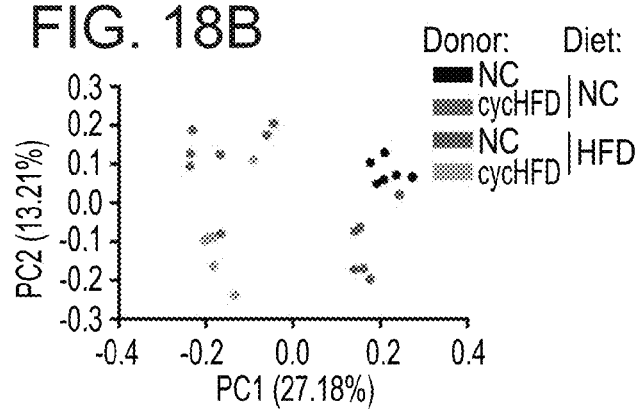
Figure 18C:
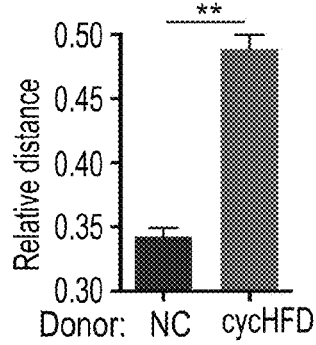
Figure 18D:
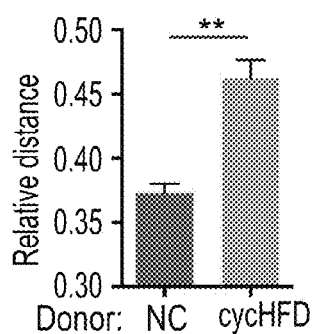
Figure 18E:
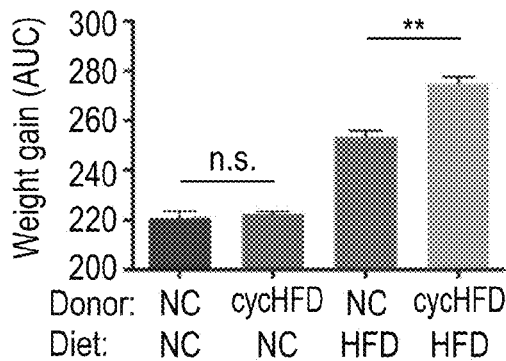
Figure 18F:
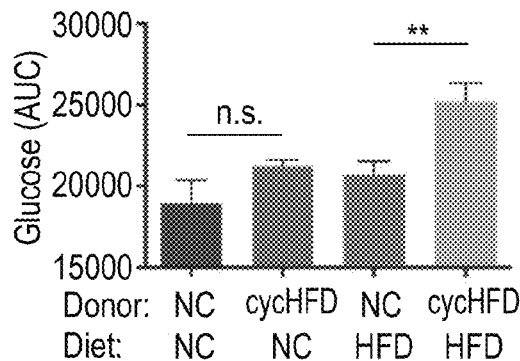

Additionally, fecal transfer experiments were performed, in which the microbiota from previously obese mice (cy-cHFD) and from phenotypically identical controls (NC) was transferred to germ-free mice, which were subsequently fed either a NC diet or HFD (FIG. 18A). The compositional differences between the microbiota from formerly weight-cycling mice and controls persisted in germ-free recipients (FIGS. 18B-D). Notably, under NC conditions, naïve and post-cycling microbiome-transplanted germ-free mice featured similar weight and glucose tolerance (FIGS. 31, J and FIGS. 18E, F), suggesting that the post-obesity microbiome per se did not feature obesogenic properties. In contrast, when fed a HFD, recipients of post-weight cycling microbiota exhibited significantly enhanced weight gain and glucose intolerance as early as one week after fecal transplantation, as compared to recipients of microbiome from control NC-consuming mice (FIGS. 31, J and FIGS. 18E, F). Thus, enhanced metabolic derangements in cycling microbiome-transplanted HFD-fed germ-free mice developed even in the absence of previous bouts of obesity in recipient mice, indicating that the post-dieting microbiome configuration coupled with a secondary obesogenic challenge suffices to induce an enhanced metabolic phenotype. Together, these data suggest that the post-dieting microbiota contributes to the susceptibility to develop aggravated metabolic complications upon re-exposure to obesity-inducing conditions.

Example 9

Microbiota Composition is Predictive of Post-Dieting Weight Regain (Further to Example 4)

Figure 9A:
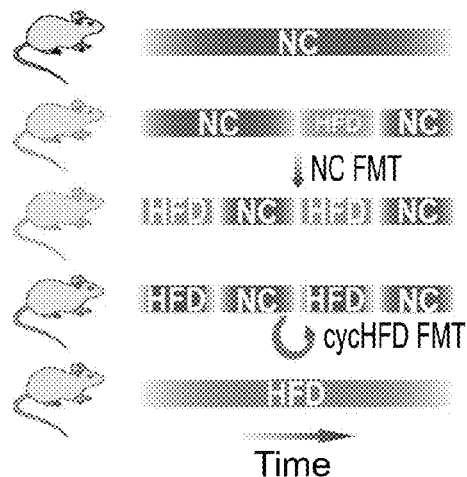
Figure 9B:
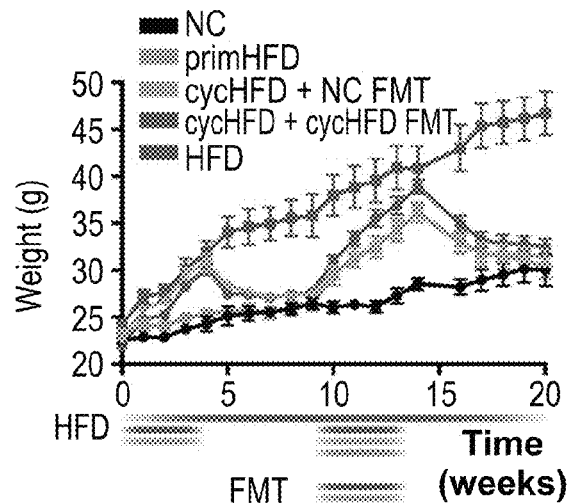
Figure 9C:
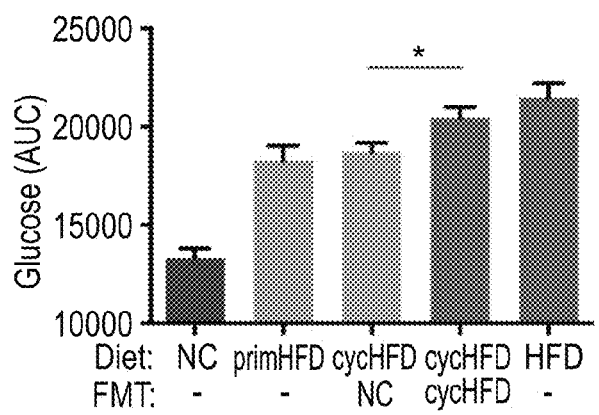
Figure 9D:
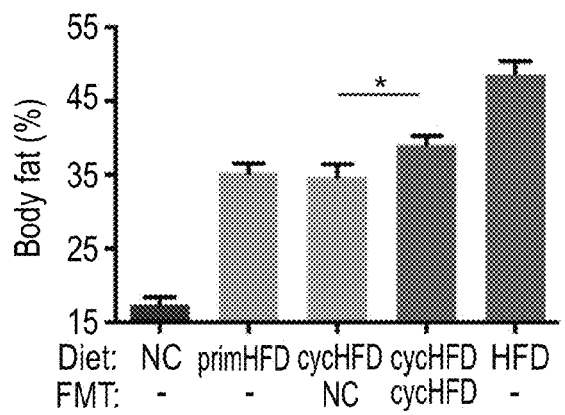
Figure 9E:
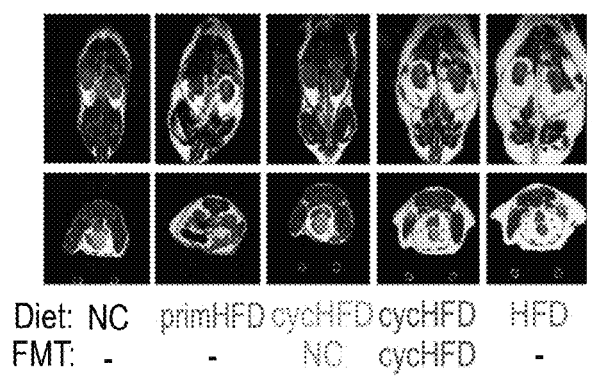
Figure 9F:
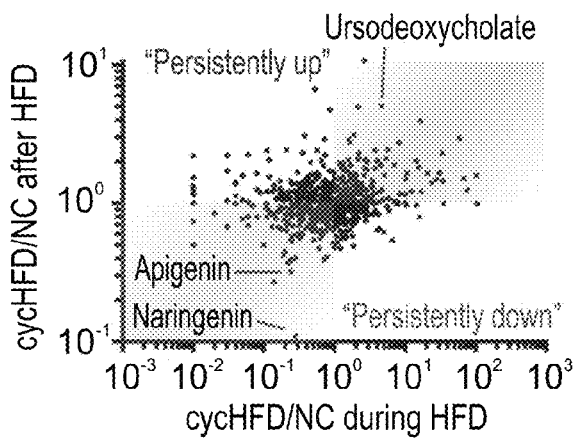

Given the above causal connection between microbiome configuration and post-dieting weight regain, the present inventors next asked whether the extent of recurrent weight gain could be computationally predicted for each individual mouse based on its microbiota composition at the post-dieting 'nadir' period. They therefore profiled the microbiota composition of 25 mice that had undergone post-obesity dieting until metabolic normality and 25 weight-matched NC controls (FIG. 9A). They first devised a machine-learning algorithm, based solely on the microbiota composition, aimed at predicting a history of obesity or lack thereof (FIG. 4A, see Methods). Notably, the derived random forest classifier predicted obesity history nearly perfectly (AUC=0.96, FIG. 4B).

Figure 18G:
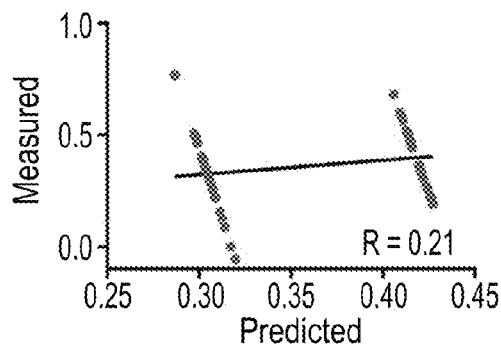
Figure 18H:
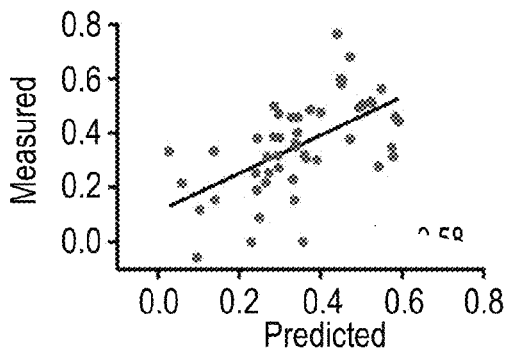
Figures 19G, 19H:
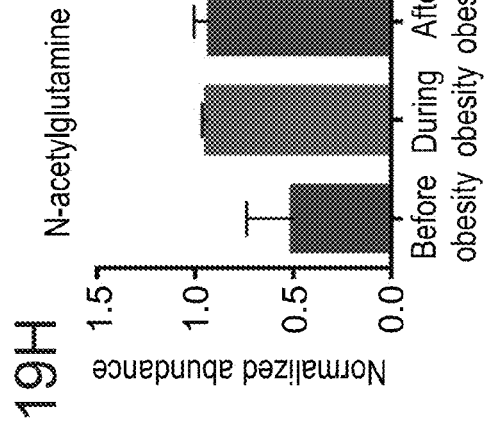
Figure 19I:
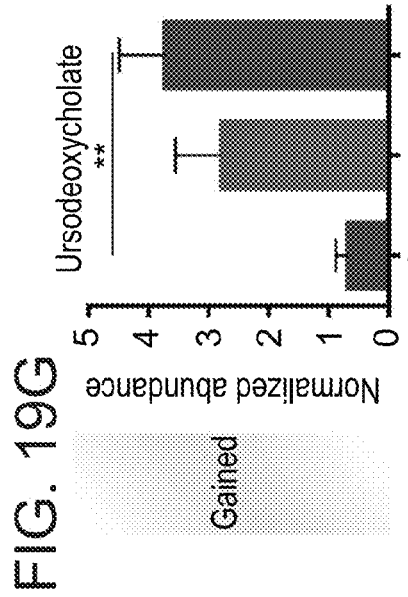

The present inventors next attempted at predicting the exact extent of weight regain of each mouse upon secondary exposure to HFD, based on its post-dieting microbiome configuration. Prediction solely based on obesity history (i.e., without any machine learning model employed) yielded a low prediction accuracy (R=0.21, FIG. 18G). In contrast, a 16S rDNA-based prediction using a leave-one-out-cross-validation scheme performed significantly better (R=0.58, FIG. 18H). Strikingly, a two-step algorithm that first predicts obesity history and then predicts weight regain based on the predicted history, achieved a highly accurate prediction of the extent of weight regain across individual mice (R=0.72, FIG. 4D).

To determine which features of the microbiota contribute to the algorithm's ability to predict the degree of weight gain, all OTUs detected in the fecal microbiomes were ranked according to feature importance for prediction (FIG. 4E). Notably, a total of 189 OTUs contributed to the algorithm's predictions and the magnitude of their contributions displayed a continuum with no OTU standing out as a major contributor (FIG. 4F). This suggests that the composition of the commensal bacteria as a whole, rather than a small subset of species, drives the post-dieting microbiome alterations that contribute to the susceptibility to relapsing obesity. Together, these results suggest that the microbiota configuration may be used to predict the history of HFD-induced obesity in mice as well as the extent of personalized weight regain that occurs upon recurrence of the same obesity-inducing conditions.

Example 10

Microblome-modulated metabolites contribute to post-dieting weight regain (further to Example 5)

The present inventors next determined whether microbiome modulation during the post-weight cycling period could ameliorate the extent of secondary weight gain and its metabolic complications. To this aim, they performed daily fecal microbiome transplantation (FMT) for 4 weeks, using 'naïve' or post-dieting donor microbiomes transferred into colonized weight cycling mice during the 'nadir' post-dieting time point (FIG. 9A). Upon transplantation, compositional differences between the microbiota from formerly weight cycling mice and controls persisted in the corresponding FMT recipients (FIGS. 18I-K). Notably, recipients of a non-cycling 'healthy' microbiome during the 'nadir' post-obese period exhibited an ameliorated secondary weight gain (FIG. 9B and FIGS. 18L-M), reduced glucose intolerance (FIG. 9C and FIG. 18N), decreased body fat (FIGS. 9D, E), and increased lean mass (FIG. 18O) as compared to mice undergoing a control FMT with a 'post-cycling' microbiome. These results indicate that restoration of normal microbiota function after dieting may prevent exacerbation of metabolic derangements upon weight regain.

Given the effectiveness of FMT, the present inventors sought to gain further insight into how microbiota replenishment ameliorates the propensity for recurrent obesity after weight loss. To this end, they longitudinally compared the fecal metabolomics profile between mice undergoing HFD-induced weight cycling and control NC-fed mice. They normalized the metabolite levels in weight cycling mice to those of age-matched NC controls at each time point and then classified each metabolite according to temporal patterns. Expectedly, HFD induced major alterations in the fecal metabolome, which were partially reversed upon subsequent weight loss (FIGS. 9F, G and FIGS. 19A-D). However, in nearly half of all metabolites altered by HFD, including several bile acids, the obesity-induced changes persisted after return to phenotypic normality (FIGS. 9F, G and FIGS. 19E-H).

Among the metabolites most significantly depleted by HFD whose levels did not recover upon re-gain of metabolic health were the dietary flavonoids apigenin and naringenin (FIGS. 9F-I). Both compounds remained suppressed for as long as 15 weeks after weight normalization (FIGS. 9H-1). Flavonoids are commonly ingested diet-derived compounds that are metabolized by the intestinal microbiota. The microbiome contribution to intestinal flavonoid levels was evident from the elevated levels of apigenin and naringenin in antibiotics-treated or germ-free mice (FIG. 9J). The present inventors therefore hypothesized that a combination of dietary flavonoid availability and microbiome-mediated flavonoid degrading capacity may contribute to the total intestinal flavonoid pool. To this end, they followed the kinetics of flavonoids, the flavonoid-biosynthetic enzyme chalcone synthase and the flavonoid-degrading enzyme flavanone 4-reductase (FIG. 19I and Supplementary Table 1), over the course of an obesity/weight loss cycle (FIG. 20A).

Figure 20B:
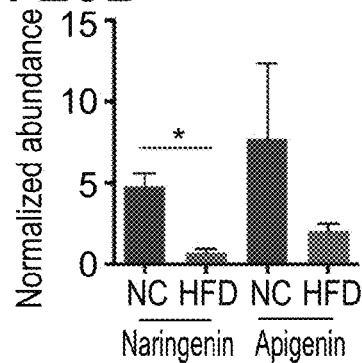
Figure 20C:
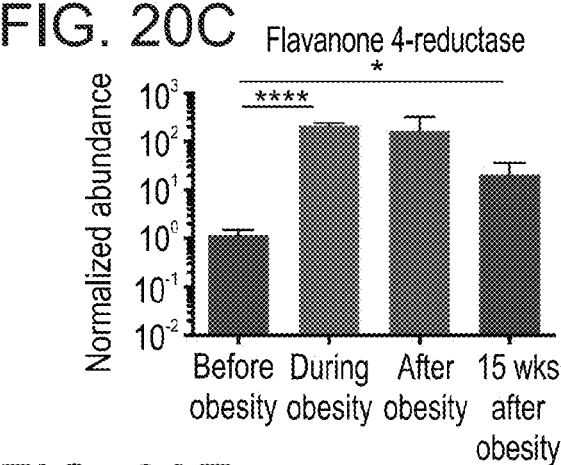
Figure 20D:
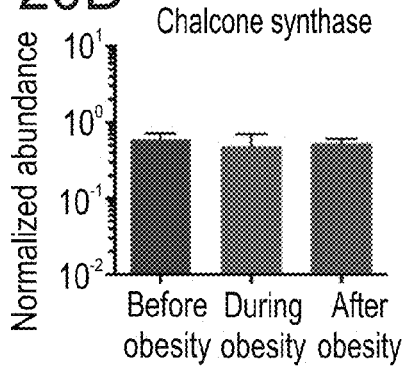
Figure 20E:
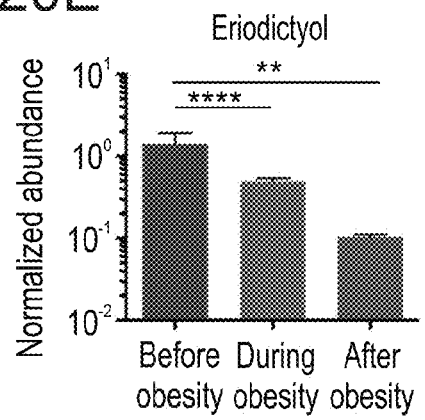
Figure 20F:
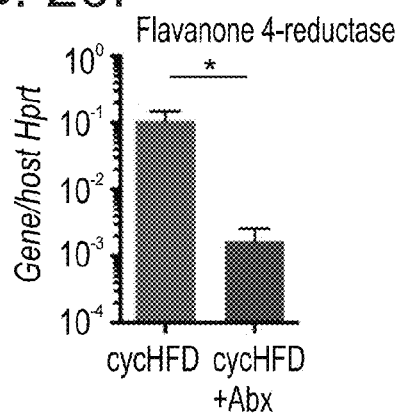
Figure 20G:
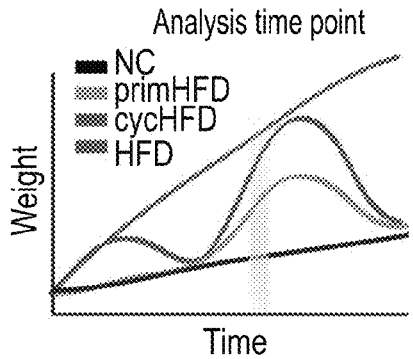
Figure 20H:
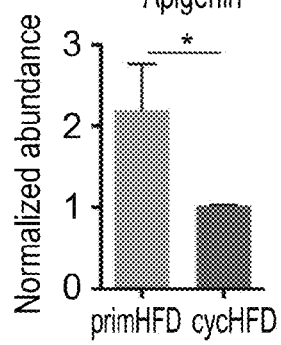
Figure 20I:
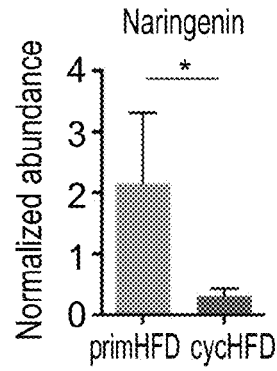

During primary obesity, low intestinal flavonoid levels (FIGS. 9H, I) were contributed by low flavonoid availability in HFD (FIG. 20B) coupled to a microbiome shift towards a flavonoid-degrading configuration, as evident by the increase in flavanone 4-reductase, and not in chalcone synthase (FIGS. 20C, D). During induction of weight loss by reversion to NC diet, dietary flavonoid availability returned to its normally high level (FIG. 20B) yet intestinal flavonoid levels remained persistently low, including those of naringenin-derived eriodictyol (FIGS. 9H, I and FIG. 20E). At this 'nadir' phase, the flavonoid-degrading microbiome contributed to the low flavonoid levels, as suggested by persistently elevated flavanone 4-reductase (FIG. 20C) and by the effect of antibiotic treatment during the weight reduction phase, which diminished the levels of flavonone 4-reductase (FIG. 20F) and normalized flavonoid levels (FIG. 9K). Upon acute secondary induction of obesity (FIG. 20G), the combination of low dietary flavonoid availability (FIG. 20B), coupled with the long-standing presence of a flavonoid-degrading microbiome and associated low flavonoid levels, likely contributed to reduced flavonoid levels in weight cycling mice as compared to controls undergoing primary weight gain (FIGS. 20H, I).

Figure 10B:
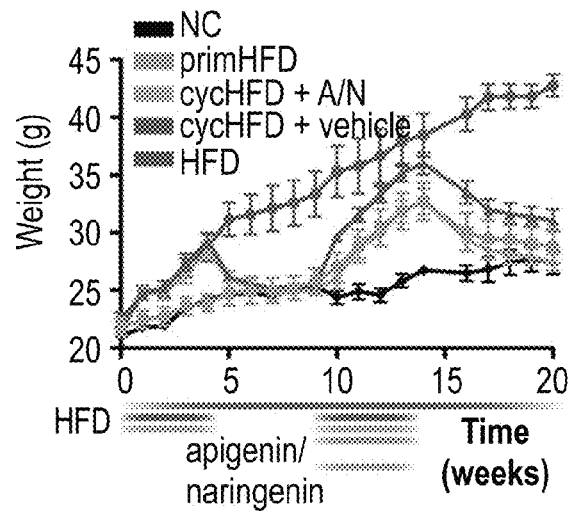
Figure 10C:
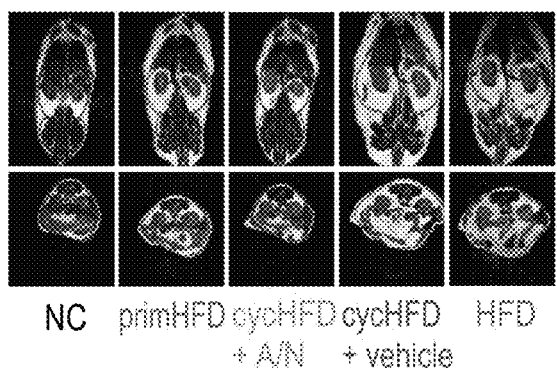
Figure 10D:
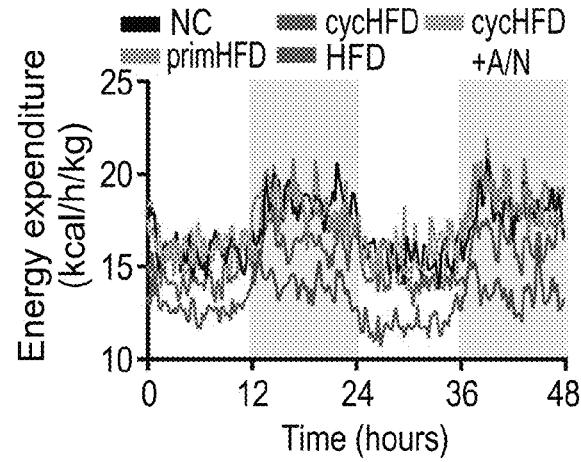
Figure 10E:
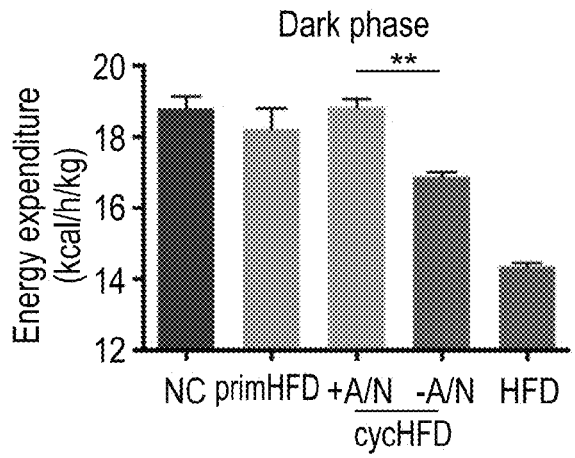
Figure 10F:
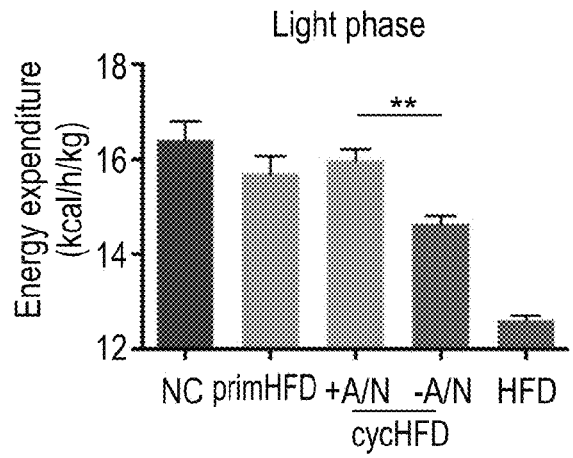

Apigenin and naringenin have been reported to affect food intake, adipocyte differentiation, and lipid metabolism. The present inventors therefore hypothesized that FMT-induced restoration of a naive flavonoid-degrading microbiome in weight cycling mice, or direct flavonoid replenishment of these mice, may ameliorate the exacerbated relapsing obesity phenotype. Indeed, oral daily administration of both flavonoids to post-dieting mice during the post dieting 'nadir' and secondary weight regain period (FIG. 10A) resulted in normalization of intestinal apigenin and naringenin levels to control levels (FIGS. 20J, K), with no effect noted on microbiome composition (FIG. 20L). Similar to FMT, combined flavonoid treatment ameliorated the rate of secondary weight regain (FIGS. 10B, C and FIGS. 20M, N), an effect that was also achieved by solely administering naringenin (FIGS. 20O, P). Together, these results suggest that low apigenin and naringenin levels in post-dieting mice contribute to an exacerbated weight regain, while their therapeutic replenishment ameliorates this susceptibility.

Example 11

Flavonoids Modulate Post-Dieting Weight Regain and Regulate UCP-1 Expression

To investigate possible mechanisms by which apigenin and naringenin ameliorate recurrent post-dieting obesity, metabolic and behavioral parameters in flavonoid-administered weight cycling mice were compared to non-treated weight cycling mice. Interestingly, weight-adjusted energy expenditure was markedly reduced in weight-cycling mice (FIGS. 10D-F and FIGS. 21A-F), but was normalized upon flavonoid administration (FIGS. 10D-F and FIGS. 21A-F), suggesting that apigenin and naringenin might impact host energy expenditure. Of note, a similar effect of flavonoids on weight management was observed in previous studies, while the link between flavonoid supplementation and enhanced energy expenditure was reached only upon normalization of energy expenditure to body weight. Other metabolic parameters were not affected by flavonoid treatment (FIGS. 21G-H and FIGS. 22A-F). Similarly, mice treated with antibiotics at the 'nadir' period featured enhanced energy expenditure upon re-administration of HFD (FIG. 10G, FIGS. 22G-L and FIGS. 23A-C), in line with higher levels of flavonoids (FIG. 9K) and amelioration of the exacerbated weight regain (FIG. 3C), but did not alter other metabolic parameters during recurrent weight gain (FIGS. 23D-L).

Finally, the present inventors pursued possible mechanisms by which flavonoids may participate in regulation of host energy expenditure. Since brown adipose tissue (BAT) is a major regulator of thermogenesis in mammals, and since other members of the flavonoid family have been previously associated with the induction of the major thermogenic factor uncoupling protein-1 (UCP-1), Ucp1 expression was analyzed in mice fed NC or HFD and orally administered with apigenin and naringenin. As early as two weeks after the start of flavonoid treatment, Ucp1 transcript levels were significantly elevated in the BAT of mice fed a HFD, but not in those fed a normal chow (FIG. 10H). Likewise, Ucp1 expression was elevated in weight cycling mice upon apigenin and naringenin supplementation during the HFD-induced weight regain period (FIG. 10I). Ucp1 was also induced by flavonoids in BAT explants in a concentration-dependent manner (FIG. 10J), suggesting a direct effect of apigenin and naringenin on modulation of gene expression in BAT. Given that antibiotic treatment elevated intestinal flavonoid levels (FIG. 9K) and host energy expenditure (FIG. 10G and FIGS. 22H, I), the present inventors determined the levels of UCP-1 in the BAT of antibiotics-treated weight cycling mice. Indeed, both transcript and protein levels of UCP-1 were found to be elevated in the group receiving antibiotics (FIGS. 10K, M), providing a potential mechanistic explanation for recent observations of Ucp1 induction in germ-free mice.

Taken together, these associations suggest a model in which HFD promotes the growth of flavonoid-metabolizing bacteria, which in turn decrease the amount of bioavailable flavonoids, thereby negatively regulating UCP-1-driven energy expenditure and promoting recurrent weight gain (FIG. 10N). Full validation of this model merits future studies investigating whether the flavonoid effect on BAT Ucp1 expression directly drives enhanced energy expenditure and thereby contributes to ameliorated weight regain.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

1. Stevens, J., Oakkar, E. E., Cui, Z., Cai, J. & Truesdale, K. P. US adults recommended for weight reduction by 1998 and 2013 obesity guidelines, NHANES 2007-2012. Obesity 23, 527-531, doi:10.1002/oby.20985 (2015).
2. Tobias, D. K. et al. Effect of low-fat diet interventions versus other diet interventions on long-term weight change in adults: a systematic review and meta-analysis. Lancet Diabetes Endocrinol 3, 968-979, doi:10.1016/S2213-8587(15)00367-8 (2015).
3. Anastasiou, C. A., Karfopoulou, E. & Yannakoulia, M. Weight regaining: From statistics and behaviors to physiology and metabolism. Metabolism 64, 1395-1407, doi:10.1016/j.metabol.2015.08.006 (2015).
4. Pietilainen, K. H., Saarni, S. E., Kaprio, J. & Rissanen, A. Does dieting make you fat? A twin study. Int J Obes (Lond) 36, 456-464, doi:10.1038/ijo.2011.160 (2012).

5. Neumark-Sztainer, D. et al. Obesity, disordered eating, and eating disorders in a longitudinal study of adolescents: how do dieters fare 5 years later? J Am Diet Assoc 106, 559-568, doi:10.1016/j.jada.2006.01.003 (2006).
6. Saarni, S. E., Rissanen, A., Sarna, S., Koskenvuo, M. & Kaprio, J. Weight cycling of athletes and subsequent weight gain in middleage. Int J Obes (Lond) 30, 1639-1644, doi:10.1038/sj.ijo.0803325 (2006).
7. Turnbaugh, P. J. et al. An obesity-associated gut microbiome with increased capacity for energy harvest. Nature 444, 1027-1031, doi:10.1038/nature05414 (2006).
8. Ley, R. E., Turnbaugh, P. J., Klein, S. & Gordon, J. I. Microbial ecology: human gut microbes associated with obesity. Nature 444, 1022-1023, doi:10.1038/4441022a (2006).
9. Korem, T. et al. Growth dynamics of gut microbiota in health and disease inferred from single metagenomic samples. Science 349, 1101-1106, doi:10.1126/science.aac4812 (2015).
10. David, L. A. et al. Diet rapidly and reproducibly alters the human gut microbiome. Nature 505, 559-563, doi:10.1038/nature12820 (2014).
11. Ma, X. et al. Celastrol Protects against Obesity and Metabolic Dysfunction through Activation of a HSF1-PGC1alpha Transcriptional Axis. Cell metabolism 22, 695-708, doi:10.1016/j.cmet.2015.08.005 (2015).
12. Liu, J., Lee, J., Salazar Hernandez, M. A., Mazitschek, R. & Ozcan, U. Treatment of obesity with celastrol. Cell 161, 999-1011, doi:10.1016/j.cell.2015.05.011 (2015).
13. Elinav, E. et al. Pegylated leptin antagonist is a potent orexigenic agent: preparation and mechanism of activity. Endocrinology 150, 3083-3091, doi:10.1210/en.2008-1706 (2009).
14. Kanehisa, M., Sato, Y., Kawashima, M., Furumichi, M. & Tanabe, M.
KEGG as a reference resource for gene and protein annotation. Nucleic acids research 44, D457-462, doi:10.1093/nar/gkv1070 (2016).
15. Turnbaugh, P. J., Backhed, F., Fulton, L. & Gordon, J. I. Diet-induced obesity is linked to marked but reversible alterations in the mouse distal gut microbiome. Cell host & microbe 3, 213-223, doi:10.1016/j.chom.2008.02.015 (2008).
16. Pothuraju, R., Sharma, R. K., Chagalamarri, J., Kavadi, P. K. & Jangra, S. Influence of milk fermented with Lactobacillus rhamnosus NCDC 17 alone and in combination with herbal ingredients on diet induced adiposity and related gene expression in C57BL/6J mice. Food Funct 6,3576-3584, doi:10.1039/c5fo00781j (2015).
17. Bongaerts, G. P. & Severijnen, R. S. A reassessment of the PROPATRIA study and its implications for probiotic therapy. Nat Biotechnol 34, 55-63, doi:10.1038/nbt.3436 (2016).
18. Zeevi, D. et al. Personalized Nutrition by Prediction of Glycemic Responses. Cell 163, 1079-1094, doi:10.1016/j.cell.2015.11.001 (2015).
19. Arpaia, N. et al. Metabolites produced by commensal bacteria promote peripheral regulatory T-cell generation. Nature 504, 451-455, doi:10.1038/nature12726 (2013).
20. Smith, P. M. et al. The microbial metabolites, short-chain fatty acids, regulate colonic Treg cell homeostasis. Science 341, 569-573, doi:10.1126/science.1241165 (2013).
21. Levy, M. et al. Microbiota-Modulated Metabolites Shape the Intestinal Microenvironment by Regulating NLRP6 Inflammasome Signaling. Cell 163, 1428-1443, doi:10.1016/j.cell.2015.10.048 (2015).
22. Lee, C. H. et al. Frozen vs Fresh Fecal Microbiota Transplantation and Clinical Resolution of Diarrhea in Patients With Recurrent Clostridium difficile Infection: A Randomized Clinical Trial. JAMA 315, 142-149, doi:10.1001/jama.2015.18098 (2016).
23. Myoung, H. J., Kim, G. & Nam, K. W. Apigenin isolated from the seeds of Perilla frutescens britton var crispa (Benth.) inhibits food intake in C57BL/6J mice.
Arch Pharm Res 33, 1741-1746, doi:10.1007/s12272-010-1105-5 (2010).
24. Guo, X., Liu, J., Cai, S., Wang, O. & Ji, B. Synergistic interactions of apigenin, naringin, quercetin and emodin on inhibition of 3T3-L1 preadipocyte differentiation and pancreas lipase activity. Obes Res Clin Pract, doi:10.1016/j.orcp.2015.08.004 (2015).
25. Assini, J. M. et al. Naringenin prevents obesity, hepatic steatosis, and glucose intolerance in male mice independent of fibroblast growth factor 21. Endocrinology 156, 2087-2102, doi:10.1210/en.2014-2003 (2015).
26. Zar Kalai, F. et al. Antiobesity Effects of an Edible Halophyte Nitraria retusa Forssk in 3T3-L1 Preadipocyte Differentiation and in C57B6J/L Mice Fed a High Fat Diet-Induced Obesity. Evid Based Complement Alternat Med 2013, 368658, doi:10.1155/2013/368658 (2013).
27. Carmody, R. N. et al. Diet dominates host genotype in shaping the murine gut microbiota. Cell host & microbe 17, 72-84, doi:10.1016/j.chom.2014.11.010 (2015).
28. Sonnenburg, E. D. et al. Diet-induced extinctions in the gut microbiota compound over generations. Nature 529, 212-215, doi:10.1038/nature16504 (2016).
29. Ridaura, V. K. et al. Gut microbiota from twins discordant for obesity modulate metabolism in mice. Science 341, 1241214, doi:10.1126/science.1241214 (2013).
30. Escande, C. et al. Flavonoid apigenin is an inhibitor of the NAD+ ase CD38: implications for cellular NAD+ metabolism, protein acetylation, and treatment of metabolic syndrome. Diabetes 62, 1084-1093, doi:10.2337/db12-1139 (2013).
31. Rakoff-Nahoum, S., Paglino, J., Eslami-Varzaneh, F., Edberg, S. & Medzhitov, R. Recognition of commensal microflora by toll-like receptors is required for intestinal homeostasis. Cell 118, 229-241, doi:10.1016/j.cell.2004.07.002 (2004).
32. Caporaso, J. G. et al. QIIME allows analysis of high-throughput community sequencing data. Nature methods 7, 335-336, doi:10.1038/nmeth.f.303 (2010).
33. Elinav, E. et al. NLRP6 inflammasome regulates colonic microbial ecology and risk for colitis. Cell 145, 745-757, doi:10.1016/j.cell.2011.04.022 (2011).
34. Qin, J. et al. A human gut microbial gene catalogue established by metagenomic sequencing. Nature 464, 59-65, doi:10.1038/nature08821 (2010).
35. Aaron, J. et al. Polarization microscopy with stellated gold nanoparticles for robust monitoring of molecular assemblies and single biomolecules. Optics express 16, 2153-2167 (2008).
36. Kanehisa, M. & Goto, S. KEGG: kyoto encyclopedia of genes and genomes. Nucleic acids research 28, 27-30 (2000).
37. Kanehisa, M. et al. Data, information, knowledge and principle: back to metabolism in KEGG. Nucleic acids research 42, D199-205, doi:10.1093/nar/gkt1076 (2014).

What is claimed is:

1. A method of reducing the risk of weight gain in a subject who has completed a weight loss program and reached a target weight, the method comprising administering to the subject a fecal transplant of a donor subject who has not undergone a weight loss program, wherein said donor subject has a BMI between 18.5-24.9, thereby reducing the risk of weight gain in the subject.

2. The method of claim 1, further comprising administering to the subject a flavonoid or a combination of flavonoids.

3. The method of claim 2, wherein said flavonoid is apigenin and/or naringenin.

4. The method of claim 1, further comprising administering to the subject a probiotic.

5. The method of claim 1, further comprising administering to the subject an antibiotic.

6. The method of claim 5, wherein said antibiotic agent downregulates an amount and/or activity of the class Mollicutes or of the order Bacteroidales.

7. The method of claim 1, further comprising analyzing a signature of a gut microbiome of the subject prior to the administering.

* * * * *

SEQUENCE LISTING

```
<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_feature
<222> LOCATION: (1)..(8)
<223> OTHER INFORMATION: n is a, c, g, or t

<400> SEQUENCE: 1
nnnnnnnnag agtttgatcc tggctcag                                   28

<210> SEQ ID NO 2
<211> LENGTH: 19
<212> TYPE: DNA
<213> ORGANISM: Artificial Sequence
<220> FEATURE:
<223> OTHER INFORMATION: Single strand DNA oligonucleotide

<400> SEQUENCE: 2
tgctgcctcc cgtaggagt                                             19
```